(12) United States Patent
Egawa et al.

(10) Patent No.: US 7,901,792 B2
(45) Date of Patent: Mar. 8, 2011

(54) QUINOXALINE DERIVATIVE, AND LIGHT EMITTING ELEMENT, LIGHT EMITTING DEVICE, AND ELECTRONIC APPLIANCE USING THE SAME

(75) Inventors: Masakazu Egawa, Kanagawa (JP); Sachiko Kawakami, Kanagawa (JP); Nobuharu Ohsawa, Kanagawa (JP); Hideko Inoue, Kanagawa (JP); Satoshi Seo, Kanagawa (JP); Ryoji Nomura, Kanagawa (JP)

(73) Assignee: Semiconductor Energy laboratory Co., Ltd. (JP)

( * ) Notice: Subject to any disclaimer, the term of this patent is extended or adjusted under 35 U.S.C. 154(b) by 962 days.

(21) Appl. No.: 11/518,484

(22) Filed: Sep. 8, 2006

(65) Prior Publication Data
US 2007/0059553 A1 Mar. 15, 2007

(30) Foreign Application Priority Data

Sep. 12, 2005 (JP) .................. 2005-264253

(51) Int. Cl.
*H01L 51/54* (2006.01)
(52) U.S. Cl. .................. 428/690; 428/917; 544/353
(58) Field of Classification Search .................. None
See application file for complete search history.

(56) References Cited

U.S. PATENT DOCUMENTS

| | | | |
|---|---|---|---|
| 4,760,006 A | 7/1988 | Pawlowski | |
| 5,366,811 A | 11/1994 | Higashi et al. | |
| 5,466,392 A | 11/1995 | Hironaka et al. | |
| 6,303,238 B1 | 10/2001 | Thompson et al. | |
| 6,541,129 B1 | 4/2003 | Kawamura et al. | |
| 6,723,445 B2 | 4/2004 | Li et al. | |
| 7,034,026 B2 | 4/2006 | Barnett et al. | |
| 7,074,534 B2 | 7/2006 | Herron et al. | |
| 7,238,806 B2 | 7/2007 | Inoue et al. | |
| 7,245,073 B2 | 7/2007 | Shitagaki et al. | |
| 7,271,858 B2 | 9/2007 | Yamazaki et al. | |
| 7,399,537 B2 | 7/2008 | Kawamura et al. | |
| 2003/0143430 A1 | 7/2003 | Kawamura et al. | |
| 2005/0065342 A1 | 3/2005 | Shitagaki et al. | |
| 2005/0186446 A1* | 8/2005 | Shitagaki et al. | 428/690 |
| 2005/0191527 A1 | 9/2005 | Fujii et al. | |
| 2005/0242715 A1* | 11/2005 | Inoue et al. | 313/504 |
| 2006/0263637 A1 | 11/2006 | Ohsawa et al. | |
| 2007/0213527 A1 | 9/2007 | Inoue et al. | |
| 2008/0241591 A1 | 10/2008 | Kawamura et al. | |

FOREIGN PATENT DOCUMENTS

| | | |
|---|---|---|
| EP | 0 166 230 A1 | 1/1986 |
| EP | 0 502 202 A1 | 9/1992 |
| EP | 1 029 909 A1 | 8/2000 |
| EP | 1 616 864 | 1/2006 |
| EP | 1 690 866 A1 | 8/2006 |
| JP | 60-258169 | 12/1985 |
| JP | 64-057261 | 3/1989 |
| JP | 7-48385 | 2/1995 |
| JP | 7-150137 | 6/1995 |
| JP | 8-73443 | 3/1996 |
| JP | 10-25473 | 1/1998 |
| JP | 2000-309566 | 11/2000 |
| JP | 2003-040873 | 2/2003 |
| JP | 2003-515897 | 5/2003 |
| JP | 2006-016384 | 1/2006 |
| WO | WO-92/05131 A1 | 4/1992 |
| WO | WO 01/41512 A1 | 6/2001 |
| WO | WO 2004/094389 A1 | 11/2004 |
| WO | WO 2005/054261 | 6/2005 |

(Continued)

OTHER PUBLICATIONS

Huang et al., "Quinoxalines Incorporating Triarylamines: Dipolar Electroluminescent Materials with Tunable Emission Characteristics", Journal of the Chinese Chemical Society, 2006, vol. 53, No. 1, pp. 233-242.

(Continued)

*Primary Examiner* — D. Lawrence Tarazano
*Assistant Examiner* — Gregory Clark
(74) *Attorney, Agent, or Firm* — Husch Blackwell LLP

(57) ABSTRACT

A quinoxaline derivative expressed by the general formula (1) is provided. (Each of $R^1$ to $R^{12}$ represents one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group. $Ar^1$ represents one of a substituted or unsubstituted biphenyl group and a substituted or unsubstituted terphenyl group, and $Ar^2$ represents one of a substituted or unsubstituted phenyl group, a substituted or unsubstituted biphenyl group, a substituted or unsubstituted terphenyl group, and a substituted or unsubstituted monocyclic heterocycle group.)

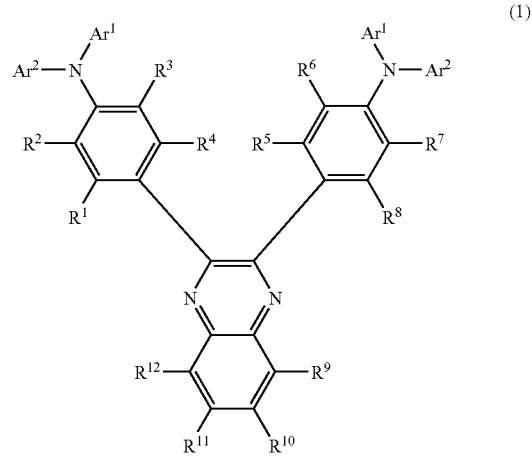

33 Claims, 35 Drawing Sheets

FOREIGN PATENT DOCUMENTS

| WO | WO-2005/115061 A1 | 12/2005 |
|---|---|---|
| WO | WO-2006/049334 A1 | 5/2006 |

OTHER PUBLICATIONS

International Search Report, Application No. PCT/JP2006/317806, dated Nov. 21, 2006.

Written Opinion, Application No. PCT/JP2006/317806, dated Nov. 21, 2006.

Lewis, R.J., Sr., *Hawley's Condensed Chemical Dictionary*, 12th ed., Van Nostrand Reinhold, pub., 1993, p. 594.

Jakubke, H-D et al. ed., *Concise Encyclopedia Chemistry*, Walter de Gruyter, pub., 1993, p. 490.

Burrows, H.D. et al, "Fluorescence Study of Dehydroabietic Acid-Based Bipolar Arylamine-Quinoxalines," Journal of Fluorescence, vol. 16, No. 2, Mar. 2006, pp. 227-231.

Delvigs, P., "Effects of Multifunctional Crosslinking Agents on the Thermomechanical Properties of Polyimide Films," Polymer Engineering and Science, vol. 16, No. 5, May 1976, pp. 323-326.

Brock,T et al., "Synthesis and Characterisation of Porous Particulate Polyimides," Journal of Materials Chemistry, vol. 4, No. 2, 1994, pp. 229-236.

Office Action re U.S. Appl. No. 10/826,838, dated Feb. 7, 2007.

Office Action re U.S. Appl. No. 10/826,838, dated Sep. 11, 2007.

Office Action re U.S. Appl. No. 10/826,838, dated Apr. 4, 2008.

International Search Report re application No. PCT/JP2004/005022, dated Jun. 15, 2004.

Written Opinion re application No. PCT/JP2004/005022, dated Jun. 15, 2004 (with English translation).

Tang, C.W. et al, "Organic Electroluminescent Diodes," Applied Physics Letters, vol. 51, No. 12, Sep. 21, 1987, pp. 913-915.

Adachi, C. et al, "Electroluminescence in Organic Films with Three-Layer Structure," Japanese Journal of Applied Physics, vol. 27, No. 2, Feb. 1988, pp. L269-L271.

Thomas, K.R.J. et al, "Quinoxalines Incorporating Triarylamines: Potential Electroluminescent Materials with Tunable Emission Characteristics," Chem. Mater., vol. 14, No. 6, May 3, 2002, pp. 2796-2802.

Office Action re Chinese application No. CN 200680033318.3, dated Dec. 18, 2009 (with English translation).

Parker, S.P. et al, editors, *McGraw-Hill Dictionary of Chemical Terms*, vol. 3 RD ED, 1985, p. 200.

\* cited by examiner

QUINOXALINE DERIVATIVE, AND LIGHT EMITTING ELEMENT, LIGHT EMITTING DEVICE, AND ELECTRONIC APPLIANCE USING THE SAME

TECHNICAL FIELD

The present invention relates to a quinoxaline derivative, and a light emitting element, a light emitting device, and an electronic appliance each of which uses the quinoxaline derivative.

BACKGROUND ART

An organic compound has various material systems compared with an inorganic compound, and has possibility to synthesize a material having various functions depending on the molecular design. Owing to these advantages, photo electronics and electronics which use a functional organic material have been attracting attention in recent years.

For example, a solar cell, a light emitting element, an organic transistor, and the like can be mentioned as examples of an electronic device using an organic compound as a functional organic material. These are devices taking advantage of electric properties and optical properties of the organic compound. Among them, in particular, a light emitting element has been making remarkable development.

It is said that light emission mechanism of a light emitting element is as follows: when a voltage is applied between a pair of electrodes which interpose a light emitting layer, electrons injected from a cathode and holes injected from an anode are recombined in the light emission center of the light emitting layer, so as to form a molecular exciton and energy is released to emit light when the molecular exciton returns to a ground state. As excitation states, a singlet excitation state and a triplet excitation state are known, and light emission is considered to be possible through any of these excitation states.

Such a light emitting element has a lot of problems depending on a material in the case where an element property thereof is improved. In order to solve the problems, improvement of an element structure, development of a material, and the like are carried out.

As the most basic structure of a light emitting element, the following structure is known: a hole transporting layer formed of an organic compound having a hole transporting property and an electron transporting light emitting layer formed of an organic compound having an electron transporting property are stacked to form a thin film of approximately 100 nm thick in total, and this thin film is interposed between electrodes (see Non-Patent Document 1, for example).

A voltage is applied to the light emitting element described in Non-Patent Document 1, thereby light emission can be obtained from organic compounds having a light emitting property and an electron transporting property.

Further, in the light emitting element described in Non-Patent Document 1, functions are separately carried out. That is, a hole transporting layer transports a hole, whereas an electron transporting layer transports an electron and emits light. However, various interactions (for example, formation of exciplex, and the like) occur on an interface of stacked layers. As a result, a change in light emission spectrum or a decline in light emission efficiency may be caused.

In order to improve a change in light emission spectrum or a decline in light emission efficiency which is caused by the interaction at an interface, a light emitting element in which functions are further separately carried out is devised. For example, supposed is a light emitting element having a structure where a light emitting layer is sandwiched between a hole transporting layer and an electron transporting layer (see Non-Patent Document 2, for example).

In such a light emitting element as described in Non-Patent Document 2, a light emitting layer is preferably formed by using a bipolar organic compound which has an electron transporting property and a hole transporting property so that interaction caused at an interface is further suppressed.

However, most organic compounds are monopolar materials having either a hole transporting property or an electron transporting property.

Therefore, a bipolar organic compound having both an electron transporting property and a hole transporting property has been required to be developed.

In Patent Document 1, a bipolar quinoxaline derivative is described. However, since characteristics such as heat resistance are not sufficiently obtained yet, more various bipolar organic compounds have been required to be developed.

[Non-Patent Document 1]
C. W. Tang et al., Applied Physics Letters, vol. 51, No. 12, 913-915 (1987)
[Non-Patent Document 2]
Chihaya Adachi et al., Japanese Journal of Applied Physics, vol. 27, No. 2, L269-L271 (1988)
[Patent Document 1]
PCT International Publication No. 2004/094389

DISCLOSURE OF INVENTION

In view of the aforementioned problems, an object of the invention is to provide a new bipolar organic compound, in particular, a bipolar organic compound having excellent heat resistance. Further, another object is to provide a bipolar organic compound which is electrochemically stabilized.

Further, another object is to provide a light emitting element and a light emitting device of which a driving voltage and power consumption are reduced by using the bipolar organic compound of the invention. Furthermore, another object is to provide a light emitting element and a light emitting device which have excellent heat resistance by using the bipolar organic compound of the invention. In addition, another object is to provide a light emitting element and a light emitting device which have a long life by using the bipolar organic compound of the invention.

Still another object is to provide a long-life electronic appliance consuming low power and having high heat resistance by using the bipolar organic compound of the invention.

One mode of the invention is a quinoxaline derivative expressed by the following general formula (1).

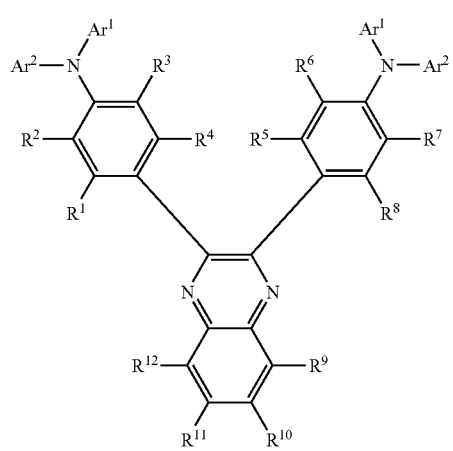

(in the formula, $R^1$ to $R^{12}$ may be the same or different and each represent any one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group. $R^9$, $R^{10}$, and $R^{11}$ may be combined with $R^{10}$, $R^{11}$, and $R^{12}$ respectively to form a condensed ring. $Ar^1$ represents a substituted or unsubstituted biphenyl group or a substituted or unsubstituted terphenyl group. $Ar^2$ represents a substituted or unsubstituted phenyl group, a substituted or unsubstituted biphenyl group, a substituted or unsubstituted terphenyl group, or a substituted or unsubstituted monocyclic heterocycle group.)

Another mode of the invention is a quinoxaline derivative expressed by the following general formula (2).

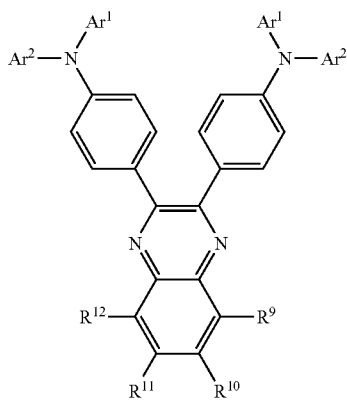

(2)

(in the formula, $R^9$ to $R^{12}$ may be the same or different and each represent any one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group. $R^9$, $R^{10}$, and $R^{11}$ may be combined with $R^{10}$, $R^{11}$, and $R^{12}$ respectively to form a condensed ring. $Ar^1$ represents a substituted or unsubstituted biphenyl group or a substituted or unsubstituted terphenyl group. $Ar^2$ represents a substituted or unsubstituted phenyl group, a substituted or unsubstituted biphenyl group, a substituted or unsubstituted terphenyl group, or a substituted or unsubstituted monocyclic heterocycle group.)

Another mode of the invention is a quinoxaline derivative expressed by the following general formula (3).

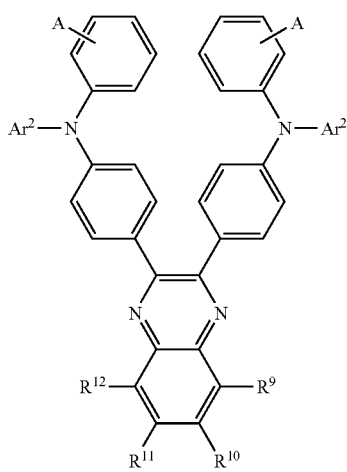

(3)

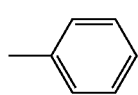

(4)

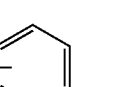

(5)

(in the formula, $R^9$ to $R^{12}$ may be the same or different and each represent any one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group. $R^9$, $R^{10}$, and $R^{11}$ may be combined with $R^{10}$, $R^{11}$, and $R^{12}$ respectively to form a condensed ring. A represents a substituent expressed by the structure formula (4) or the structure formula (5). $Ar^2$ represents a substituted or unsubstituted phenyl group, a substituted or unsubstituted biphenyl group, a substituted or unsubstituted terphenyl group, or a substituted or unsubstituted monocyclic heterocycle group.)

Another mode of the invention is a quinoxaline derivative expressed by the following general formula (6).

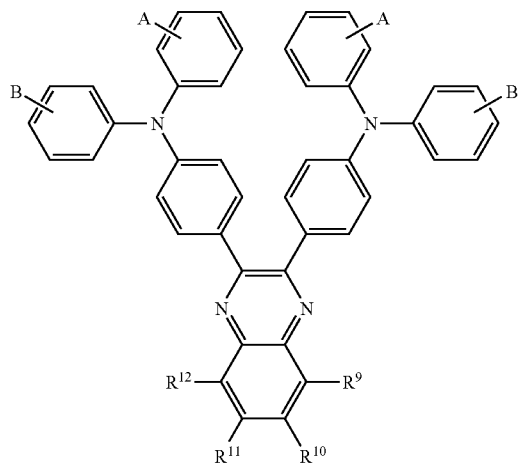

(6)

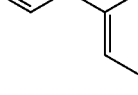

(7)

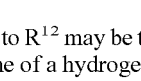

(8)

(in the formula, $R^9$ to $R^{12}$ may be the same or different and each represent any one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group. $R^9$, $R^{10}$, and $R^{11}$ may be combined with $R^{10}$, $R^{11}$, and $R^{12}$ respectively to form a condensed ring. A represents a substituent expressed by the structure formula (7) or the structure formula (8). B represents a hydrogen atom or a substituent expressed by the structure formula (7) or the structure formula (8).)

Another mode of the invention is a quinoxaline derivative expressed by the following general formula (9).

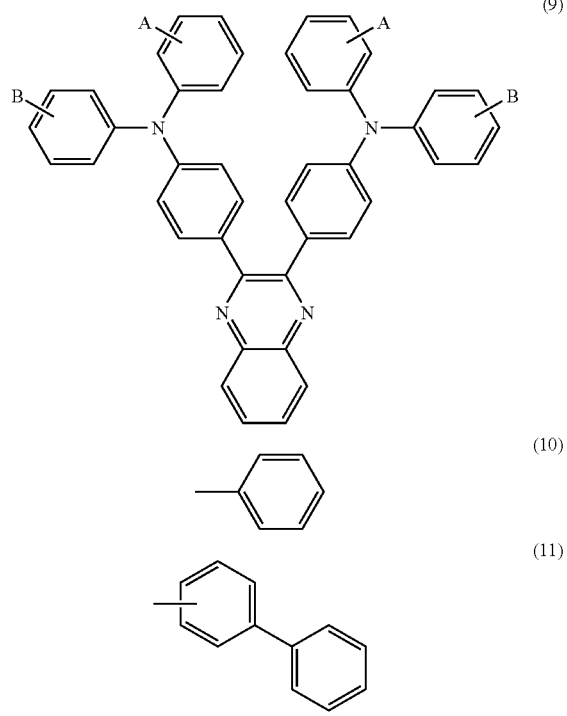

(in the formula, A represents a substituent expressed by the structure formula (10) or the structure formula (11), and B represents a hydrogen atom or a substituent expressed by the structure formula (10) or the structure formula (11).)

Another mode of the invention is a quinoxaline derivative expressed by the following structure formula (14).

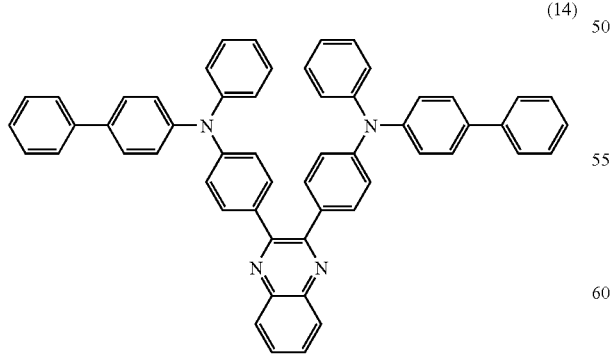

Another mode of the invention is a quinoxaline derivative expressed by the following structure formula (39).

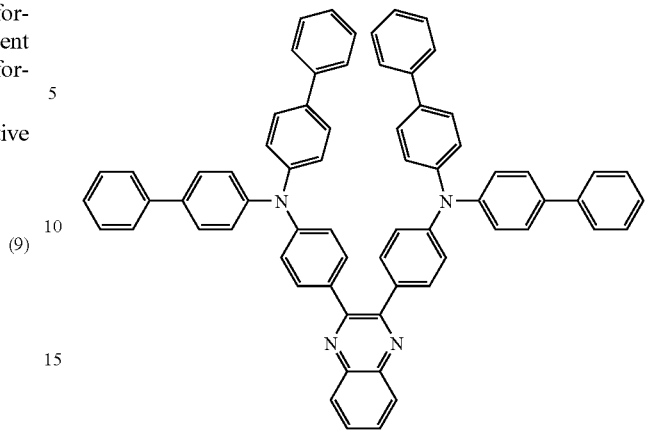

Another mode of the invention is a light emitting element using the aforementioned quinoxaline derivative; specifically, a light emitting element having the aforementioned quinoxaline derivative between a pair of electrodes.

Another mode of the invention is a light emitting element having a light emitting layer between a pair of electrodes, and the light emitting layer has the aforementioned quinoxaline derivative.

Another mode of the invention is a light emitting element having a light emitting layer between a pair of electrodes, and the light emitting layer has the aforementioned quinoxaline derivative and a fluorescent substance.

Another mode of the invention is a light emitting element having a light emitting layer between a pair of electrodes, and the light emitting layer has the quinoxaline derivative and a phosphorescent substance.

In the aforementioned structure, the phosphorescent substance is preferably an organometallic complex including a structure expressed by the general formula (101).

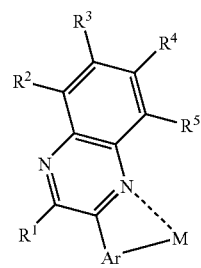

(in the formula, $R^1$ to $R^5$ each represent any one of hydrogen, a halogen element, an acyl group, an alkyl group, an alkoxyl group, an aryl group, a cyano group, and a heterocycle group. Ar represents an aryl group or a heterocycle group. M represents an element which belongs to Group 9 or Group 10.)

Further, the phosphorescent substance is preferably an organometallic complex expressed by the general formula (104).

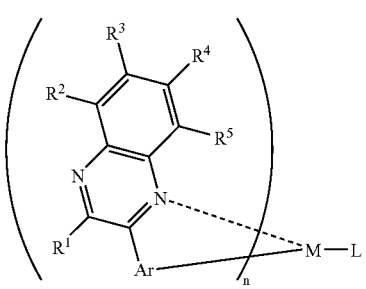

(104)

(in the formula, $R^1$ to $R^5$ each represent any one of hydrogen, a halogen element, an acyl group, an alkyl group, an alkoxyl group, an aryl group, a cyano group, and a heterocycle group. Ar represents an aryl group or a heterocycle group. M represents an element which belongs to Group 9 or Group 10. When M is a Group 9 element, n=2 is satisfied, whereas when M is a Group 10 element, n=1 is satisfied. L represents any one of a monoanionic ligand having a beta-diketone structure, a monoanionic bidentate chelate ligand having a carboxyl group, and a monoanionic bidentate chelate ligand having a phenol hydroxyl group.)

Specifically, the phosphorescent substance is preferably an organometallic complex expressed by the general formula (105).

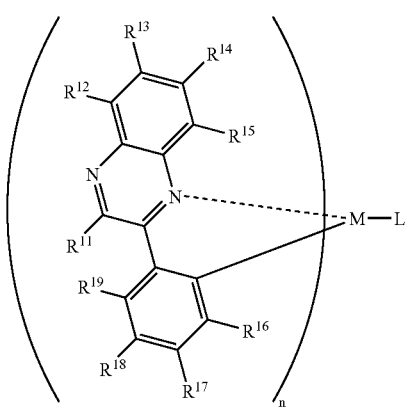

(105)

(in the formula, $R^{11}$ represents any one of alkyl groups having 1 to 4 carbon atoms. $R^{12}$ to $R^{15}$ each represent any one of hydrogen, a halogen element, an acyl group, an alkyl group, an alkoxyl group, an aryl group, a cyano group, and a heterocycle group. Further, $R^{16}$ to $R^{19}$ each represent any one of hydrogen, an acyl group, an alkyl group, an alkoxyl group, an aryl group, a heterocycle group, and an electron-withdrawing substituent. M represents an element which belongs to Group 9 or Group 10. When M is a Group 9 element, n=2 is satisfied, whereas when M is a Group 10 element, n=1 is satisfied. L represents any one of a monoanionic ligand having a beta-diketone structure, a monoanionic bidentate chelate ligand having a carboxyl group, and a monoanionic bidentate chelate ligand having a phenol hydroxyl group.)

Further, specifically, the phosphorescent substance is preferably an organometallic complex expressed by the general formula (106).

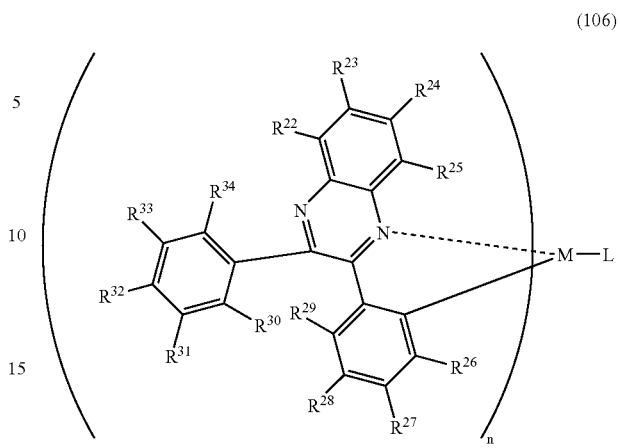

(106)

(in the formula, $R^{22}$ to $R^{34}$ each represent any one of hydrogen, a halogen element, an acyl group, an alkyl group, an alkoxyl group, an aryl group, a cyano group, a heterocycle group, and an electron-withdrawing substituent. M represents an element which belongs to Group 9 or Group 10. When M is a Group 9 element, n=2 is satisfied, whereas when M is a Group 10 element, n=1 is satisfied. L represents any one of a monoanionic ligand having a beta-diketone structure, a monoanionic bidentate chelate ligand having a carboxyl group, and a monoanionic bidentate chelate ligand having a phenol hydroxyl group.)

Further, it is preferable that in the aforementioned structure, a light emission spectrum of the phosphorescent substance have a peak at 560 nm to 700 nm.

The light emitting device of the invention has: a light emitting element in which a layer containing a light emitting substance is provided between a pair of electrodes and the layer containing a light emitting substance has the aforementioned quinoxaline derivative; and a control means for controlling light emission of the light emitting element. It is to be noted that a light emitting device in this specification refers to an image displaying device or a light source (including a lighting system). In addition, a light emitting device also refers to a module in which a connector such as an FPC (Flexible Printed Circuit), a TAB (Tape Automated Bonding) tape, or a TCP (Tape Carrier Package) is attached to a panel, a module in which a printed wiring board is mounted on the tip of a TAB tape or a TCP, or a module in which an IC (integrated circuit) is directly mounted on a light emitting element by COG (Chip On Glass).

Further, an electronic appliance using the light emitting element of the invention for a display portion is in the category of the invention. Therefore, the electronic appliance of the invention has a display portion provided with the light emitting element and the control means for controlling light emission of the light emitting element.

The quinoxaline derivative of the invention is bipolar and excellent in both an electron transporting property and a hole transporting property. Further, the quinoxaline derivative of the invention has a high glass transition point and excellent heat resistance. Furthermore, the quinoxaline derivative of the invention is stabilized with respect to electrochemical oxidation or reduction.

By using the quinoxaline derivative of the invention, which is bipolar, a light emitting element and a light emitting device which require a low driving voltage and consume low power can be obtained.

Further, by using the quinoxaline derivative of the invention, which has a high glass transition point, a light emitting element and a light emitting device which have high heat resistance can be obtained.

Further, by using the quinoxaline derivative of the invention, which is stabilized with respect to electrochemical oxidation or reduction, a light emitting element and a light emitting device which have a long life can be obtained.

Further, by using the quinoxaline derivative of the invention, a long-life electronic appliance which consumes low power and has high heat resistance can be obtained.

BEST MODE FOR CARRYING OUT THE INVENTION

Figure 1A:
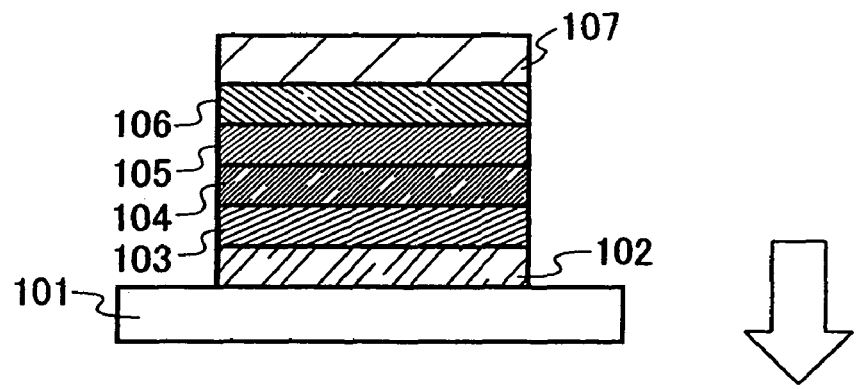
FIGS. 1A to 1C are views each showing a light emitting element of the invention.

Although the invention will be fully described by way of embodiment modes and embodiments with reference to the accompanying drawings, it is to be understood that various changes and modifications will be apparent to those skilled in the art. Therefore, unless such changes and modifications depart from the scope of the invention, they should be construed as being included therein.

Embodiment Mode 1

The quinoxaline derivative of the invention is expressed by the following general formula (1).

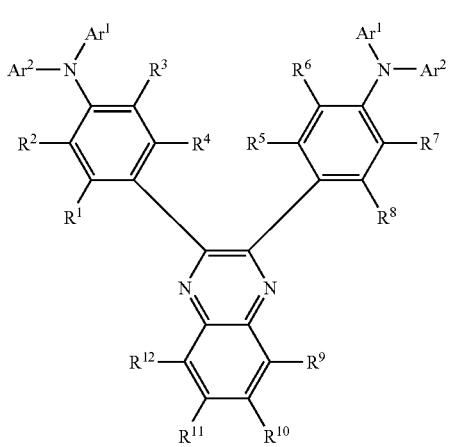

(1)

(in the formula, $R^1$ to $R^{12}$ may be the same or different and each represent any one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group. $R^9$, $R^{10}$, and $R^{11}$ may be combined with $R^{10}$, $R^{11}$, and $R^{12}$ respectively to form a condensed ring. $Ar^1$ represents a substituted or unsubstituted biphenyl group or a substituted or unsubstituted terphenyl group. $Ar^2$ represents a substituted or unsubstituted phenyl group, a substituted or unsubstituted biphenyl group, a substituted or unsubstituted terphenyl group, or a substituted or unsubstituted monocyclic heterocycle group.)

In the general formula (1), each of the substituted biphenyl group, the substituted terphenyl group, and the substituted monocyclic heterocycle group preferably has an alkyl group or a phenyl group as the substituent. As the alkyl group, a methyl group, an ethyl group, an isopropyl group, a tert-butyl group, and the like are cited.

In particular, the quinoxaline derivative of the invention is preferably the one expressed by the following general formula (2).

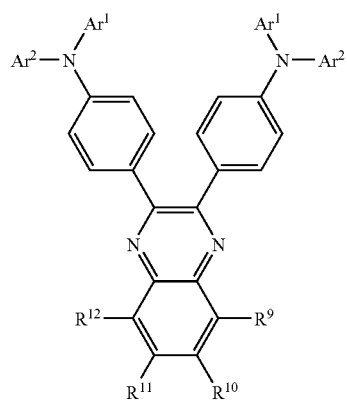

(2)

(in the formula, $R^9$ to $R^{12}$ may be the same or different and each represent any one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group. $R^9$, $R^{10}$, and $R^{11}$ may be combined with $R^{10}$, $R^{11}$, and $R^{12}$ respectively to form a condensed ring. $Ar^1$ represents a substituted or unsubstituted biphenyl group or a substituted or unsubstituted terphenyl group. $Ar^2$ represents a substituted or unsubstituted phenyl group, a substituted or unsubstituted biphenyl group, a substituted or unsubstituted terphenyl group, or a substituted or unsubstituted monocyclic heterocycle group.)

Further, in particular, the quinoxaline derivative of the invention is preferably the one expressed by the following general formula (3).

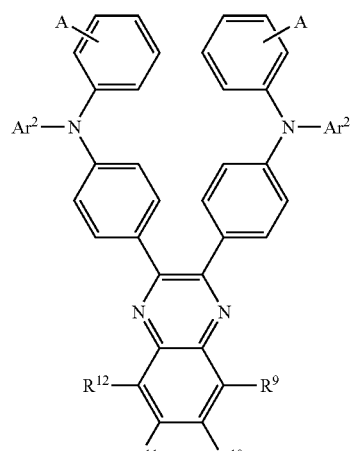

(3)

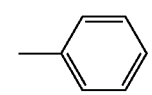

(4)

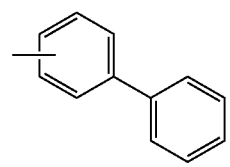

(5)

(in the formula, $R^9$ to $R^{12}$ may be the same or different and each represent any one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group. $R^9$, $R^{10}$, and $R^{11}$ may be combined with $R^{10}$, $R^{11}$, and $R^{12}$ respectively to form a condensed ring. A represents a substituent expressed by the structure formula (4) or the structure formula (5). $Ar^2$ represents a substituted or unsubstituted phenyl group, a substituted or unsubstituted biphenyl group, a substituted or unsubstituted terphenyl group, or a substituted or unsubstituted monocyclic heterocycle group.)

Further, in particular, the quinoxaline derivative of the invention is preferably the one expressed by the following general formula (6).

(6)

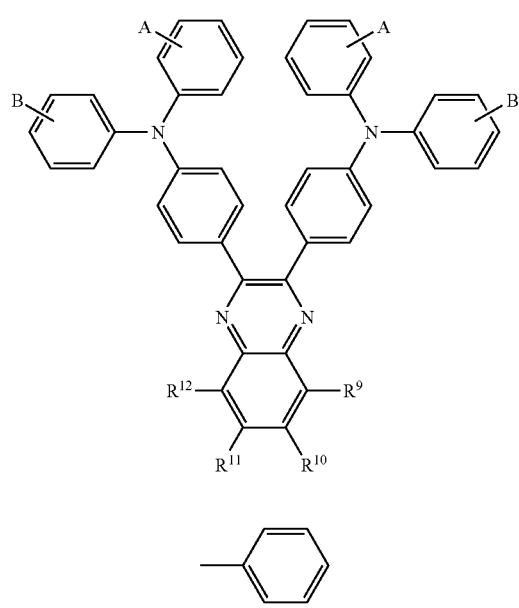

Further, in particular, the quinoxaline derivative of the invention is preferably the one expressed by the following general formula (9).

(9)

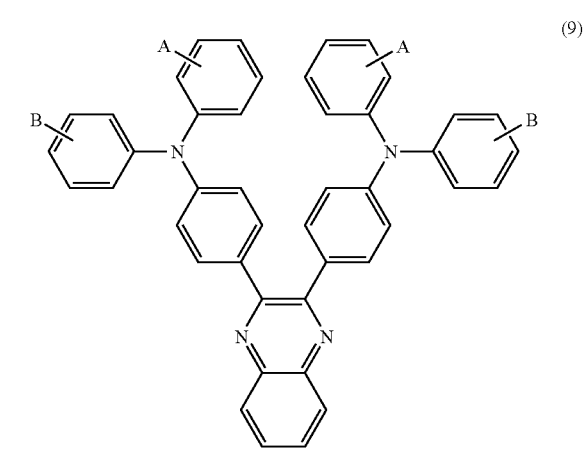

(7)

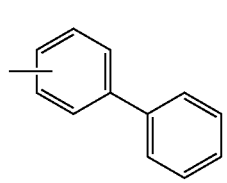

(8)

(10)

(11)

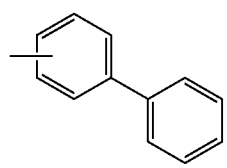

(in the formula, $R^9$ to $R^{12}$ may be the same or different and each represent any one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group. $R^9$, $R^{10}$, and $R^{11}$ may be combined with $R^{10}$, $R^{11}$, and $R^{12}$ respectively to form a condensed ring. A represents a substituent expressed by the structure formula (7) or the structure formula (8). B represents a hydrogen atom or a substituent expressed by the structure formula (7) or the structure formula (8).)

(in the formula, A represents a substituent expressed by the structure formula (10) or the structure formula (11), and B represents a hydrogen atom or a substituent expressed by the structure formula (10) or the structure formula (11).)

Further, as a specific example of the quinoxaline derivative of the invention, quinoxaline derivatives expressed by structure formulas (14) to (65) are cited; however, the invention is not limited to them.

(14)

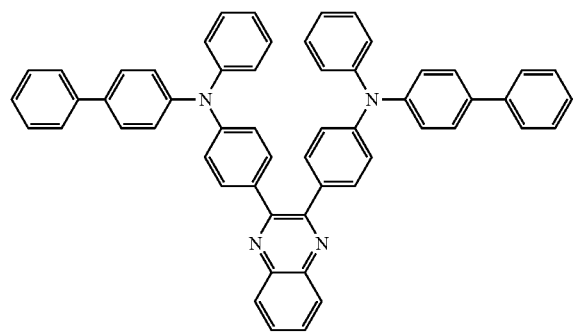

(15)

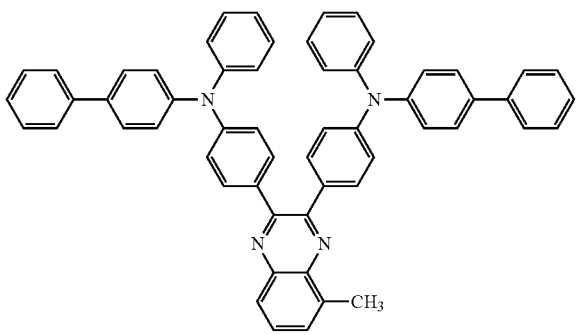

-continued
(16)
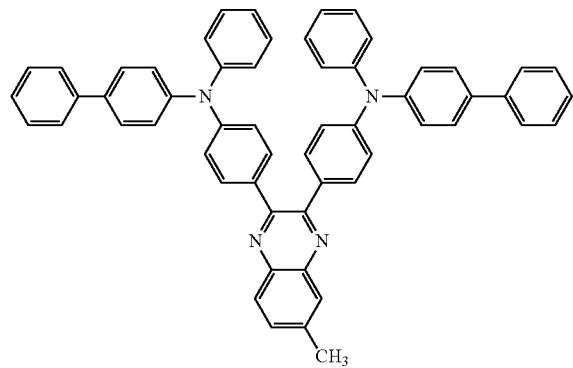
(17)
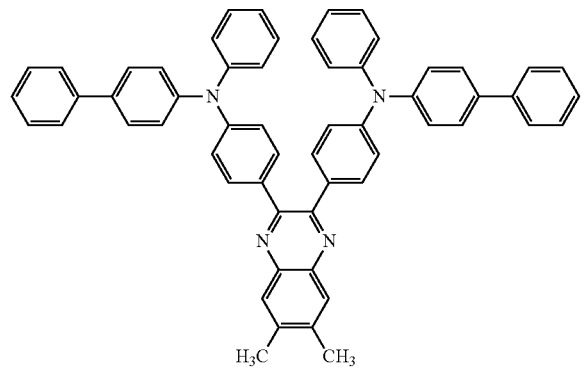
(18)
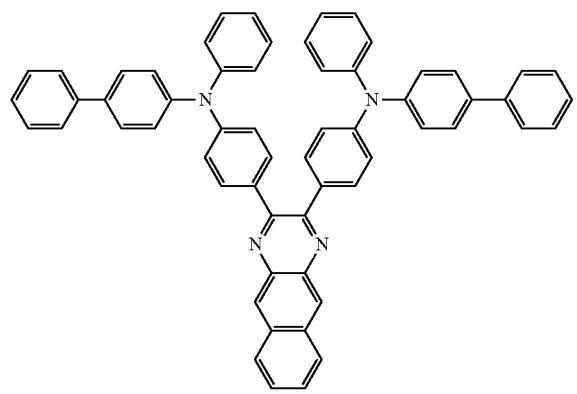
(19)
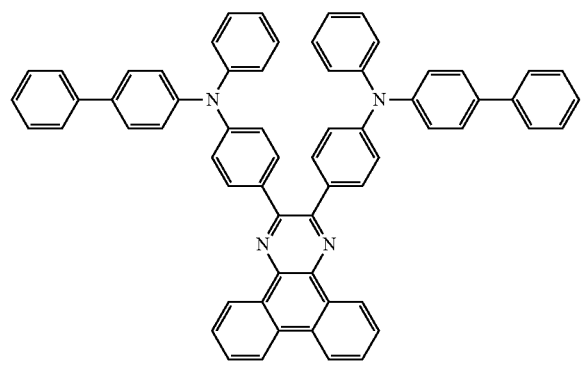
(20)
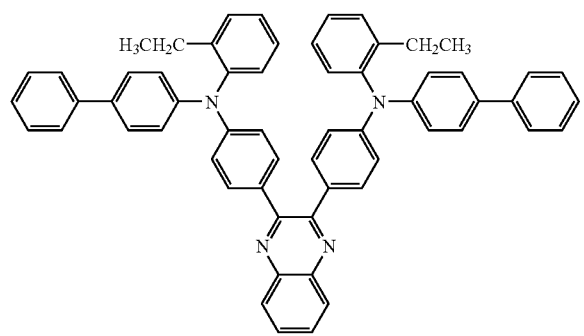
(21)
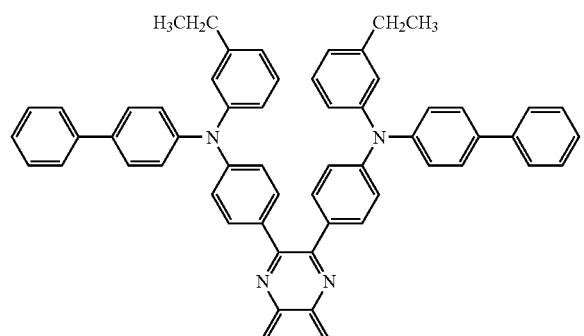
(22)
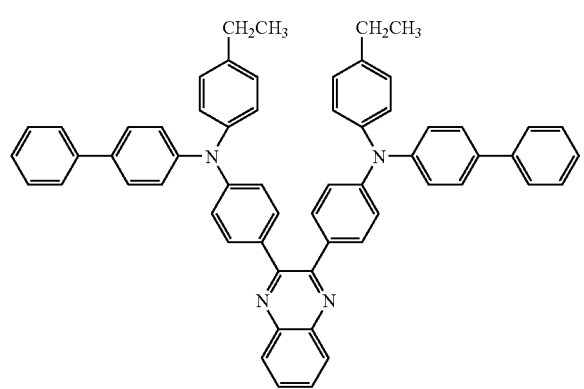
(23)
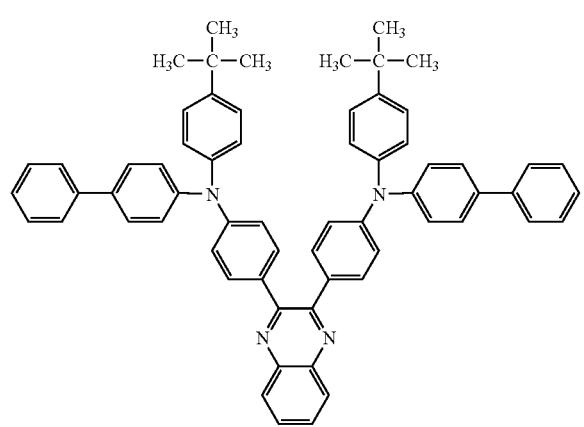

-continued
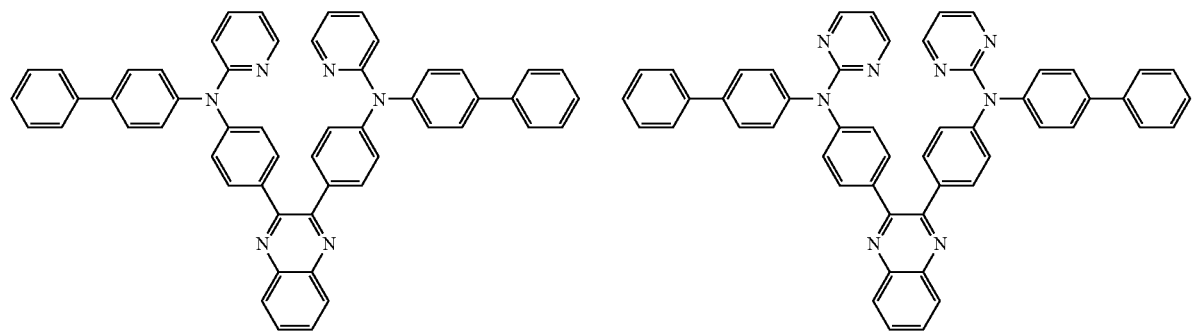
(24) (25)
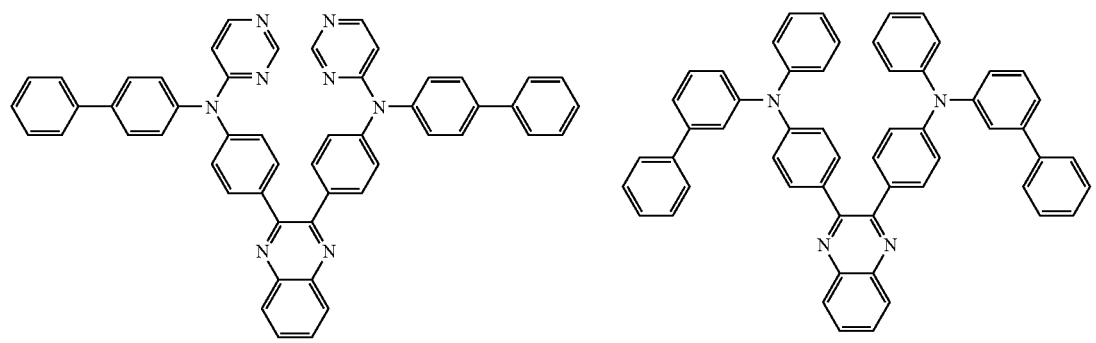
(26) (27)
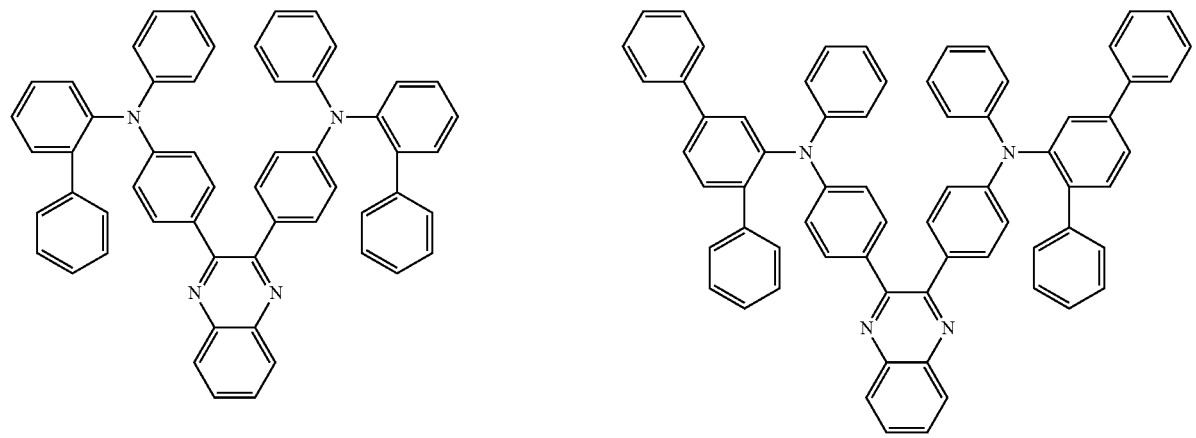
(28) (29)
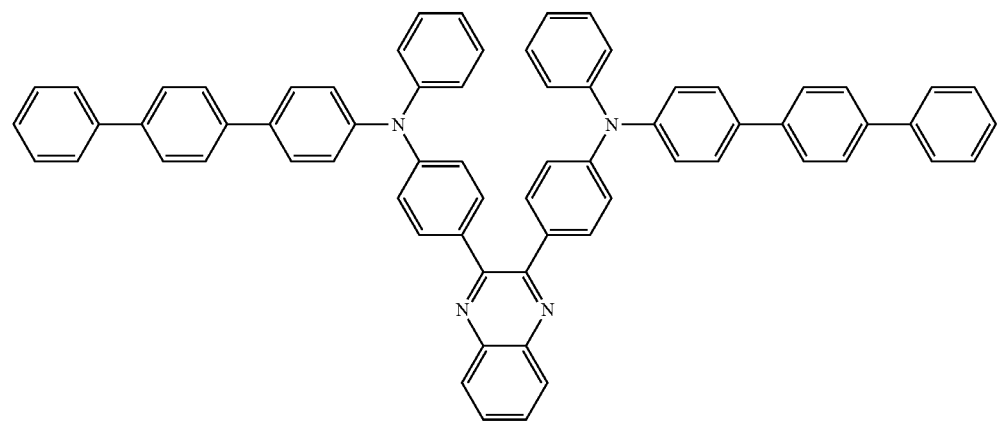
(30)

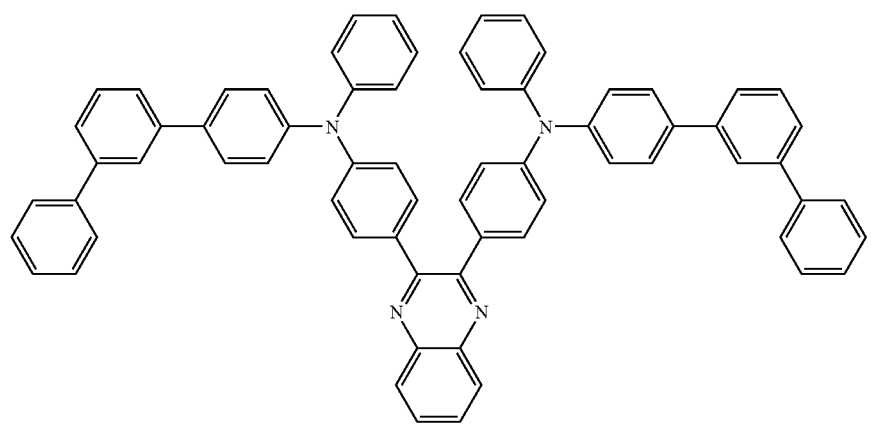
(31)
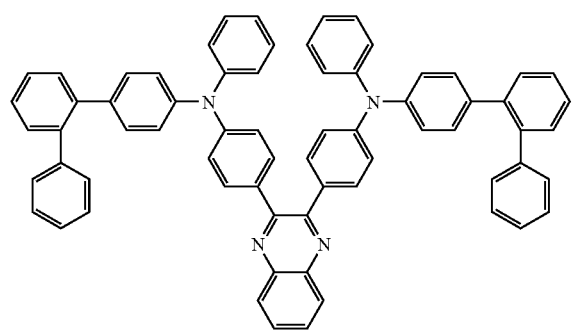
(32)
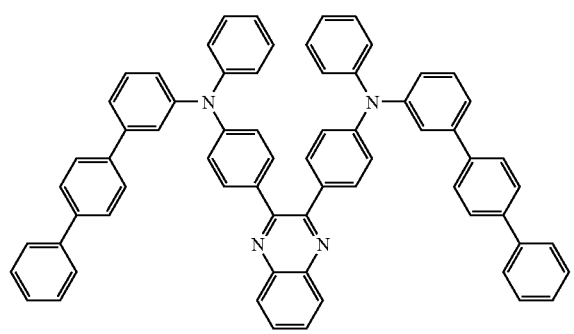
(33)
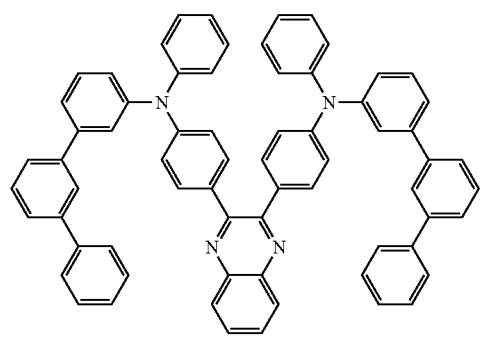
(34)
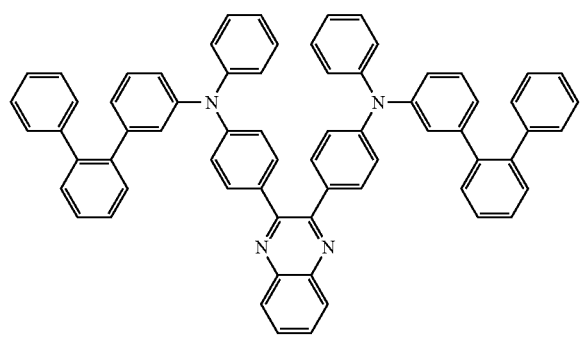
(35)
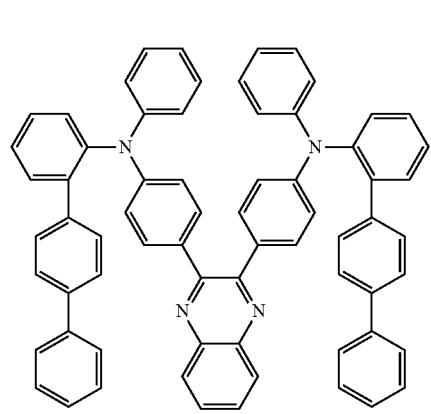
(36)
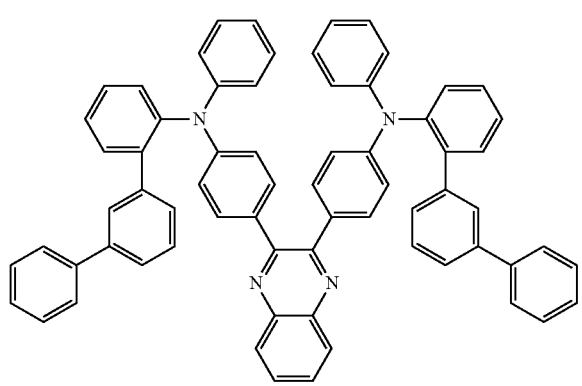
(37)

-continued
(38)
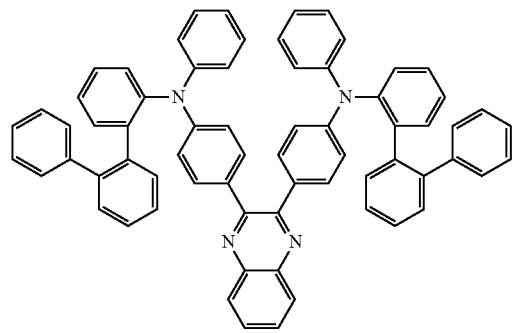
(39)
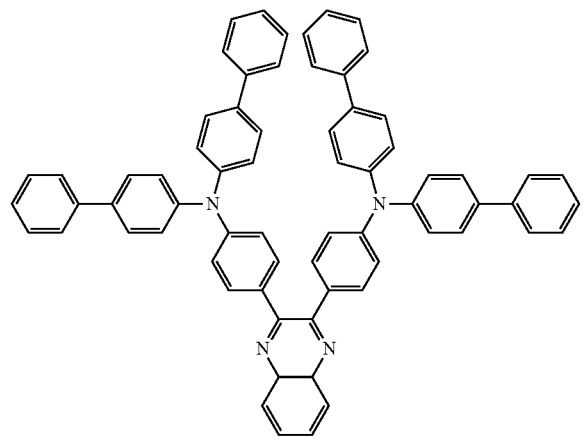
(40)
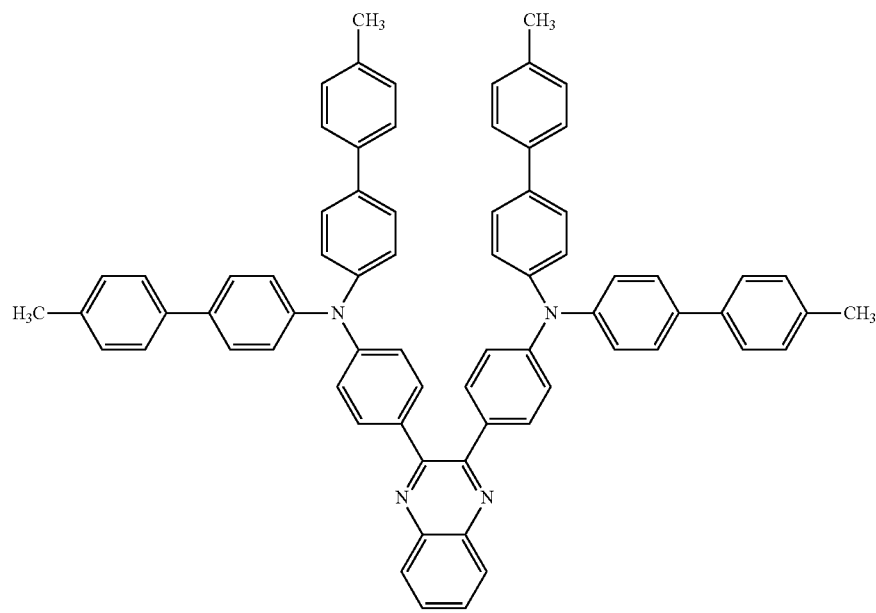
(41)
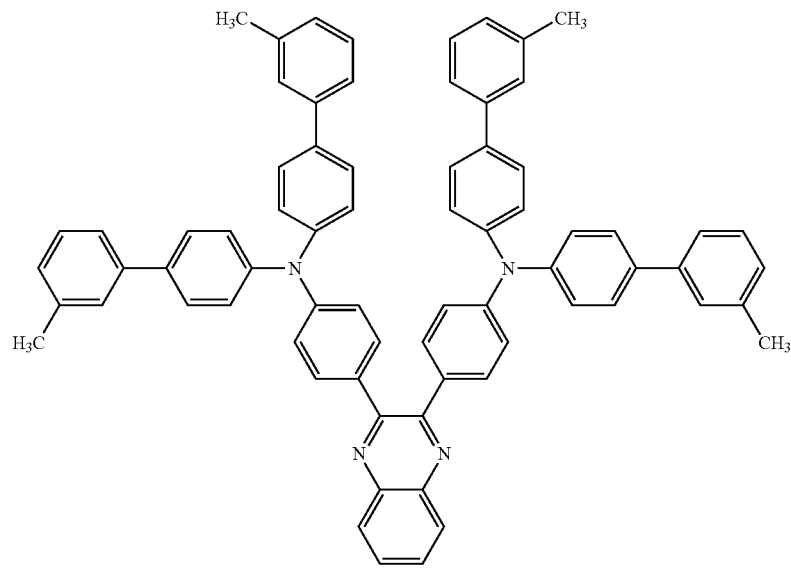

-continued
(42)
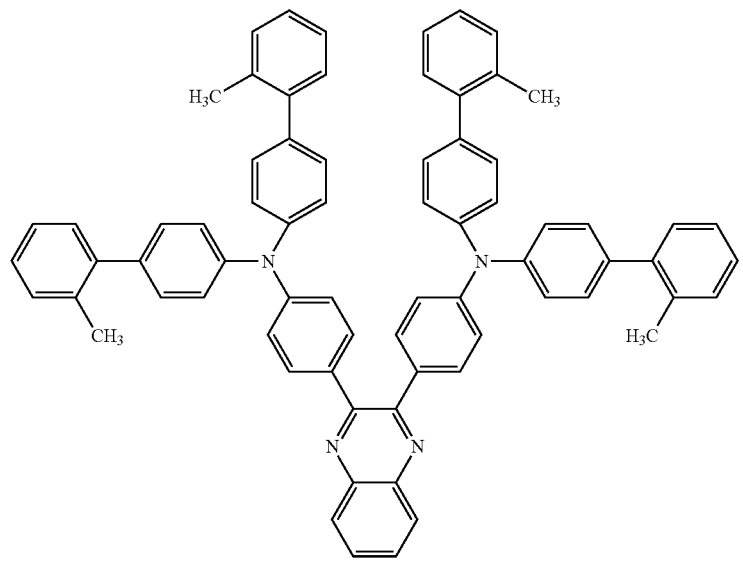
(43)
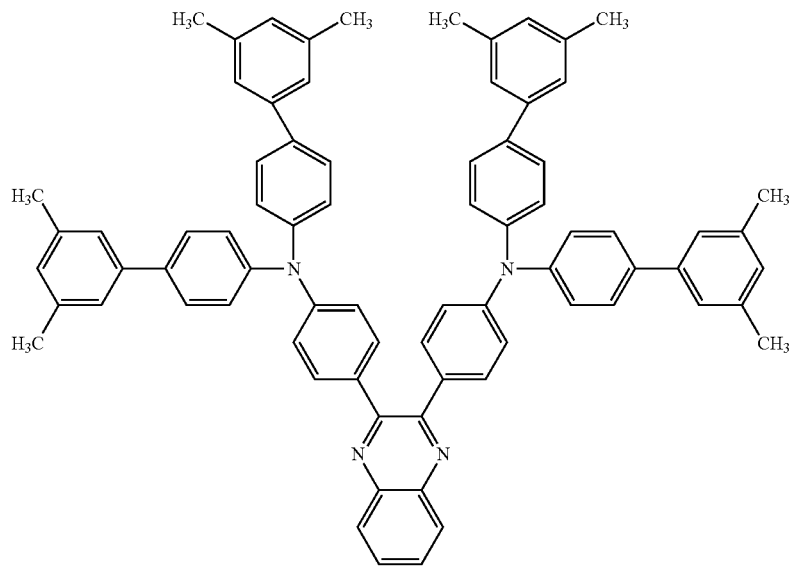
(44)
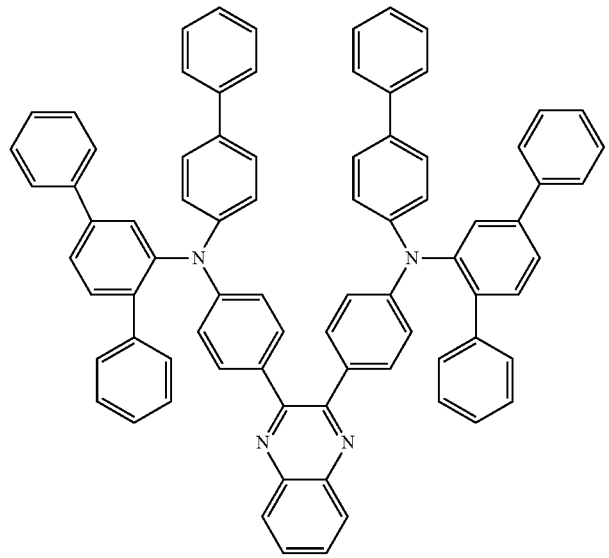

-continued
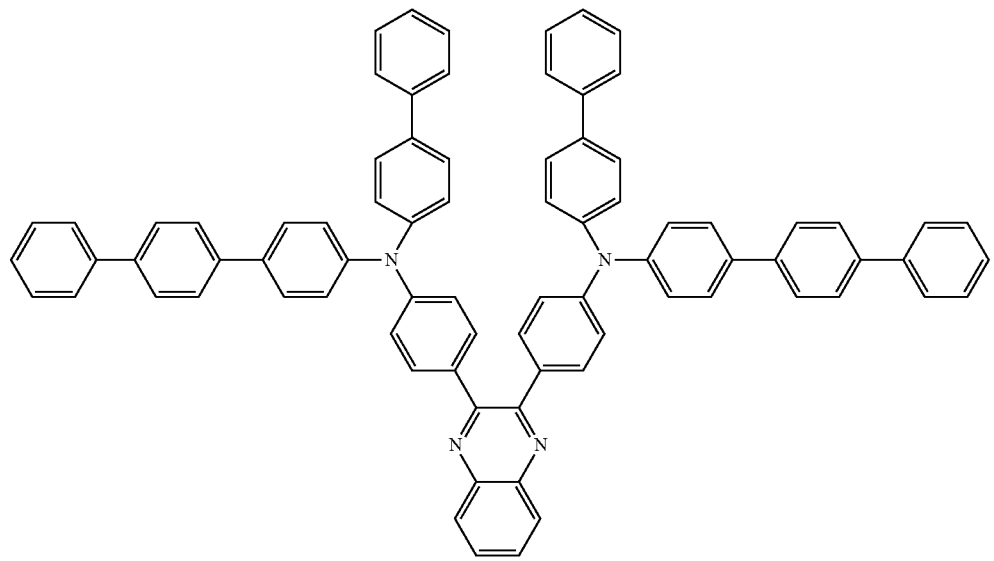
(45)
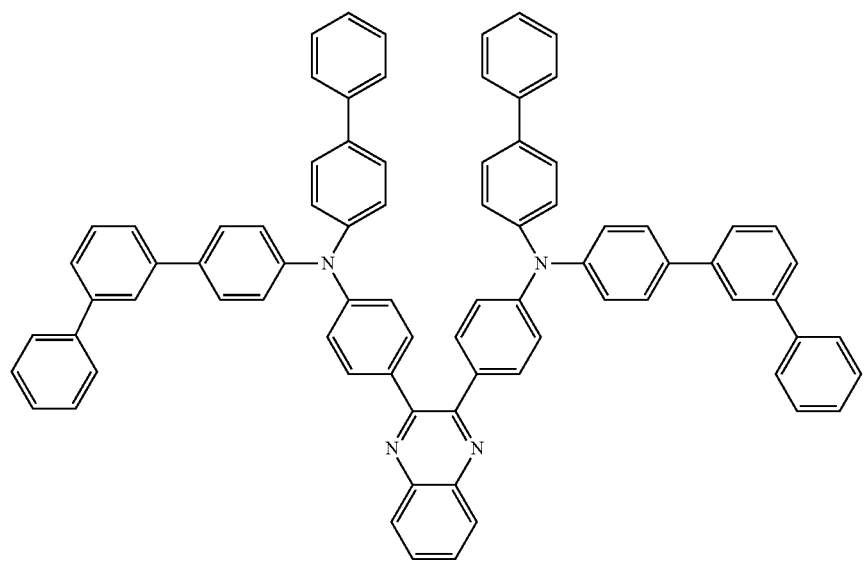
(46)
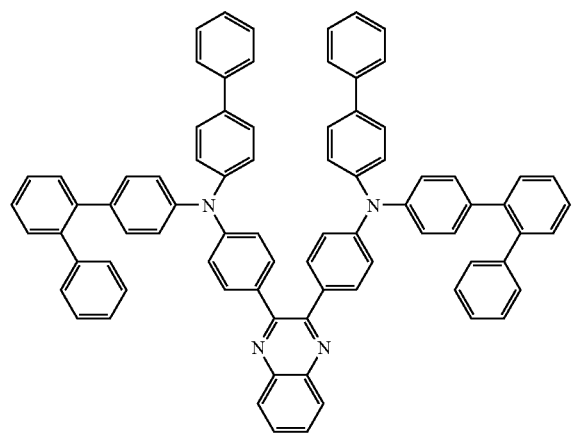
(47)
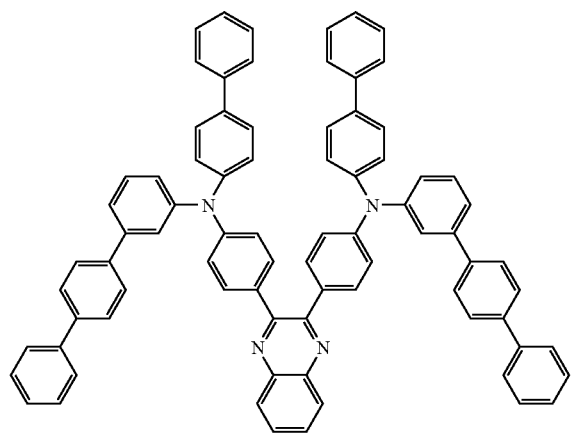
(48)

-continued
(49)
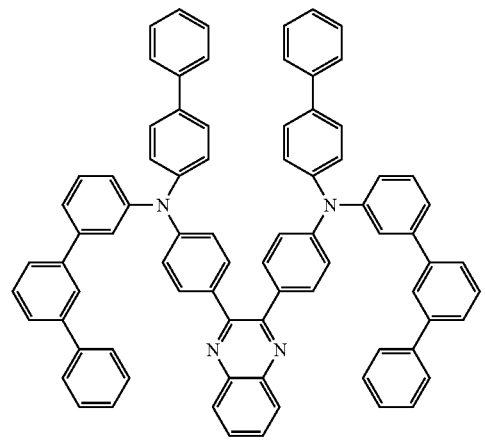
(50)
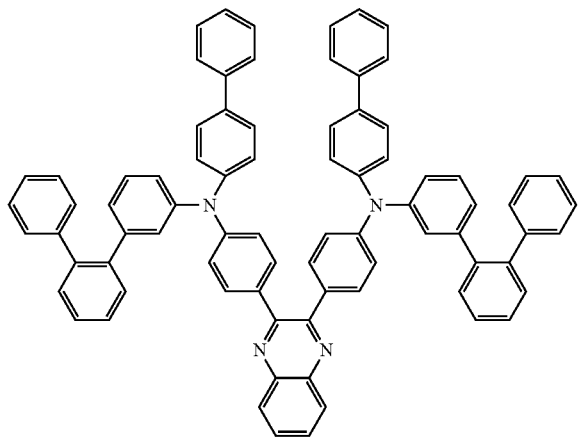
(51)
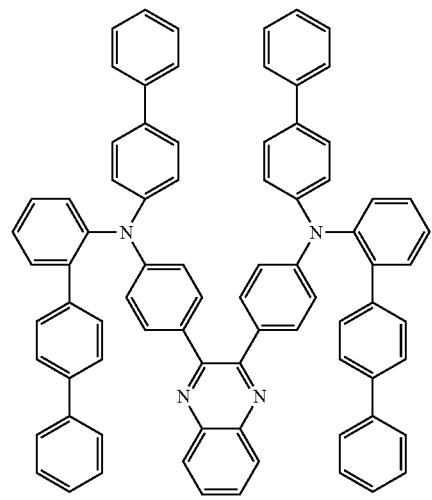
(52)
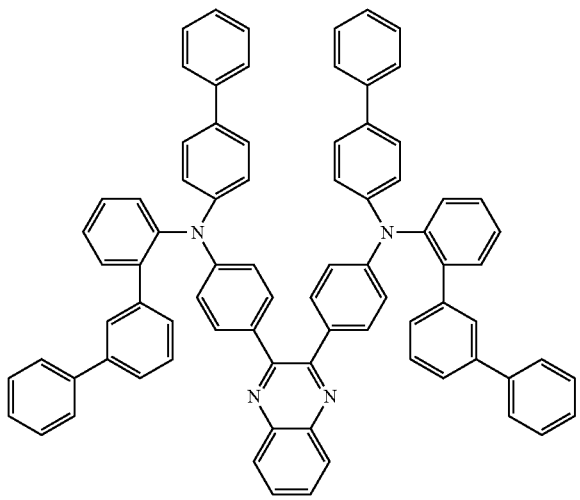
(53)
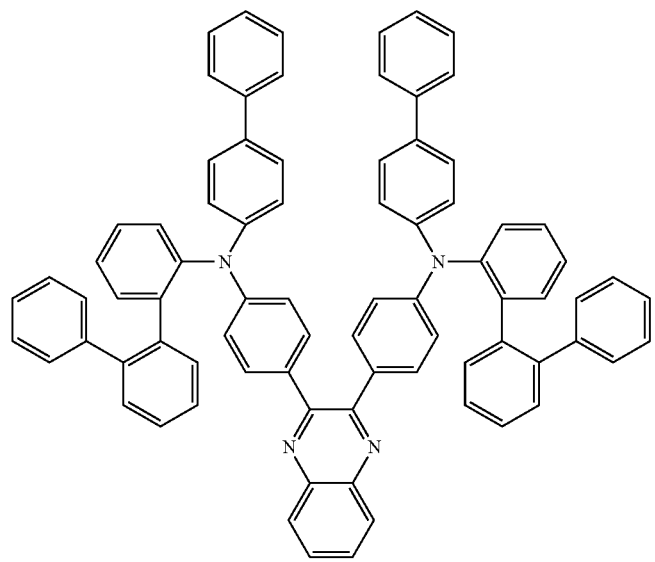

-continued
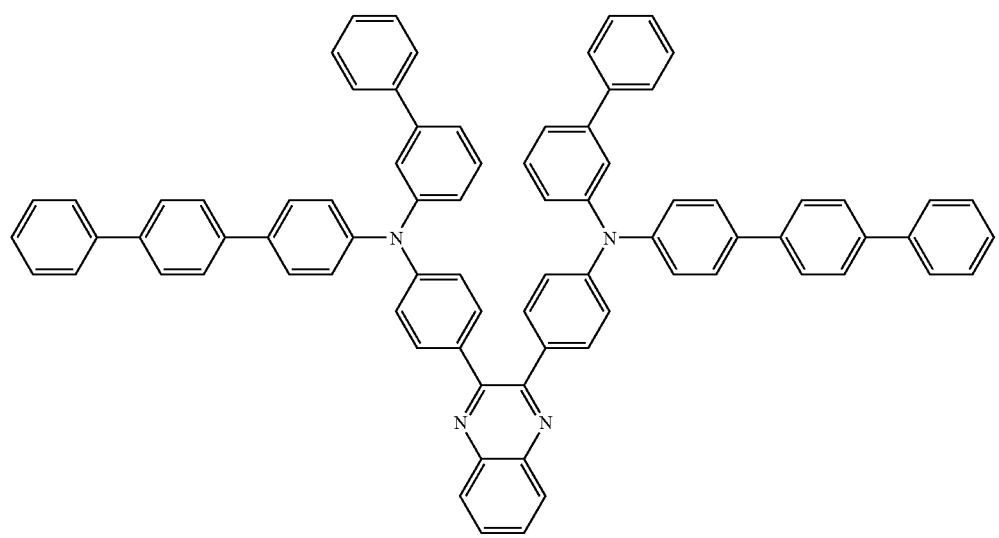
(54)
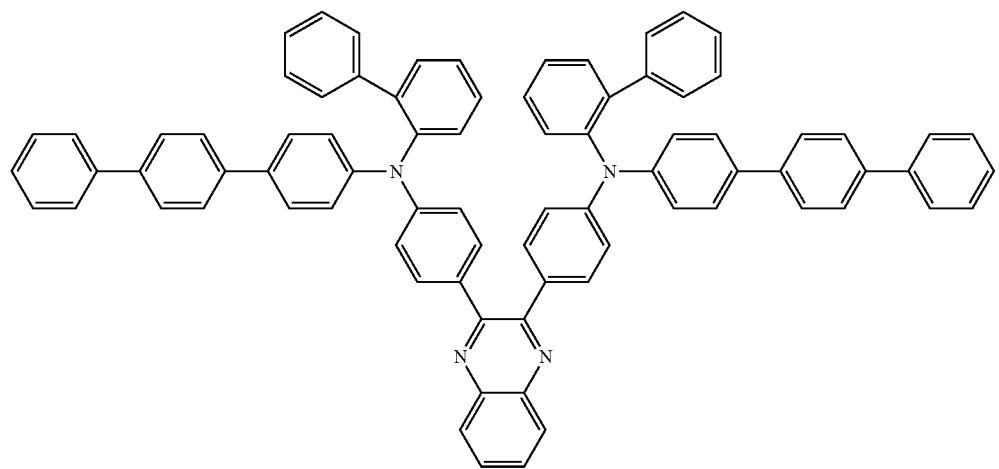
(55)
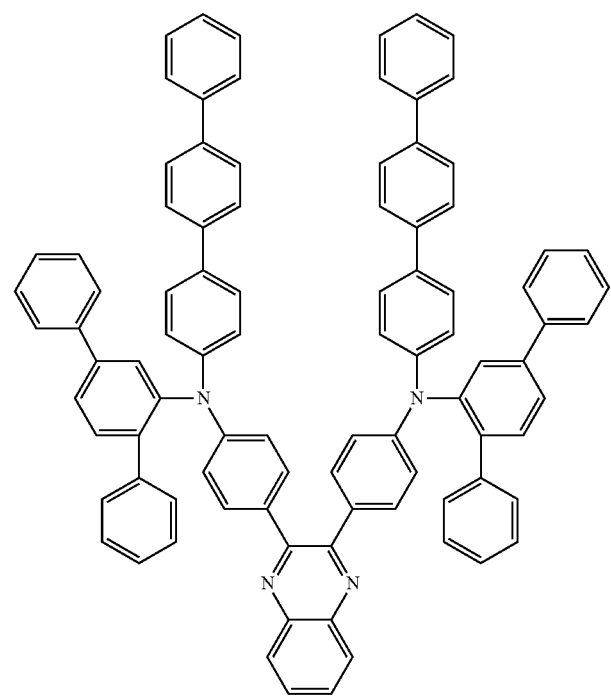
(56)

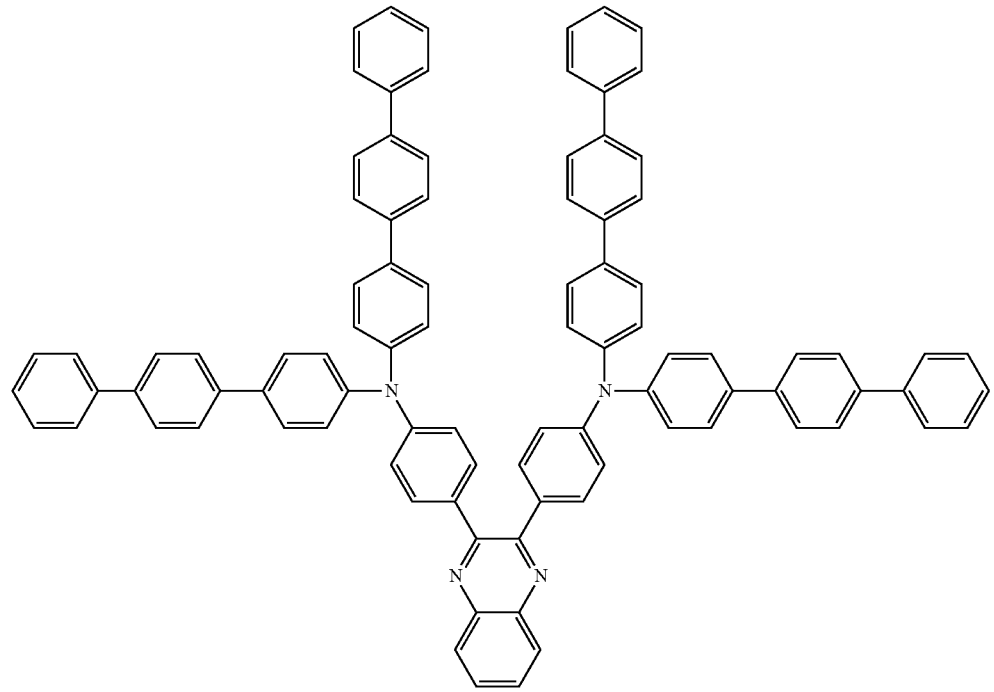
(57)
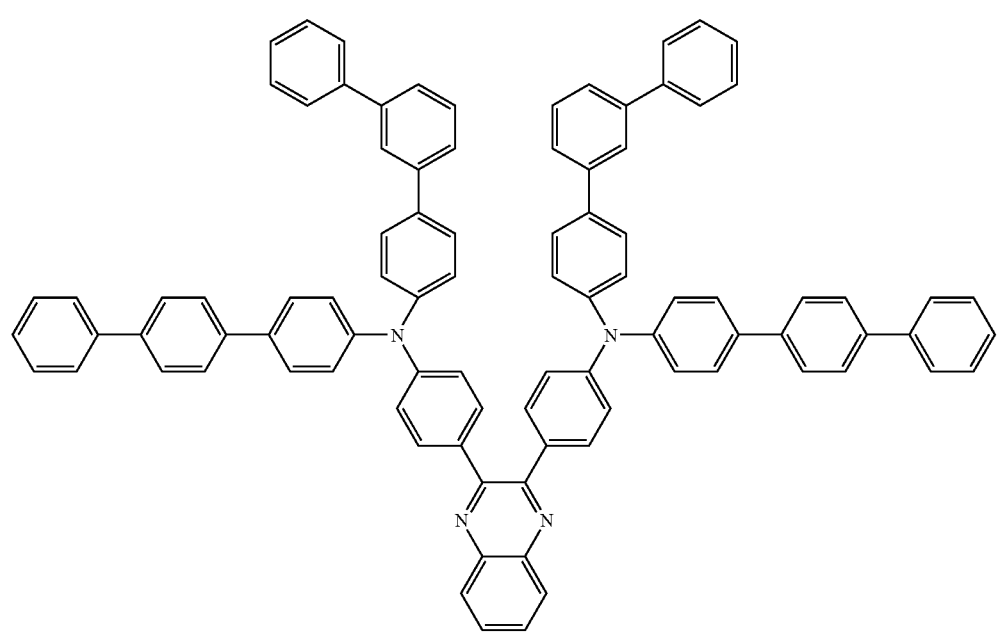
(58)

-continued
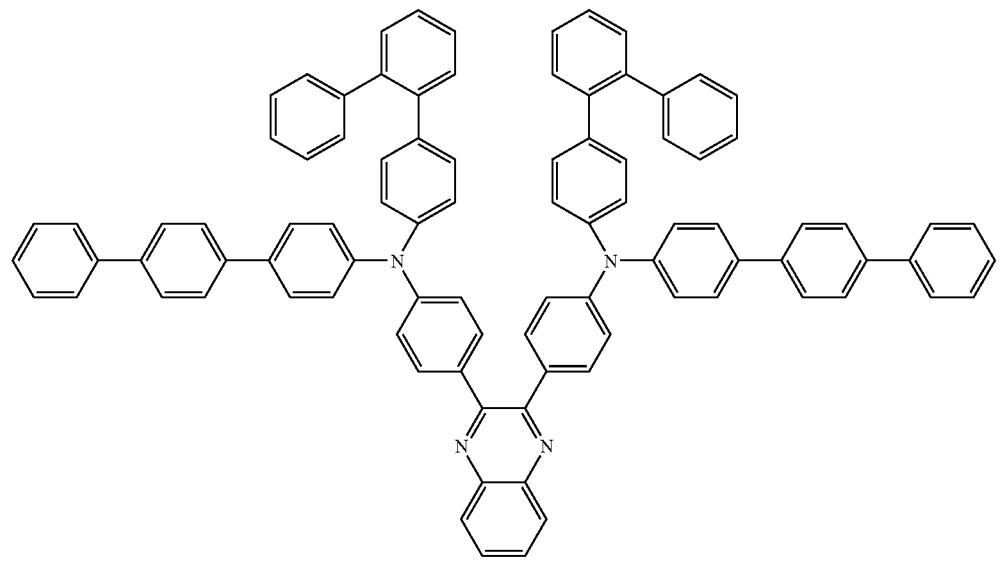
(59)
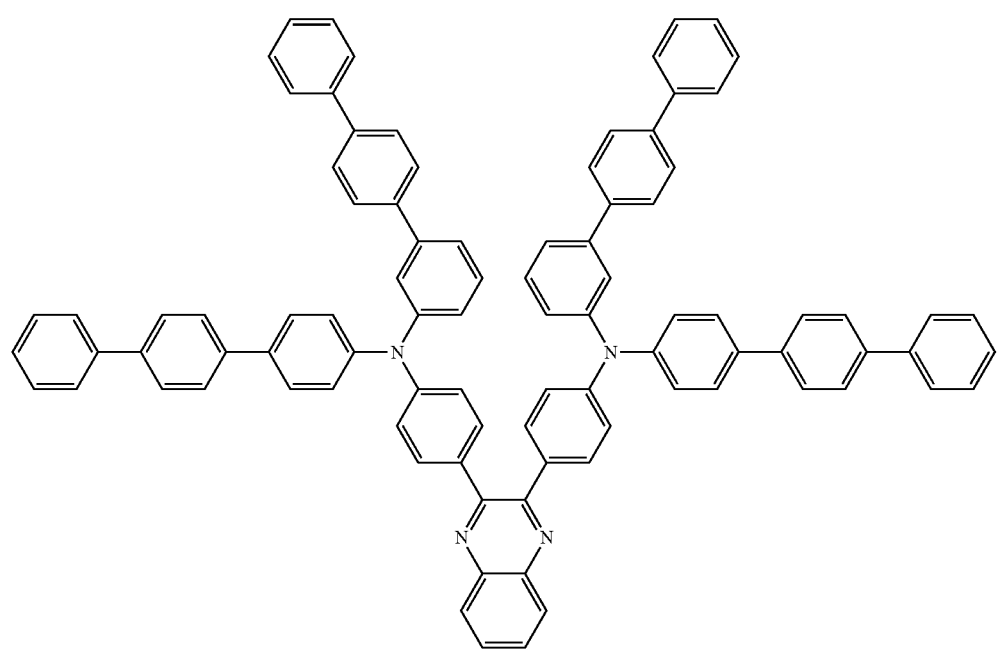
(60)

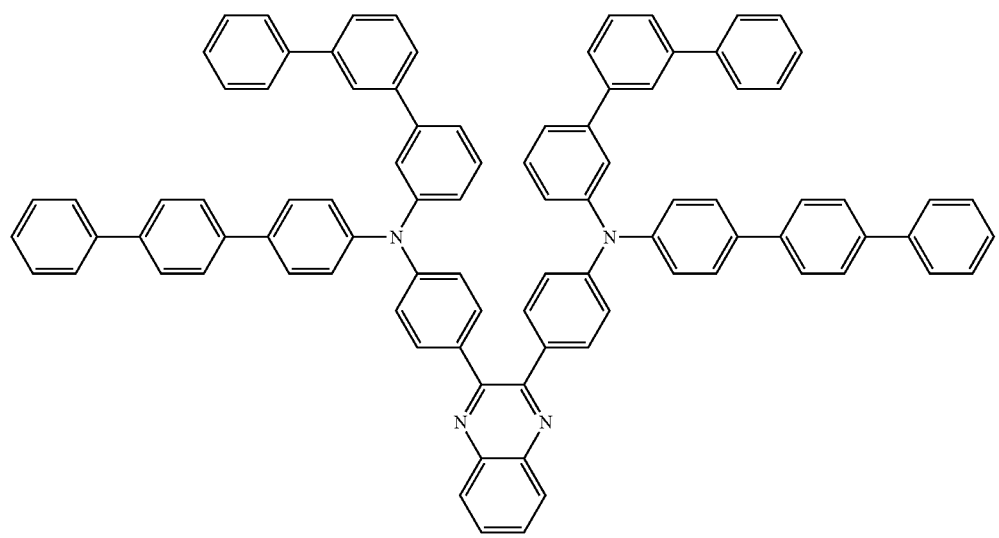
(61)
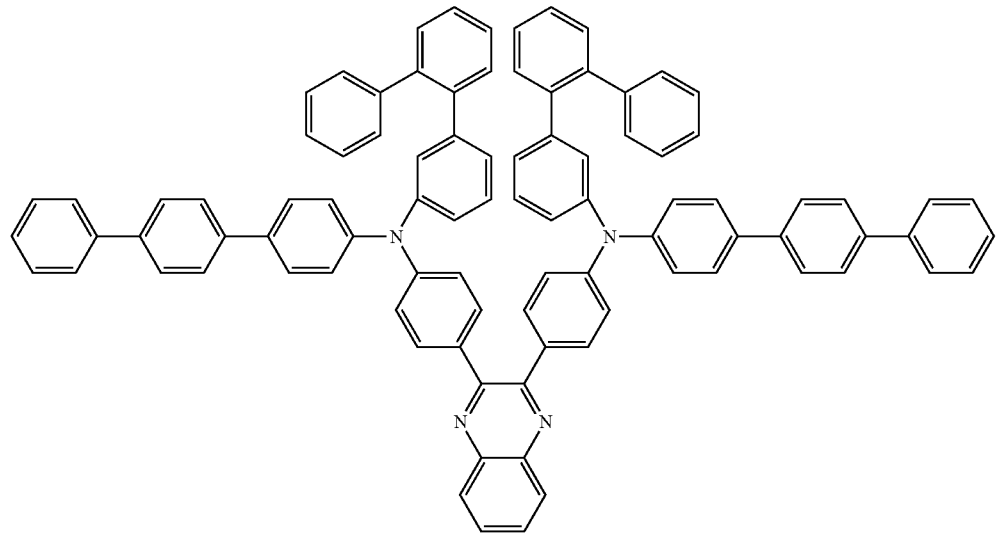
(62)
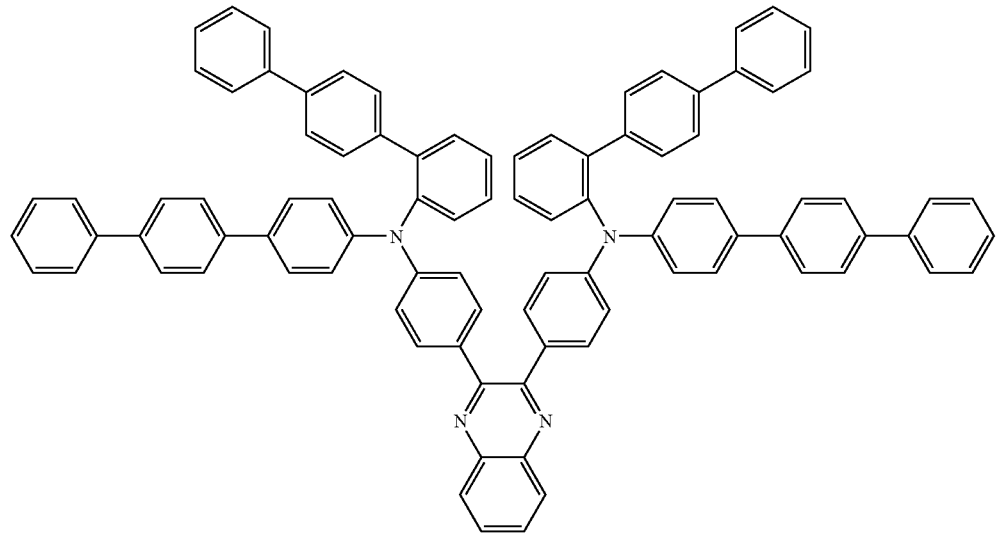
(63)

(64)
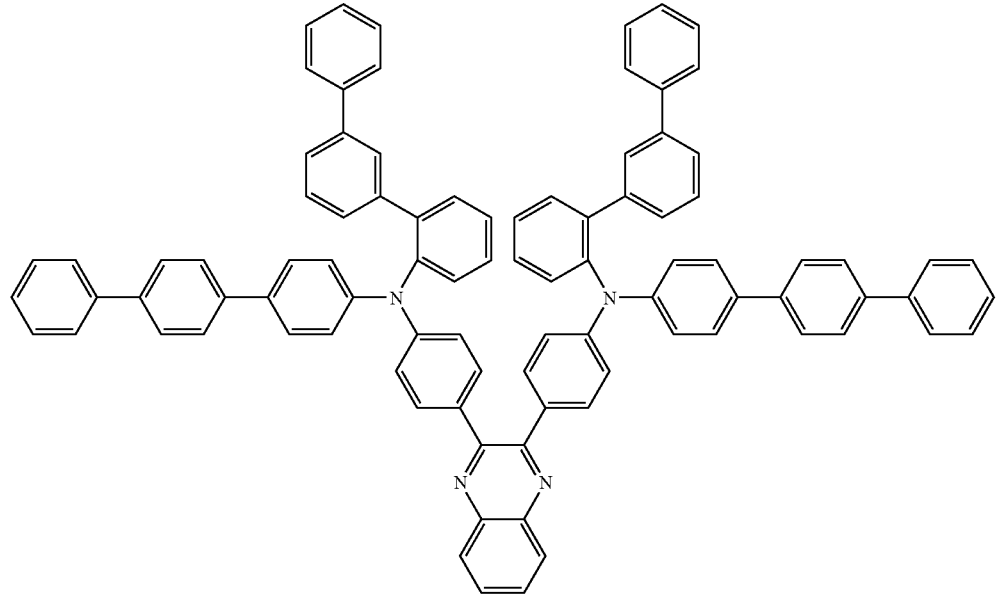
(65)
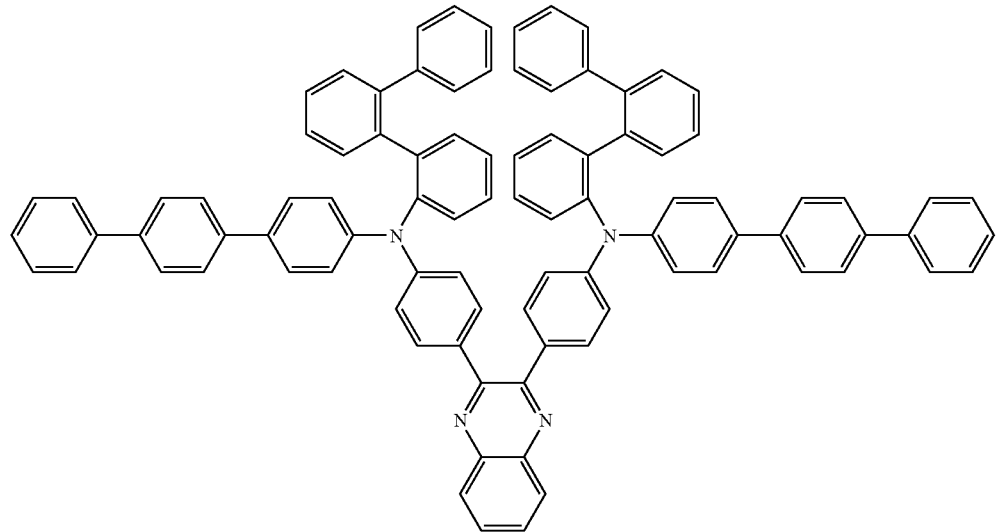
Various reactions can be applied to a synthesizing method of the quinoxaline derivative of the invention. For example, a quinoxaline derivative can be made by a synthetic reaction shown in the following reaction schemes (A-1) and (A-2).
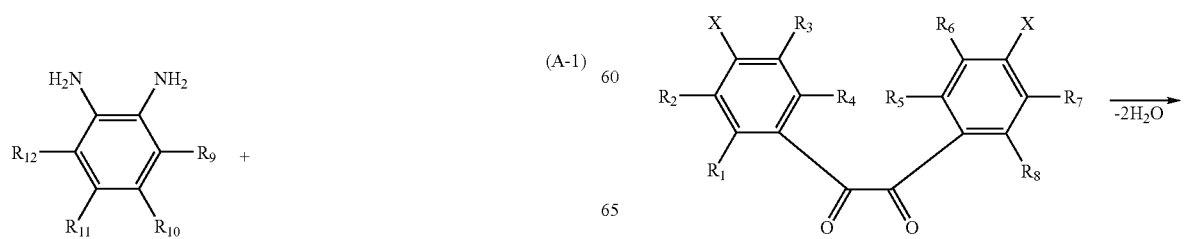

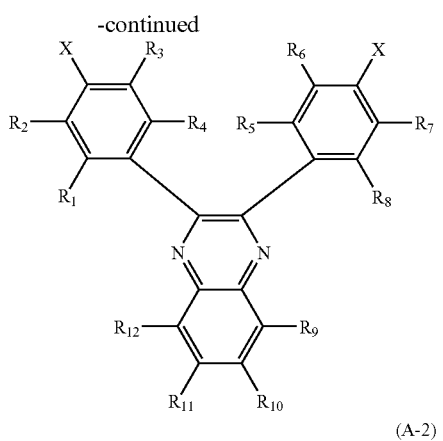

(A-2)

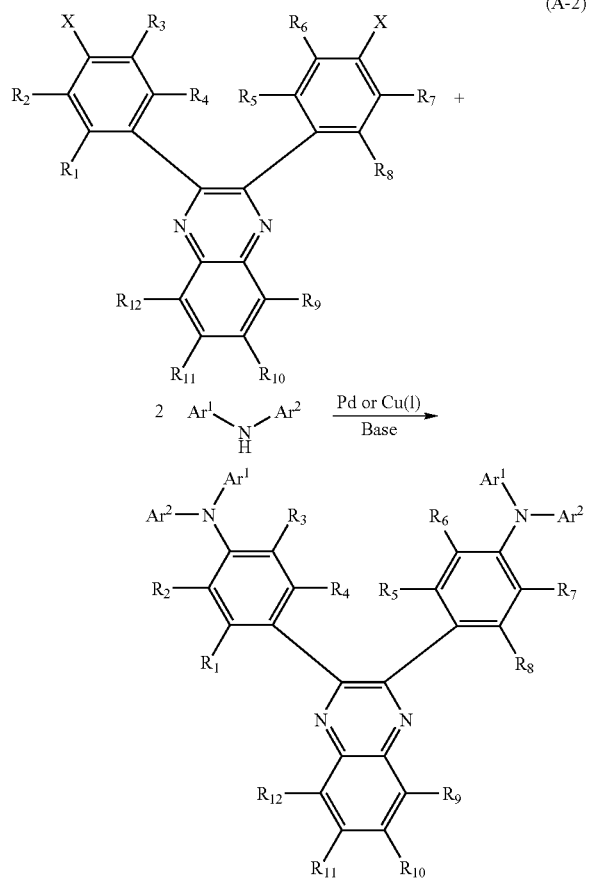

First, a quinoxaline skeleton is formed by a condensation reaction between dibenzil substituted by a halogen atom X and 1,2-diamino benzene. As a halogen atom, bromine, iodine, and chlorine are cited. Considering easiness of handling and appropriate reactivity, bromine is preferable.

A desired quinoxaline derivative of the invention can be synthesized by coupling 2 equivalent diarylamine (Ar$^1$—NH—Ar$^2$) with the obtained halogen-substituted quinoxaline by using a palladium catalyst or monovalent copper in the presence of a base. As the base, an inorganic base such as potassium carbonate or sodium carbonate, an organic base such as a metal alkoxide, or the like can be used. As the palladium catalyst, palladium acetate, palladium chloride, bis(dibenzylidineacetone)palladium, or the like can be used.

It is to be noted that diarylamine (Ar$^1$—NH—Ar$^2$) in the aforementioned scheme can be synthesized by the following scheme, for example.

First, in the case where Ar$^1$ is a biphenyl group, desired aryl amine (Ar$^1$—NH—Ar$^2$; Ar$^1$ is a biphenyl group) can be obtained by coupling 1 equivalent aryl amine (Ar$^2$—NH$_2$) with halogen-substituted biphenyl of which the second position, the third position, or the fourth position is substituted by halogen by using a palladium catalyst or monovalent copper in the presence of a base. As the base, an inorganic base such as potassium carbonate or sodium carbonate, an organic base such as a metal alkoxide, or the like can be used. As the palladium catalyst, palladium acetate, palladium chloride, bis(dibenzylidineacetone)palladium, or the like can be used.

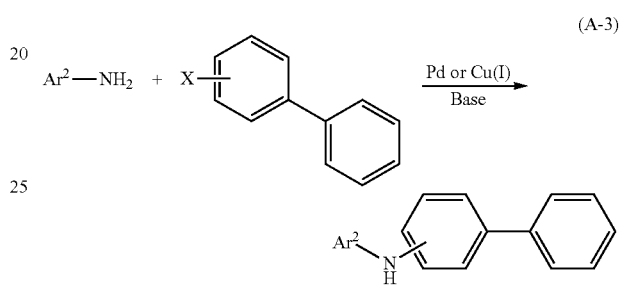

(A-3)

Further, in the case where both Ar$^1$ and Ar$^2$ are biphenyl groups, desired aryl amine (Ar$^1$—NH—Ar$^2$; both Ar$^1$ and Ar$^2$ are biphenyl groups) can be obtained by coupling 2 equivalent phenyl boron acid with diphenylamine in which two phenyl groups are halogen-substituted by using a palladium catalyst or a nickel catalyst in the presence of a base, as shown in the following synthetic scheme (A-4). As the base, an inorganic base such as potassium carbonate or sodium carbonate, an organic base such as a metal alkoxide, or the like can be used. As the palladium catalyst, palladium acetate, palladium chloride, bis(dibenzylidineacetone)palladium, or the like can be used. This method has an advantage that N,N-di(4-biphenylyl)amine can be synthesized without using 4-aminobiphenyl which is a harmful substance to human body.

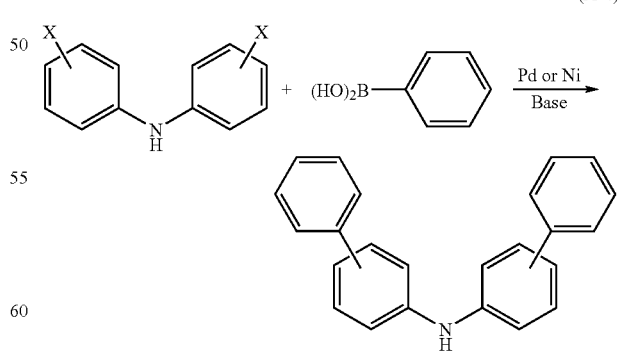

(A-4)

On the other hand, in the case where aryl amine (Ar$^1$—NH—Ar$^2$) in which Ar$^1$ is a terphenyl group is synthesized, various terphenyl amines of which substituted positions are different can be synthesized by coupling 1 equivalent biphenyl boron acid of which the second position, the third position, or the fourth position is substituted by a boronic acid group with aniline of which the second position, the third position, or the fourth position is halogen-substituted by using a palladium catalyst or a nickel catalyst in the presence of a base, as shown in the following synthetic scheme (A-5). Then, desired aryl amine ($Ar^1$—NH—$Ar^2$; $Ar^1$ is a terphenyl group) can be obtained by coupling the obtained 1 equivalent terphenyl amine with halogen-substituted arene ($Ar^2$—X) by using a palladium catalyst or monovalent copper in the presence of a base, as shown in the following synthetic scheme (A-6). As the base, an inorganic base such as potassium carbonate or sodium carbonate, an organic base such as a metal alkoxide, or the like can be used. As the palladium catalyst, palladium acetate, palladium chloride, bis(dibenzylidineacetone)palladium, or the like can be used.

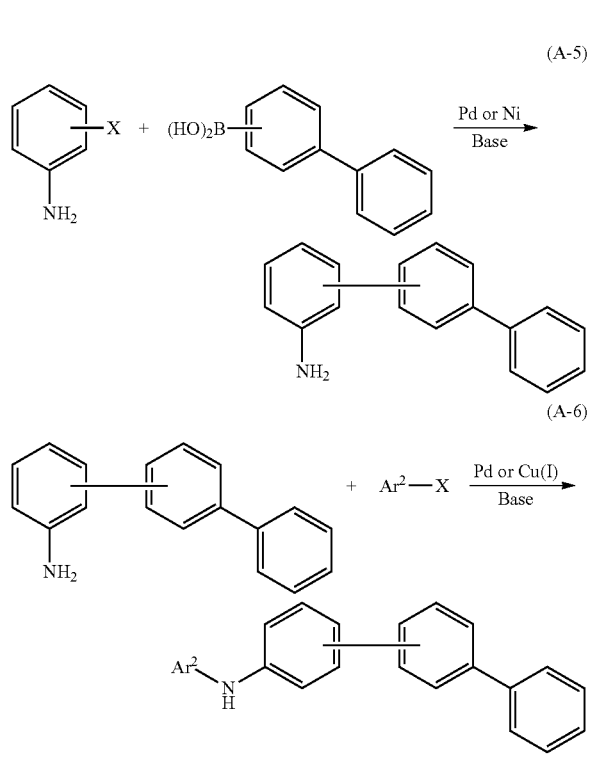

(A-5)

(A-6)

Further, in the case where $Ar^1$ is a terphenyl group and a center benzene ring of the terphenyl group is substituted by an amino group, aniline which is substituted by two halogen atoms is coupled with 2 equivalent phenyl boron acid by using a palladium catalyst or nickel catalyst in the presence of a base as shown in the following synthetic scheme (A-7), then, a terphenyl amine which is a terphenyl group substituted by an amino group in a center benzene ring of the terphenyl group. Then, desired aryl amine ($Ar^1$—NH—$Ar^2$; $Ar^1$ is a terphenyl group) can be obtained by coupling the obtained 1 equivalent terphenyl amine with halogen-substituted arene ($Ar^2$—X) by using a palladium catalyst or monovalent copper in the presence of a base, as shown in the following synthetic scheme (A-8). As the base, an inorganic base such as potassium carbonate or sodium carbonate, an organic base such as a metal alkoxide, or the like can be used. As the palladium catalyst, palladium acetate, palladium chloride, bis(dibenzylidineacetone)palladium, or the like can be used.

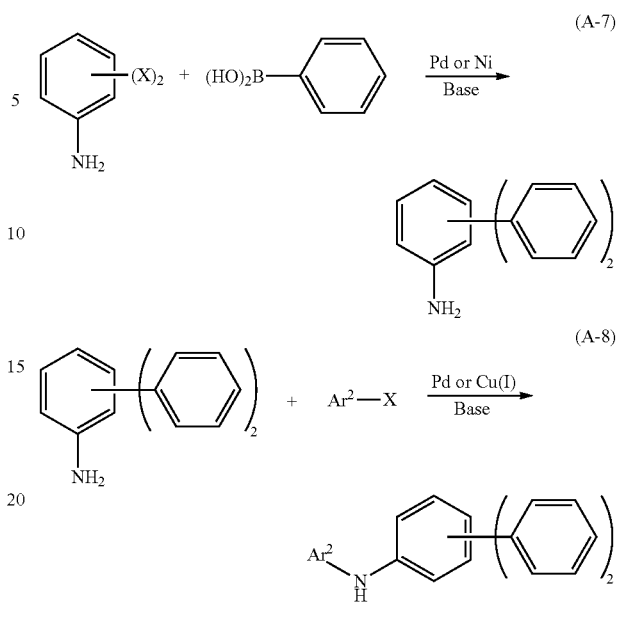

(A-7)

(A-8)

It is to be noted that the quinoxaline derivative of the invention can be purified by recrystallization since the quinoxaline derivative can be obtained as precipitation by a synthetic reaction shown in the synthetic scheme (A-2). That is, since impurities can be prevented from being mixed due to extraction or the like, a complicated or troublesome purification process is unnecessary. Therefore, the quinoxaline derivative of the invention can be obtained with high purity.

The quinoxaline derivative of the invention is bipolar and excellent in both an electron transporting property and a hole transporting property. Therefore, by using the quinoxaline derivative of the invention for an electronics device, a good electric characteristic can be obtained. Further, the quinoxaline derivative of the invention has a high glass transition point and excellent heat resistance; therefore, by using the quinoxaline derivative of the invention for an electronics device, an electronics device which has excellent heat resistance can be obtained. Furthermore, the quinoxaline derivative of the invention is stabilized with respect to electrochemical oxidation or reduction; therefore, by using the quinoxaline derivative of the invention for an electronics device, a long-life electronics device can be obtained.

Embodiment Mode 2

One mode of a light emitting element using the quinoxaline derivative of the invention is described below with reference to FIG. 1A.

A light emitting element of the invention has a plurality of layers between a pair of electrodes. The plurality of layers are stacked by combining layers which contain a substance having a high carrier injecting property and a substance having a high carrier transporting property so that a light emitting region is formed apart from the electrodes, that is, so that carries are recombined at a portion away from the electrodes.

In this embodiment mode, the light emitting element includes a first electrode 102; a first layer 103, a second layer 104, a third layer 105, and a fourth layer 106 which are stacked in this order over the first electrode 102; and a second electrode 107 provided over the fourth layer 106. In this embodiment mode, the first electrode 102 functions as an anode and the second electrode 107 functions as a cathode.

A substrate 101 is used to support the light emitting element. As the substrate 101, for example, glass, plastic, or the like can be used. Other materials than those may also be used as long as the light emitting element can be supported in a manufacturing process.

As the first electrode 102, a metal, an alloy, a conductive compound, or a mixture thereof, each of which has a high work function (specifically, 4.0 eV or higher) is preferably used. Specifically, for example, indium tin oxide (ITO), indium tin oxide containing silicon; indium zinc oxide (IZO) in which zinc oxide (ZnO) is mixed by 2 to 20 wt % into indium oxide; indium oxide containing 0.5 to 5 wt % of tungsten oxide and 0.1 to 1 wt % of zinc oxide (IWZO); or the like can be used. Although these conductive metal oxide films are generally formed by sputtering, it may be formed by applying a sol-gel method or the like. Alternatively, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as TiN), or the like can be used.

The first layer 103 contains a substance having a high hole injecting property. Molybdenum oxide ($MoO_x$), vanadium oxide ($VO_x$), ruthenium oxide ($RuO_x$), tungsten oxide ($WO_x$), manganese oxide ($MnO_x$), or the like can be used. Alternatively, the first layer 103 can be formed of a phthalocyanine-based compound such as phthalocyanine ($H_2Pc$) or copper phthalocyanine (CuPc); a high molecule such as poly(ethylene dioxythiophene)/poly(styrenesulfonic acid) (PEDOT/PSS); or the like.

Alternatively, a composite material including an organic compound and an inorganic compound may be used for the first layer 103. In particular, a composite material including an organic compound and an inorganic compound showing an electron-accepting property with respect to the organic compound is excellent in a hole injecting property and a hole transporting property since an electron is transferred between the organic compound and the inorganic compound and carrier density is increased. In that case, a material having an excellent hole transporting property is preferably used as the organic compound. Specifically, an aromatic amine-based organic compound or a carbazole-based organic compound is preferable. Alternatively, aromatic hydrocarbon may be used as the organic compound. As the inorganic compound, a substance showing an electron accepting property with respect to an organic compound may be used. Specifically, an oxide of a transition metal is preferable. For example, a metal oxide such as titanium oxide ($TiO_x$), vanadium oxide ($VO_x$), molybdenum oxide ($MoO_x$), tungsten oxide ($WO_x$), rhenium oxide ($ReO_x$), ruthenium oxide ($RuO_x$), chromium oxide ($CrO_x$), zirconium oxide ($ZrO_x$), hafnium oxide ($HfO_x$), tantalum oxide ($TaO_x$), silver oxide ($AgO_x$), or manganese oxide (MnOx) can be used. In the case of using a composite material including an organic compound and an inorganic compound for the first layer 103, the first layer 103 can have an ohmic contact with the first electrode 102; therefore, a material of the first electrode can be selected regardless of work function.

As a substance for forming the second layer 104, a substance having a high hole transporting property, specifically, an aromatic amine-based (that is, one having a bond of benzene ring-nitrogen) compound is preferable. A material that is widely used includes 4,4'-bis[N-(3-methylphenyl)-N-phenylamino]biphenyl, derivatives thereof such as 4,4'-bis[N-(1-napthyl)-N-phenylamino]biphenyl (hereinafter referred to as NPB), and star burst aromatic amine compounds such as 4,4',4"-tris(N,N-diphenyl-amino)triphenylamine, and 4,4',4"-tris[N-(3-methylphenyl)-N-phenylamino]triphenylamine. The substance described here are mainly a substance having a hole mobility of $10^{-6}$ cm$^2$/Vs or higher. However, other materials than those may also be used as long as a substance has a higher hole transporting property than an electron transporting property. Note that the second layer 104 may be a single layer or a mixed-layer of the above substances, or may be formed by stacking two or more layers.

The third layer 105 is a layer including a light emitting substance. In this embodiment mode, the third layer 105 includes the quinoxaline derivative of the invention described in Embodiment Mode 1. The quinoxaline derivative of the invention can preferably be applied to a light emitting element as a light emitting substance since the quinoxaline derivative exhibits light emission of blue to blue green.

The fourth layer 106 is formed of a substance having a high electron transporting property, for example, a metal complex having a quinoline skeleton or a benzoquinoline skeleton and the like, such as tris(8-quinolinolato)aluminum (abbreviated to Alq), tris(5-methyl-8-quinolinolato)aluminum (abbreviated to Almq$_3$), bis(10-hydroxybenzo[h]-quinolinato)beryllium (abbreviated to BeBq$_2$), or bis(2-methyl-8-quinolinolato)-4-phenylphenolato-aluminum (abbreviated to BAlq). Alternatively, a metal complex having an oxazole-based or a thiazole-based ligand, such as bis[2-(2-hydroxyphenyl)-benzoxazolato]zinc (abbreviated to Zn(BOX)$_2$) or bis[2-(2-hydroxyphenyl)-benzothiazolato]zinc (abbreviated to Zn(BTZ)$_2$) can be used. Alternatively, other than the metal complexes, 2-(4-biphenylyl)-5-(4-tert-butylphenyl)-1,3,4-oxadiazole (abbreviated to PBD), 1,3-bis[5-(p-tert-buthylphenyl)-1,3,4-oxadiazol-2-yl]benzene (abbreviated to OXD-7), 3-(4-tert-butylphenyl)-4-phenyl-5-(4-biphenylyl)-1,2,4-triazole (abbreviated to TAZ), 3-(4-tert-butylphenyl)-4-(4-ethylphenyl)-5-(4-biphenylyl)-1,2,4-triazole (abbreviated to p-EtTAZ), bathophenanthroline (abbreviated to BPhen), bathocuproin (abbreviated to BCP), or the like can be used. The substances described here are mainly a substance having an electron mobility of $10^{-6}$ cm$^2$/Vs or higher. However, other materials than those may also be used as long as a substance has a higher electron transporting property than a hole transporting property. Note that the fourth layer 106 may be a single layer or may be formed by stacking two or more layers including the above substances.

The second electrode 107 can be formed of a metal, an alloy, a conductive compound, mixture of these, or the like which has a low work function (work function of 3.8 eV or lower). As a specific example of such a cathode material, an element belonging to Group 1 or Group 2 in the periodic table, that is, an alkali metal such as lithium (U) or cesium (Cs), an alkaline earth metal such as magnesium (Mg), calcium (Ca), or strontium (Sr), an alloy containing any of these (such as MgAg or AlLi), a rare earth metal such as europium (Eu) or ytterbium (Yb), an alloy containing any of these, or the like can be cited. However, when a layer having a function of promoting electron injection is provided between the second electrode 107 and a light emitting layer and in contact with the second electrode 107, various conductive materials such as Al, Ag, ITO, or ITO containing silicon can be used for the second electrode 107 regardless of the work function.

For the layer having a function of promoting electron injection, a compound of an alkali metal or an alkaline earth metal, such as lithium fluoride (LiF), cesium fluoride (CsF), or calcium fluoride (CaF$_2$) can be used. Alternatively, a layer which includes a substance having an electron transporting property may be mixed with an alkali metal, an alkaline earth metal, an alkali metal compound, or an alkaline earth metal compound, for example, Alq containing lithium oxide (LiO$_x$), magnesium nitride (MgO$_x$), magnesium (Mg), or lithium (Li) can be used.

The first layer 103, the second layer 104, the third layer 105, and the fourth layer 106 may be formed by, for example, various methods such as an ink jet method, a spin coating method, and the like as well as an evaporation method. Moreover, a different film forming method may be used for each electrode or each layer.

In the light emitting element of the invention having the aforementioned structure, current flows due to a potential difference generated between the first electrode 102 and the second electrode 107 and holes and electrons are recombined in the third layer 105 which contains the substance having a high light emitting property, thereby light is emitted. That is, the structure is such that a light emitting region is formed in the third layer 105.

Figure 1B:
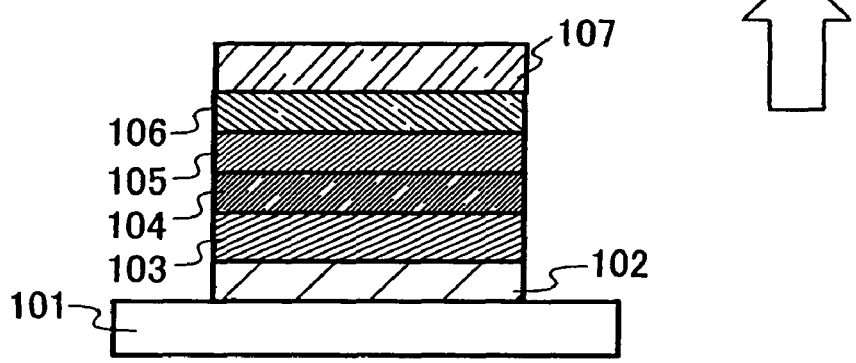
Figure 1C:
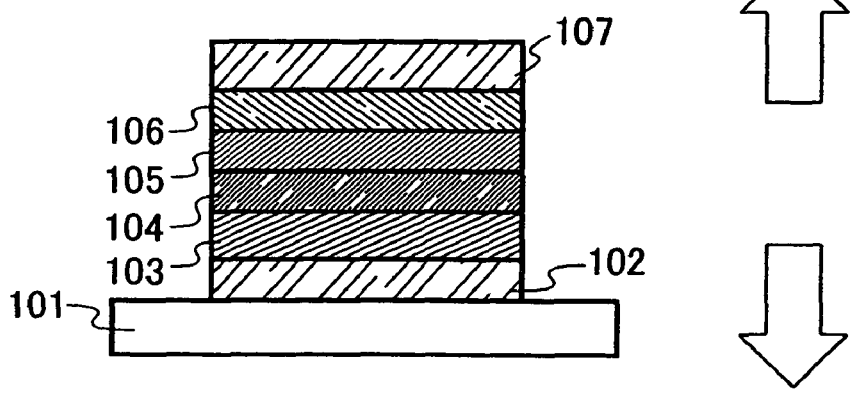

Light is extracted to the outside through one or both of the first electrode 102 and the second electrode 107. Therefore, one or both of the first electrode 102 and the second electrode 107 is formed of a substance having light transmissivity. If only the first electrode 102 is formed of a substance having light transmissivity, light is extracted from the substrate side through the first electrode 102 as shown in FIG. 1A. If only the second electrode 107 is formed of a substance having light transmissivity, light is extracted from an opposite side of the substrate side through the second electrode 107 as shown in FIG. 1B. If both of the first electrode 102 and the second electrode 107 are formed of a substance having light transmissivity, light is extracted from both of the substrate side and the opposite side of the substrate side through the first electrode 102 and the second electrode 107 as shown in FIG. 1C.

The structure of the layers provided between the first electrode 102 and the second electrode 107 is not limited to the aforementioned structure. Other structures than the aforementioned one may be applied as long as the structures are as follows: a light emitting region where holes and electrons are recombined is provided apart from the first electrode 102 and the second electrode 107 so that quenching due to approximation of the light emitting region and the metal is suppressed.

In other words, the stacked structure of the layers is not particularly limited, and a layer which includes a substance having a high electron transporting property, a substance having a high hole transporting property, a substance having a high electron injecting property, a substance having a high hole injecting property, a substance having a bipolar property (a substance having a high electron transporting property and a high hole transporting property), a hole blocking material, or the like may be freely combined with the quinoxaline derivative of the invention.

Figure 2:
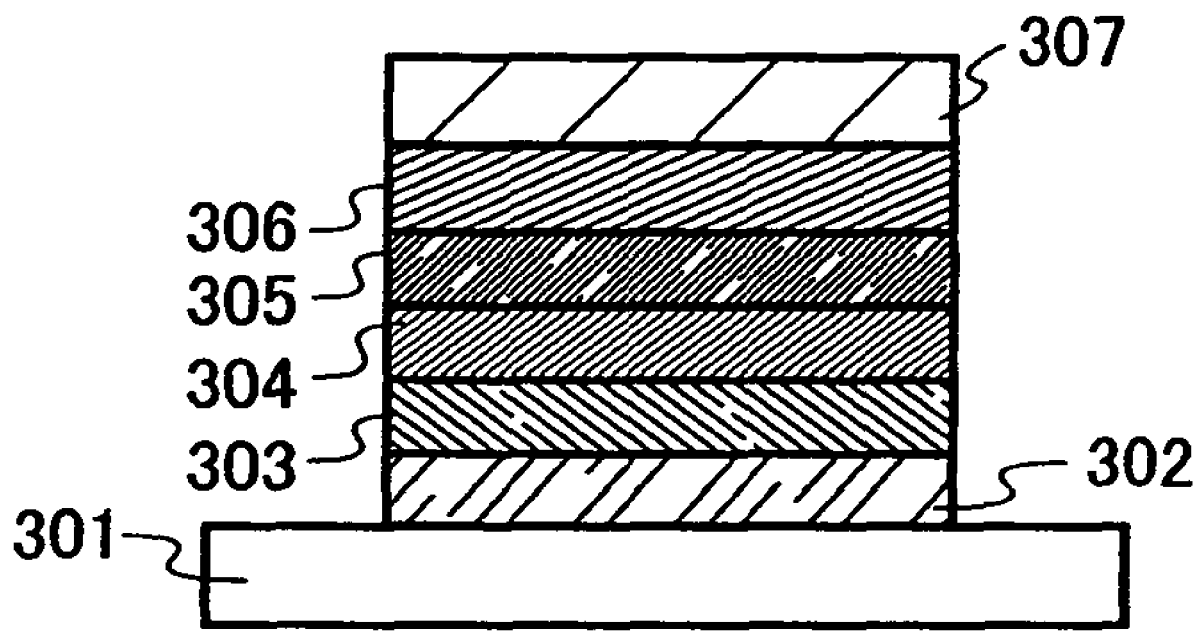
FIG. 2 is a view showing a light emitting element of the invention.

A light emitting element shown in FIG. 2 has a structure in which a first layer 303 which includes a substance having a high electron transporting property, a second layer 304 which includes a light emitting substance, a third layer 305 which includes a substance having a high hole transporting property, a fourth layer 306 which includes a substance having a high hole injecting property, and a second electrode 307 functioning as an anode are stacked in this order over a first electrode 302 functioning as a cathode. A reference numeral 301 denotes a substrate.

In this embodiment mode, the light emitting element is manufactured over the substrate made of glass, plastic, or the like. By manufacturing a plurality of such light emitting elements over one substrate, a passive light emitting device can be manufactured. Alternatively, for example, a thin film transistor (TFT) may be formed over a substrate made of glass, plastic, or the like, and the light emitting elements may be manufactured over an electrode electrically connected to the TFT. Thus, an active matrix light emitting device in which the driving of the light emitting element is controlled by the TFT can be manufactured. The structure of the TFT is not particularly limited. Either a staggered TFT or an inverted staggered TFT is applicable. Further, the crystallinity of a semiconductor used for the TFT is not particularly limited. Either an amorphous semiconductor or a crystalline semiconductor may be used. A driver circuit formed over a TFT array substrate may be formed by using one or both of an N-type TFT and a P-type TFT.

The quinoxaline derivative of the invention can be used as a light emitting layer without including another light emitting substance as described in this embodiment mode since the quinoxaline derivative is bipolar and a light emitting material.

Further, since the quinoxaline derivative of the invention is bipolar, a light emitting element in which a light emitting region is rarely located at an interface of stacked films, and which shows favorable characteristics with few changes in light emission spectrum and little decrease in light emission efficiency due to an interaction such as exciplex can be manufactured.

Further, an amorphous film which includes few microcrystalline components can be obtained since microcrystalline components are hardly included during a film formation. That is, the film has a favorable quality; therefore, a light emitting element with few element defects such as a dielectric breakdown due to electric field concentration can be manufactured.

Further, the quinoxaline derivative of the invention is a material which is bipolar and excellent in a carrier transporting property (an electron transporting property and a hole transporting property); therefore, when the quinoxaline derivative is used for a light emitting element, a driving voltage of the light emitting element can be reduced and thus the power consumption can be lowered.

Further, by using the quinoxaline derivative of the invention, which has a high glass transition point, a light emitting element having high heat resistance can be obtained.

Further, the quinoxaline derivative of the invention is stabilized with respect to oxidizing reactions and reductive reactions occurring alternately. That is, the quinoxaline derivative is electrochemically stabilized. Therefore, by using the quinoxaline derivative of the invention for a light emitting element, a long-life light emitting element can be obtained.

It is to be noted that the quinoxaline derivative of the invention in a solution state exhibits light emission of blue to blue green in a short wavelength region, and the quinoxaline derivative in a solid state also exhibits light emission in a short wavelength region. This is explained as follows. In the quinoxaline derivative of the invention, not a planar condensed aromatic ring such as a naphthyl group or a fluorenyl group but a twisted biphenyl group is connected to an amino group. It is considered that the quinoxaline derivative hardly assembles due to the twist form of the biphenyl group in a solid state and light emission colors almost corresponds to each other between in a solid state and in a solution state. That is, the quinoxaline derivative of the invention has such a characteristic that a peak of light emission spectrum is almost the same between in a solution state and in a solid state; therefore, by using the quinoxaline derivative in a thin film state (solid state) for a light emitting element, light emission with a short wavelength can be obtained.

Embodiment Mode 3

In this embodiment mode, description is made of a light emitting element having a different structure from that described in Embodiment Mode 2.

The third layer 105 described in Embodiment Mode 2 is formed by dispersing the quinoxaline derivative of the invention on another substance, thereby light emission can be obtained from the quinoxaline derivative of the invention. A light emitting element exhibiting light emission of blue to blue green can be obtained since the quinoxaline derivative of the invention exhibits light emission of blue to blue green.

Here, various materials can be used as a substance on which the quinoxaline derivative of the invention is dispersed. In addition to the substance having a high hole transporting property and the substance having a high electron transporting property, which are described in Embodiment Mode 2, 4,4'-di(N-carbazolyl)-biphenyl (abbreviated to CBP), 2,2',2"-(1,3,5-benzenetri-yl)-tris[1-phenyl-1H-benzimidazole] (abbreviated to TPBI), 9,10-di(2-naphthyl)anthracene (abbreviated to DNA), 2-tert-butyl-9,10-di(2-naphthyl)anthracene (abbreviated to t-BuDNA), and the like are cited.

The quinoxaline derivative of the invention is a material which is bipolar and excellent in a carrier transporting property (an electron transporting property and a hole transporting property); therefore, when the quinoxaline derivative is used for a light emitting element, a driving voltage of the light emitting element can be reduced and the power consumption can be lowered.

Further, using the quinoxaline derivative of the invention allows to obtain a light emitting element having high heat resistance since the quinoxaline derivative of the invention has a high glass transition point.

Further, the quinoxaline derivative of the invention is stabilized with respect to oxidizing reactions and reductive reactions occurring alternately. That is, the quinoxaline derivative is electrochemically stabilized. Therefore, using the quinoxaline derivative of the invention allows to obtain a long-life light emitting element.

It is to be noted that the structure described in Embodiment Mode 2 can be appropriately used for layers other than the third layer 105.

Embodiment Mode 4

In this embodiment mode, description is made of a light emitting element having a different structure from those described in Embodiment Modes 2 and 3.

The third layer 105 described in Embodiment Mode 2 is formed by dispersing a light emitting substance on the quinoxaline derivative of the invention, thereby, light emission can be obtained from the light emitting substance.

The quinoxaline derivative of the invention is bipolar, and has a favorable film quality since microcrystalline components are hardly included during a film formation; therefore, the quinoxaline derivative can be preferably used as a material on which another light emitting substance is dispersed.

In the case where the quinoxaline derivative of the invention is used as a material on which another light emitting substance is dispersed, a light emission color due to the light emitting substance can be obtained. Further, a mixed color of a light emission color due to the quinoxaline derivative of the invention and a light emission color due to the light emitting substance dispersed in the quinoxaline derivative can also be obtained.

Here, various materials can be used as a light emitting substance dispersed on the quinoxaline derivative of the invention. Specifically, a fluorescent substance such as 4-(dicyanomethylene)-2-methyl-6-(p-dimethylaminostyryl)-4H-pyran (abbreviated to DCM1), 4-(dicyanomethylene)-2-methyl-6-(joulolidine-4-yl-vinyl)-4H-pyran (abbreviated to DCM2), N,N'-dimethylquinacridone (abbreviated to DMQd), 9,10-diphenylanthracene (abbreviated to DPA); 5,12-diphenyltetracene (abbreviated to DPT), coumarin 6, perylene, or rubrene, or a phosphorescent substance such as bis[2-(2'-benzothienyl)pyridinato-N,C$^{3'}$](acetylacetonato) iridium (abbreviated to Ir(btp)$_2$(acac)) can be used.

Further, as a light emitting substance dispersed on the quinoxaline derivative of the invention, an organometallic complex having a structure expressed by the following general formula (101) can be used.

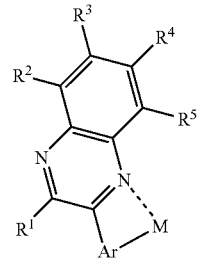

(101)

(in the formula, $R^1$ to $R^5$ each represent any one of hydrogen, a halogen element, an acyl group, an alkyl group, an alkoxyl group, an aryl group, a cyano group, and a heterocycle group. Ar represents an aryl group or a heterocycle group. M represents an element which belongs to Group 9 or Group 10.)

In the general formula (101), Ar is preferably an aryl group or a heterocycle group having an electron-withdrawing substituent. Since Ar is a group having an electron-withdrawing substituent, a phosphorescent organometallic complex having higher light emission intensity can be obtained.

In particular, an organometallic complex having a structure expressed by the following general formula (102) is preferable.

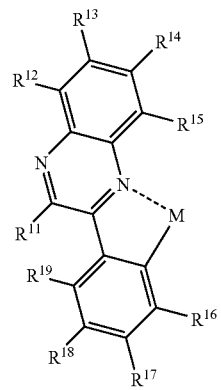

(102)

(in the formula, $R^{11}$ represents any one of alkyl groups having 1 to 4 carbon atoms. $R^{12}$ to $R^{15}$ each represent any one of hydrogen, a halogen element, an acyl group, an alkyl group, an alkoxyl group, an aryl group, a cyano group, and a heterocycle group. Further, $R^{16}$ to $R^{19}$ each represent any one of hydrogen, an acyl group, an alkyl group, an alkoxyl group, an aryl group, a heterocycle group, and an electron-withdrawing substituent. M represents an element which belongs to Group 9 or Group 10.)

In the general formula (102), at least one of $R^{16}$ to $R^{19}$ is preferably an electron-withdrawing substituent. Accordingly, a phosphorescent organometallic complex having higher light emission intensity can be obtained.

Further, in particular, an organometallic complex is preferably the one having a structure expressed by the following general formula (103).

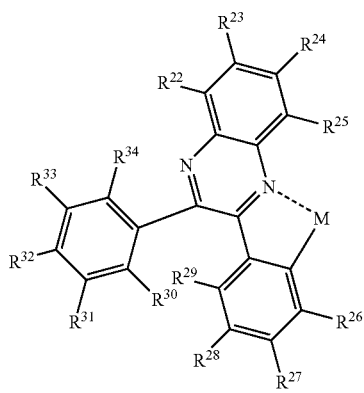

(103)

(in the formula, $R^{22}$ to $R^{34}$ each represent any one of hydrogen, a halogen element, an acyl group, an alkyl group, an alkoxyl group, an aryl group, a cyano group, a heterocycle group, and an electron-withdrawing substituent. M represents an element which belongs to Group 9 or Group 10.)

In the general formula (103), at least one of $R^{26}$ to $R^{29}$ is preferably an electron-withdrawing substituent. Accordingly, a phosphorescent organometallic complex having higher light emission intensity can be obtained.

An organometallic complex expressed by the general formula (104) is cited as an organometallic complex having a structure expressed by the aforementioned general formula (101).

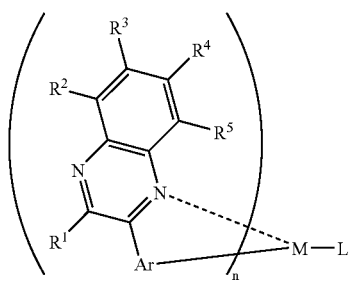

(104)

(in the formula, $R^1$ to $R^5$ each represent any one of hydrogen, a halogen element, an acyl group, an alkyl group, an alkoxyl group, an aryl group, a cyano group, and a heterocycle group. Ar represents an aryl group or a heterocycle group. M represents an element which belongs to Group 9 or Group 10. When M is a Group 9 element, n=2 is satisfied, whereas when M is a Group 10 element, n=1 is satisfied. L represents any one of a monoanionic ligand having a beta-diketone structure, a monoanionic bidentate chelate ligand having a carboxyl group, and a monoanionic bidentate chelate ligand having a phenol hydroxyl group.)

In the general formula (104), Ar is preferably an aryl group or a heterocycle group having an electron-withdrawing substituent. Since Ar is a group having an electron-withdrawing substituent, a phosphorescent organometallic complex having higher light emission intensity can be obtained.

In particular, an organometallic complex expressed by the following general formula (105) is preferable.

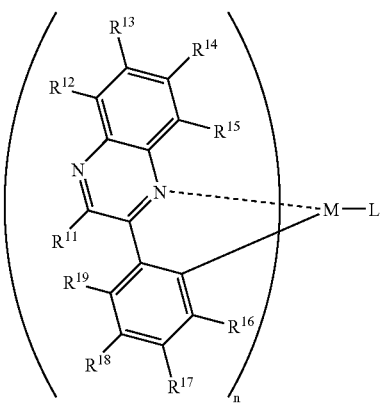

(105)

(in the formula, $R^{11}$ represents any one of alkyl groups having 1 to 4 carbon atoms. $R^{12}$ to $R^{15}$ each represent any one of hydrogen, a halogen element, an acyl group, an alkyl group, an alkoxyl group, an aryl group, a cyano group, and a heterocycle group. Further, $R^{16}$ to $R^{19}$ each represent any one of hydrogen, an acyl group, an alkyl group, an alkoxyl group, an aryl group, a heterocycle group, and an electron-withdrawing substituent. M represents an element which belongs to Group 9 or Group 10. When M is a Group 9 element, n=2 is satisfied, whereas when M is a Group 10 element, n=1 is satisfied. L represents any one of a monoanionic ligand having a beta-diketone structure, a monoanionic bidentate chelate ligand having a carboxyl group, and a monoanionic bidentate chelate ligand having a phenol hydroxyl group.)

In the general formula (105), at least one of $R^{16}$ to $R^{19}$ is preferably an electron-withdrawing substituent. Accordingly, a phosphorescent organometallic complex having higher light emission intensity can be obtained.

Further, in particular, an organometallic complex expressed by the following general formula (106) is preferable.

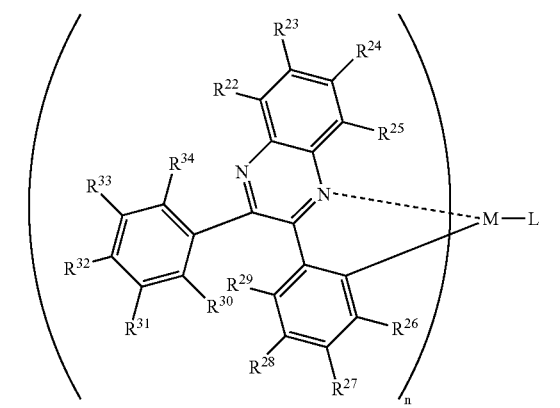

(106)

(in the formula, $R^{22}$ to $R^{34}$ each represent any one of hydrogen, a halogen element, an acyl group, an alkyl group, an alkoxyl group, an aryl group, a cyano group, a heterocycle group, and an electron-withdrawing substituent. M represents an element which belongs to Group 9 or Group 10. When M is a Group 9 element, n=2 is satisfied, whereas when M is a Group 10 element, n=1 is satisfied. L represents any one of a monoanionic ligand having a beta-diketone structure, a monoanionic bidentate chelate ligand having a carboxyl group, and a monoanionic bidentate chelate ligand having a phenol hydroxyl group.)

In the general formula (106), at least one of $R^{26}$ to $R^{29}$ is preferably an electron-withdrawing substituent. Accordingly, a phosphorescent organometallic complex having higher light emission intensity can be obtained.

In the organometallic complexes having the structures expressed by the general formulas (101) to (103), and the organometallic complex expressed by the general formulas (104) to (106), the electron-withdrawing substituent is preferably a halogen group, a haloalkyl group, or a cyano group. Accordingly, chromaticity and quantum efficiency of the organometallic complex are improved. Further, a fluoro group is particularly preferable among halogen groups and a trifluoromethyl group is particularly preferable among haloalkyl groups. Accordingly, electrons can be trapped efficiently.

In the organometallic complexes having the structures expressed by the general formulas (101) to (103), and the organometallic complexes expressed by the general formulas (104) to (106), a central metal M is preferably a heavy metal, and more preferably, iridium or platinum. Accordingly, a heavy atom effect can be obtained.

In the general formulas (104) to (106), a ligand L may be any of a monoanionic ligand having a beta-diketone structure, a monoanionic bidentate chelate ligand having a carboxyl group, and a monoanionic bidentate chelate ligand having a phenol hydroxyl group. However, any one of monoanionic ligands expressed by the following structure formulas (107) to (113) is preferable. These monoanionic chelate ligands are useful since they have high coordinative ability and are inexpensive.

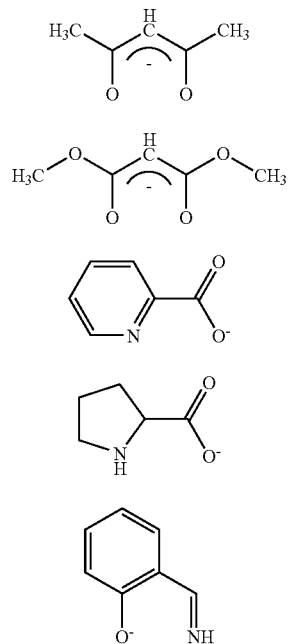

(107)

(108)

(109)

(110)

(111)

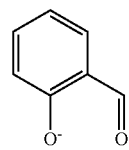

(112)

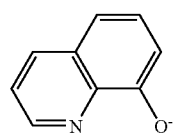

(113)

Organometallic complexes expressed by the structure formulas (114) to (126) are cited as specific examples of the organometallic complexes expressed by the aforementioned general formulas (101) to (106)

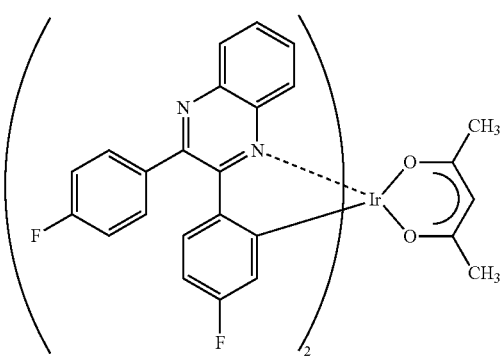

(114)

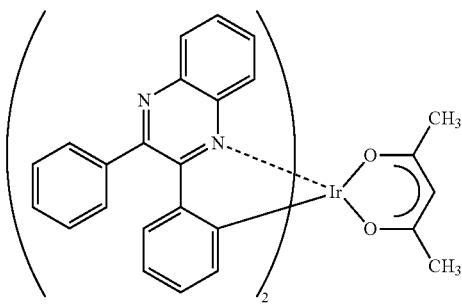

(115)

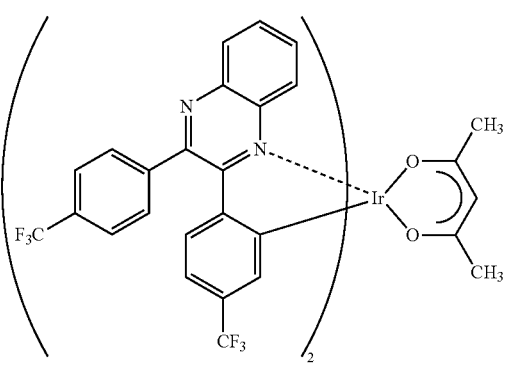

(116)

(117)
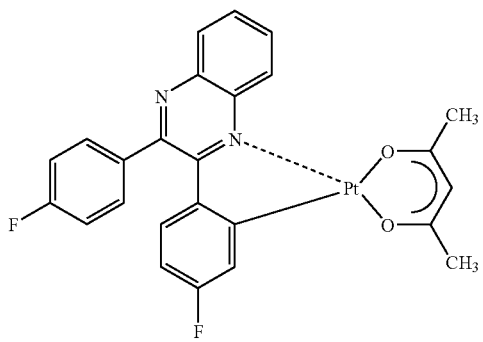
(118)
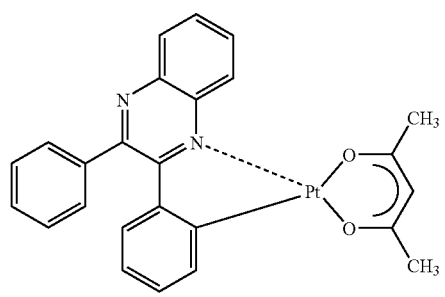
(119)
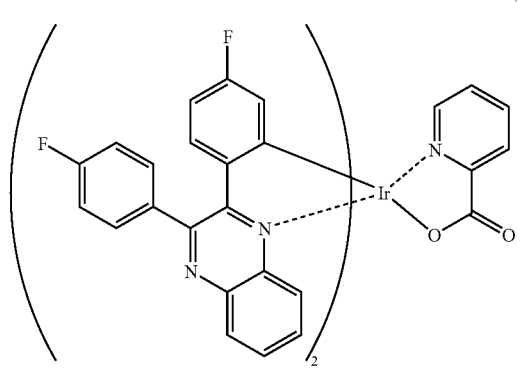
(120)
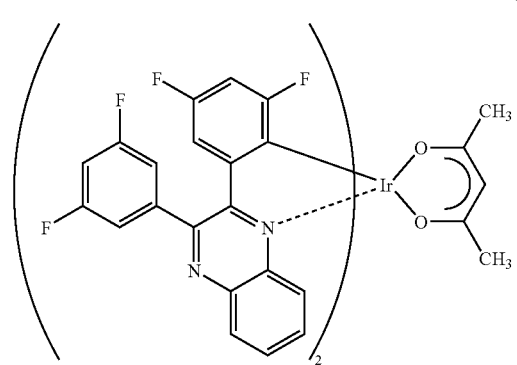
(121)
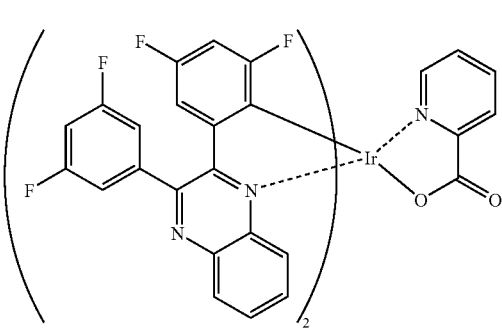
(122)
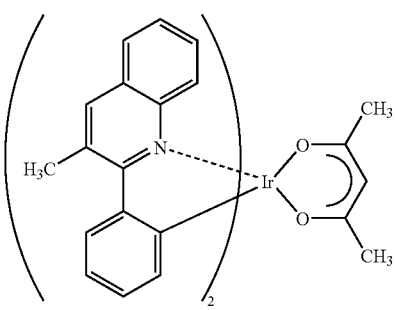
(123)
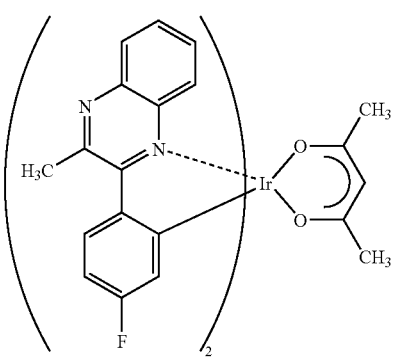
(124)
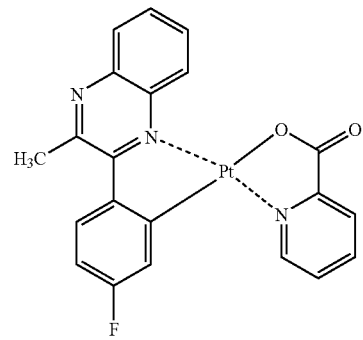

-continued

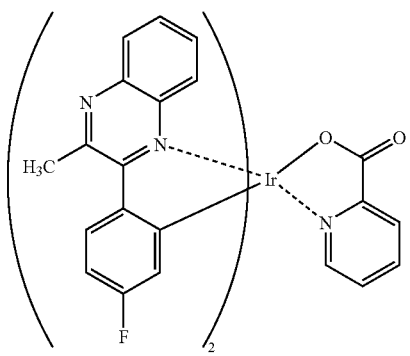

(125)

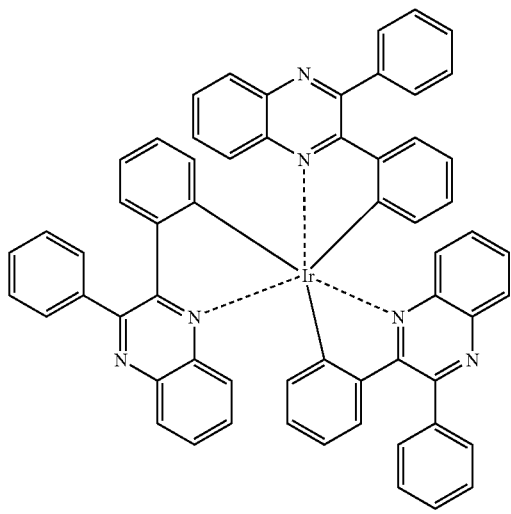

(126)

It is to be noted that a light emitting element in which light emission is obtained from a triplet excitation state by adding the aforementioned organometallic complex, which is a phosphorescent substance, to the quinoxaline derivative of the invention has a low driving voltage and high current efficiency. Therefore, a light emitting element consuming low power can be obtained.

The quinoxaline derivative of the invention is a material which is bipolar and excellent in a carrier transporting property (an electron transporting property and a hole transporting property); therefore, when the quinoxaline derivative of the invention is used for a light emitting element, a driving voltage of the light emitting element can be lowered.

Further, by using the quinoxaline derivative of the invention, which has a high glass transition point, a light emitting element having high heat resistance can be obtained.

Further, the quinoxaline derivative of the invention is stabilized with respect to oxidizing reactions and reductive reactions occurring alternately. That is, the quinoxaline derivative of the invention is electrochemically stabilized. Therefore, by using the quinoxaline derivative of the invention for a light emitting element, a long-life light emitting element can be obtained.

Further, in particular, by applying a light emitting layer in which a specific organometallic complex expressed by the aforementioned general formula (101) is dispersed on the quinoxaline derivative of the invention, a long-life light emitting element consuming significantly low power can be obtained.

It is to be noted that the quinoxaline derivative of the invention in a solution state exhibits light emission of blue to blue green in a short wavelength region, and the quinoxaline derivative in a solid state also exhibits light emission in a short wave length region. This is explained as follows. In the quinoxaline derivative of the invention, not a planar condensed aromatic ring such as a naphthyl group or a fluorenyl group but a twisted biphenyl group is connected to an amino group. It is considered that the quinoxaline derivative hardly assembles due to the twist form of the biphenyl skeleton in a solid state and light emission colors almost corresponds to each other between in a solid state and in a solution state. That is, the quinoxaline derivative of the invention has such a characteristic that a peak of light emission spectrum is almost the same between in a solution state and in a solid state; therefore, by using the quinoxaline derivative in a thin film state (solid state) for a light emitting element, alternatives of a light emitting substance which is dispersed on the quinoxaline derivative are increased. Specifically, in the case of using a phosphorescent substance as a light emitting substance which is dispersed, a light emission spectrum of the phosphorescent substance preferably has a peak at 560 nm to 700 nm. Meanwhile, in the case of using a fluorescent substance, a light emission spectrum of the phosphorescent substance preferably has a peak at 500 nm to 700 nm, and more preferably, 500 nm to 600 nm.

It is to be noted that the structure described in Embodiment Mode 2 can be used for layers other than the third layer 105.

Embodiment Mode 5

In this embodiment mode, a mode in which the quinoxaline derivative of the invention is used for an active layer of a vertical transistor (SIT) which is a kind of an organic semiconductor element, is described as an example.

Figure 7:
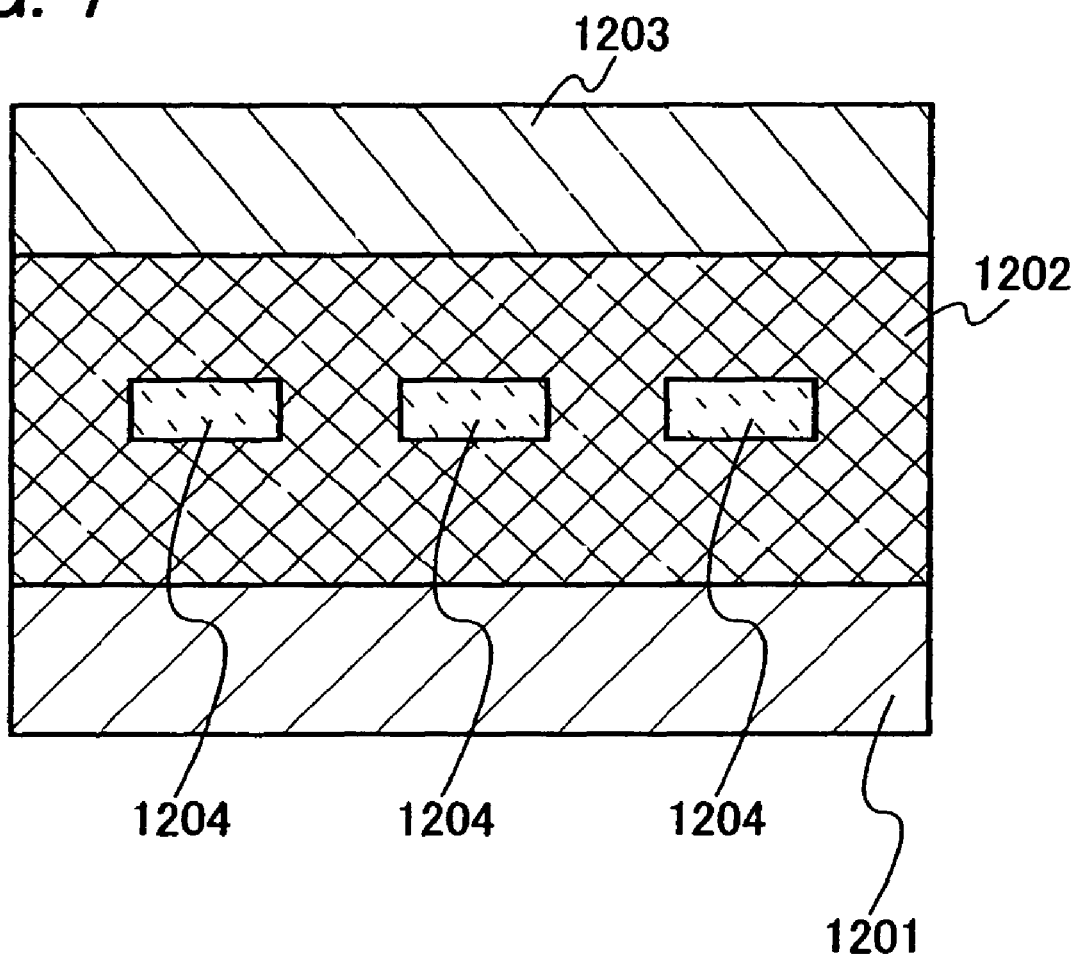
FIG. 7 is a cross sectional view of an organic semiconductor element of the invention.

The element has a structure in which a thin active layer 1202 including the quinoxaline derivative of the invention is sandwiched between a source electrode 1201 and a drain electrode 1203, and a gate electrode 1204 is embedded in the active layer 1202, as shown in FIG. 7. The gate electrode 1204 is electrically connected to a unit for applying a gate voltage, and the source electrode 1201 and the drain electrode 1203 are electrically connected to a unit for controlling a source-drain voltage.

In such an element structure, when a voltage is applied between the source and the drain under the condition where a gate voltage is not applied, a current flows (be in an ON state). When a gate voltage is applied in this state, a depletion layer is generated on the periphery of the gate electrode 1204, thereby a current does not flow (be in an OFF state). With the aforementioned mechanism, the element operates as a transistor.

In a vertical transistor, a material which has both a carrier transporting property and an excellent film quality is required for an active layer similarly to a light emitting element. The quinoxaline derivative of the invention is useful since it sufficiently meets the requirement.

Embodiment Mode 6

In this embodiment mode, a light emitting device manufactured using the quinoxaline derivative of the invention is described with reference to FIGS. 3A and 3B.

Figure 3A:
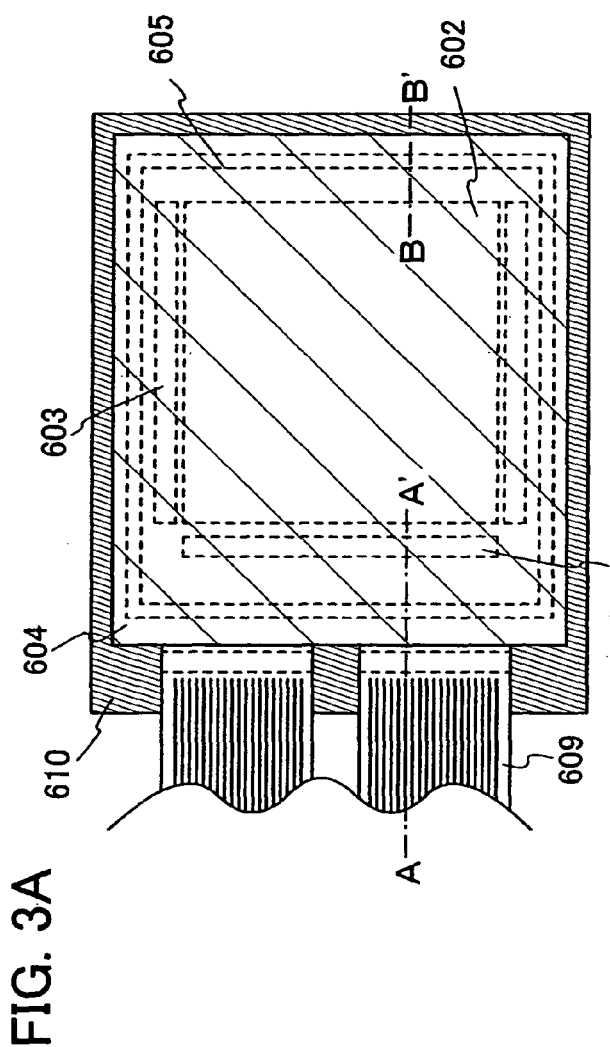
FIGS. 3A and 3B are views each showing a light emitting device of the invention.
Figure 3B:
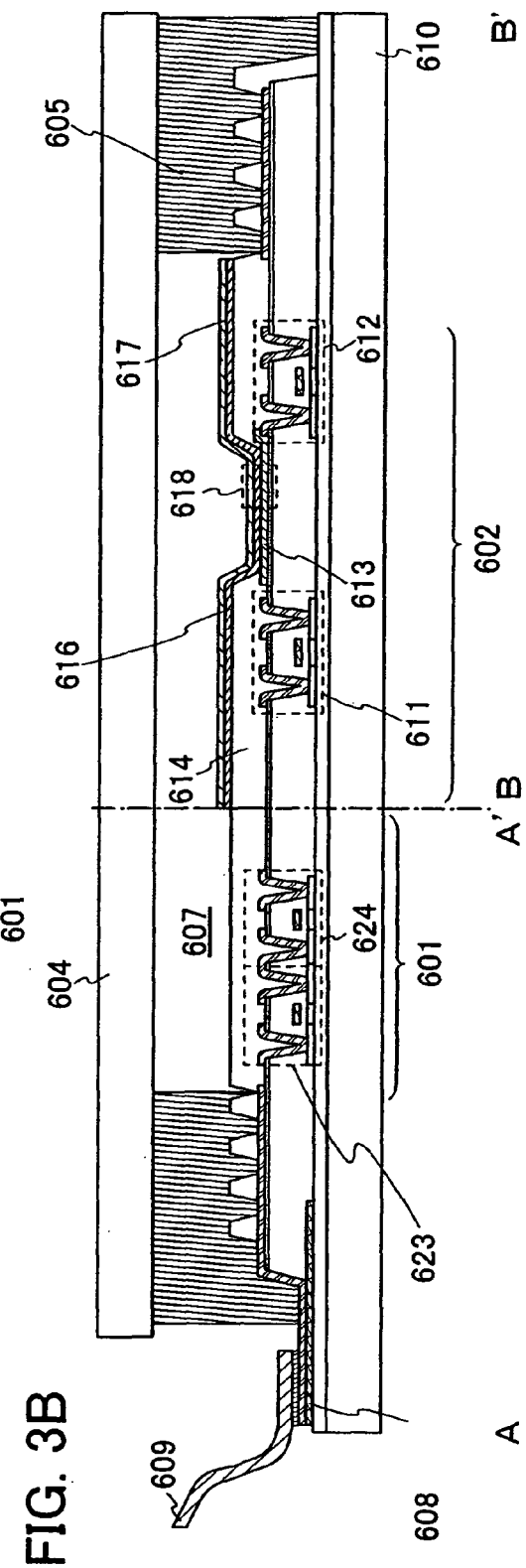

It is to be noted that FIG. 3A is a top plan view showing a light emitting device and FIG. 3B is a cross-sectional view of FIG. 3A taken along lines A-A' and B-B'. Reference numeral 601 denotes a driver circuit portion (source side driver circuit); 602 denotes a pixel portion; and 603 denotes a driver circuit portion (gate side driver circuit), which are indicated by dotted lines. Reference numeral 604 denotes a sealing substrate; 605 denotes a sealing material; and a portion surrounded by the sealing material 605 corresponds to a space 607.

It is to be noted that a lead wiring 608 is a wiring for transmitting a signal to be inputted to the source side driver circuit 601 and the gate side driver circuit 603 and receives a video signal, a clock signal, a start signal, a reset signal, and the like from an FPC (flexible printed circuit) 609 that is an external input terminal. It is to be noted that only the FPC is shown here; however, the FPC may be provided with a printed wiring board (PWB). The light emitting device in this specification includes not only a light emitting device itself but also a light emitting device attached with an FPC or a PWB.

Subsequently, a cross-sectional structure is described with reference to FIG. 3B. The driver circuit portion and the pixel portion are formed over an element substrate 610. Here, the source side driver circuit 601 which is the driver circuit portion and one pixel in the pixel portion 602 are shown.

It is to be noted that a CMOS circuit, which is a combination of an n-channel TFT 623 and a p-channel TFT 624, is formed as the source side driver circuit 601. A TFT for forming the driver circuit may be formed using various circuits such as a PMOS circuit or an NMOS circuit. Although a driver integration type in which a driver circuit is formed over a substrate is described in this embodiment mode, a driver circuit is not necessarily formed over a substrate and can be formed outside a substrate. Further, crystallinity of a semiconductor used for a TFT is not particularly limited. Either an amorphous semiconductor or a crystalline semiconductor may be used.

The pixel portion 602 has a plurality of pixels, each of which includes a switching TFT 611, a current control TFT 612, and a first electrode 613 which is electrically connected to a drain of the current control TFT 612. It is to be noted that an insulator 614 is formed so as to cover an end portion of the first electrode 613. Here, a positive photosensitive acrylic resin film is used for the insulator 614.

The insulator 614 is formed so as to have a curved surface having curvature at an upper end portion or a lower end portion thereof in order to make the coverage favorable. For example, in the case of using positive photosensitive acrylic as a material for the insulator 614, the insulator 614 is preferably formed so as to have a curved surface with a curvature radius (0.2 μm to 3 μm) only at the upper end portion thereof. Either a negative type which becomes insoluble in an etchant by light irradiation or a positive type which becomes soluble in an etchant by light irradiation can be used as the insulator 614.

A layer 616 including a light emitting substance and a second electrode 617 are formed over the first electrode 613. Here, a material having a high work function is preferably used as a material for the first electrode 613 which serves as an anode. For example, the first electrode 613 can be formed by using stacked layers of a titanium nitride film and a film containing aluminum as its main component; a three-layer structure of a titanium nitride film, a film including aluminum as its main component, and another titanium nitride film; or the like as well as a single-layer film such as an ITO film, an indium tin oxide film containing silicon, an indium oxide film containing zinc oxide of 2 to 20 wt %, a titanium nitride film, a chromium film, a tungsten film, a Zn film, or a Pt film. When the first electrode 613 has a stacked layer structure, it can have low resistance as wiring and form a favorable ohmic contact. Further, the first electrode 613 can function as an anode.

In addition, the layer 616 including a light emitting substance is formed by various methods such as an evaporation method using an evaporation mask, an ink-jet method, and a spin coating method. The layer 616 including a light emitting substance has the quinoxaline derivative of the invention described in Embodiment Mode 1. Further, the layer 616 including a light emitting substance may include another material such as a low molecular-based material, a medium molecular material (including an oligomer and a dendrimer), or a high molecular-based material. In addition, as a material used for the layer including a light emitting substance, a single layer or stacked layers of an organic compound is generally used. However, the invention also includes a structure in which an inorganic compound is used for a part of a film made of the organic compound.

As a material used for the second electrode 617 which is formed over the layer 616 including a light emitting substance and serves as a cathode, a material having a low work function (Al, Mg, Li, Ca, or an alloy or a compound of these such as MgAg, MgIn, AlLi, LiF, or $CaF_2$) is preferably used. In the case where light generated in the layer 616 including a light emitting substance is transmitted through the second electrode 617, stacked layers of a metal thin film and a light transmissive conductive film (of ITO, indium oxide containing zinc oxide of 2 to 20 wt %, indium tin oxide containing silicon, zinc oxide (ZnO), or the like) are preferably used as the second electrode 617.

By attaching the sealing substrate 604 to the element substrate 610 with the sealing material 605, a light emitting element 618 is provided in the space 607 surrounded by the element substrate 610, the sealing substrate 604, and the sealing material 605. It is to be noted that the space 607 is filled with a filler. There is also a case where the space 607 is filled with the sealing material 605 as well as an inert gas (nitrogen, argon, or the like).

It is to be noted that an epoxy-based resin is preferably used as the sealing material 605. The material desirably allows as little moisture and oxygen as possible to penetrate. As the sealing substrate 604, a plastic substrate made of FRP (Fiberglass-Reinforced Plastics), PVF (polyvinyl fluoride), Myler, polyester, acrylic, or the like can be used besides a glass substrate or a quartz substrate.

As described above, a light emitting device manufactured using the quinoxaline derivative of the invention can be obtained.

A light emitting device of the invention can have favorable characteristics since the quinoxaline derivative of the invention described in Embodiment Mode 1 is used for the light emitting device. Specifically, a highly heat resistant light emitting device can be obtained.

Further, a long-life light emitting device can be obtained since the quinoxaline derivative of the invention is electrochemically stable.

Further, the quinoxaline derivative of the invention is a material which is bipolar and excellent in a carrier transporting property (an electron transporting property and a hole transporting property); therefore, when the quinoxaline derivative of the invention is used for a light emitting element, a driving voltage of the light emitting element and the power consumption of a light emitting device can be lowered. In particular, in the case of using a phosphorescent substance as a light emitting substance, a light emitting device which has high light emission efficiency and consumes lower power can be obtained.

Figure 4:
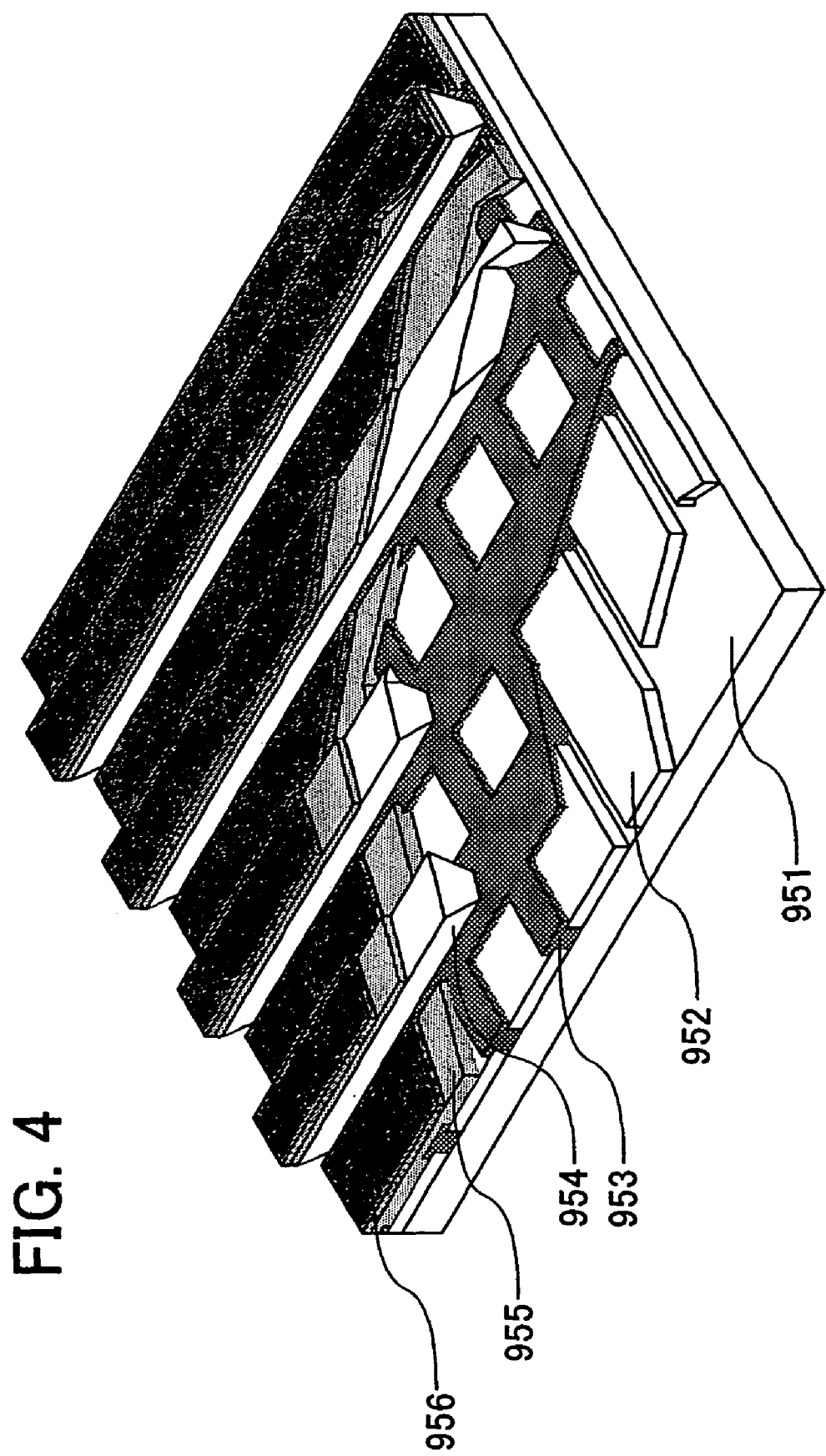
FIG. 4 is a view showing a light emitting device of the invention.

In this embodiment mode, description is made of an active light emitting device for controlling driving of a light emitting element by a transistor. Alternatively, a passive light emitting device which drives a light emitting element without particularly providing an element for driving such as a transistor may also be used. FIG. 4 shows a perspective view of a passive light emitting device which is manufactured by applying the invention. In FIG. 4, a layer 955 including a light emitting substance is provided between an electrode 952 and an electrode 956 over a substrate 951. An edge portion of the electrode 952 is covered with an insulating layer 953. Then, a partition layer 954 is provided over the insulating layer 953. A side wall of the partition layer 954 slopes so that a distance between one side wall and the other side wall becomes narrow toward a substrate surface. In other words, a cross section of the partition layer 954 in the direction of a short side is trapezoidal, and a base (side facing in the same direction as a plane direction of the insulating layer 953 and in contact with the insulating layer 953) is shorter than an upper side (side facing in the same direction as the plane direction of the insulating layer 953 and not in contact with the insulating layer 953). By providing the partition layer 954 in this manner, a defect of the light emitting element due to static electricity or the like can be prevented. In addition, the passive light emitting device can also be driven with low power consumption when it includes the light emitting element of the invention which operates at a low driving voltage.

Embodiment Mode 7

In this embodiment mode, description is made of an electronic appliance of the invention including the light emitting device described in Embodiment Mode 4. The electronic appliance of the invention including the quinoxaline derivative described in Embodiment Mode 1 has a display portion which has high heat resistance and a long life, and consumes lower power.

As an electronic appliance including a light emitting element manufactured using the quinoxaline derivative of the invention, a camera such as a video camera or a digital camera, a goggle type display, a navigation system, an audio reproducing device (car audio component stereo, audio component stereo, or the like), a computer, a game machine, a portable information terminal (mobile computer, mobile phone, portable game machine, electronic book, or the like), and an image reproducing device provided with a recording medium (specifically, a device capable of reproducing a recording medium such as a Digital Versatile Disc (DVD) and provided with a display device that can display the image), and the like are given. Specific examples of these electronic appliances are shown in FIGS. 5A to 5D.

Figure 5A:
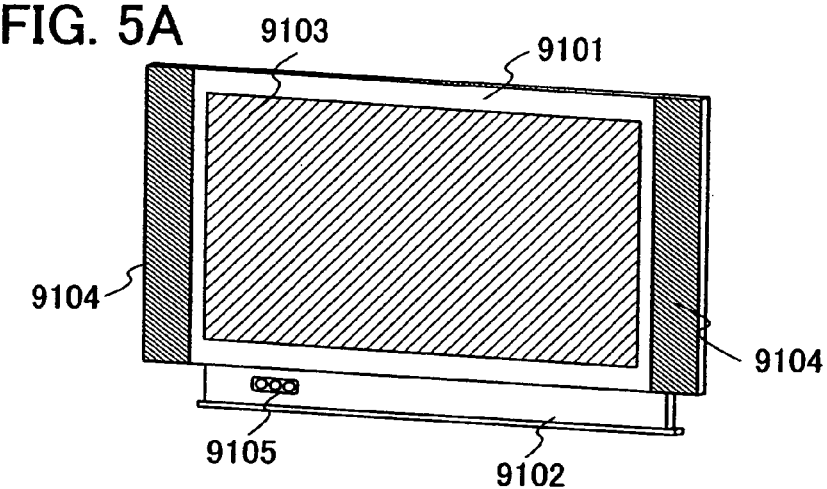
FIGS. 5A to 5D are views each showing an electronic appliance of the invention.

FIG. 5A shows a television device according to the invention, which includes a housing 9101, a supporting base 9102, a display portion 9103, a speaker portion 9104, a video input terminal 9105, and the like. In the television device, the display portion 9103 has light emitting elements similar to those described in Embodiment Modes 2 to 4, which are arranged in matrix. One feature of the light emitting element is that driving with a low voltage can be performed and the life is long. In addition, the heat resistance is high. The display portion 9103 which includes the light emitting elements has a similar feature. Therefore, in the television device, image quality is hardly deteriorated and low power consumption is achieved. With such a feature, deterioration compensation functions and power source circuits can be significantly reduced or downsized in the television device; therefore, small size and lightweight housing 9101 and supporting base 9102 can be achieved. In the television device according to the invention, low power consumption, high image quality, and small size and lightweight are achieved; therefore, a product which is suitable for living environment can be provided.

Figure 5B:
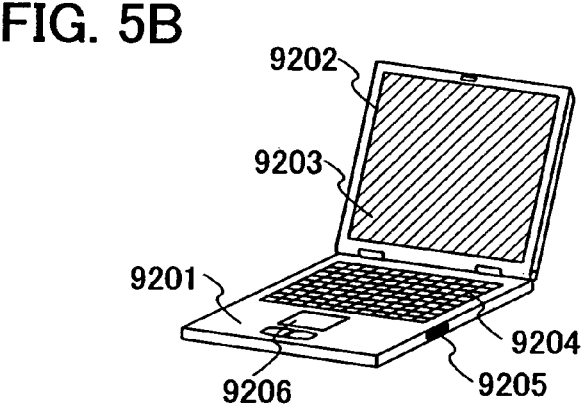

FIG. 5B shows a computer according to the invention, which includes a main body 9201, a housing 9202, a display portion 9203, a keyboard 9204, an external connection port 9205, a pointing mouse 9206, and the like. In the computer, the display portion 9203 has light emitting elements similar to those described in Embodiment Modes 2 to 4, which are arranged in matrix. One feature of the light emitting element is that driving with a low voltage can be performed and the life is long. In addition, the heat resistance is high. The display portion 9203 which includes the light emitting elements has a similar feature. Therefore, in the computer, image quality is hardly deteriorated and lower power consumption is achieved. With such a feature, a deterioration compensation function and the number of power source circuits can be significantly removed or reduced in the computer; therefore, small size and lightweight main body 9201 and housing 9202 can be achieved. In the computer according to the invention, low power consumption, high image quality, and small size and lightweight are achieved; therefore, a product which is suitable for living environment can be provided.

Figure 5C:
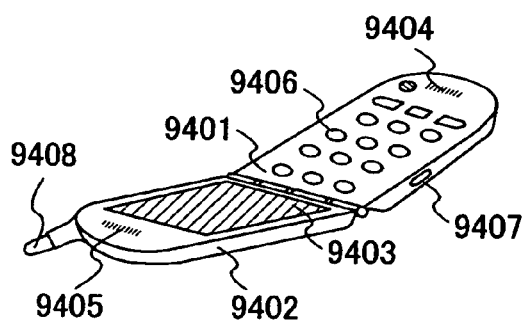

FIG. 5C shows a mobile phone according to the invention, which includes a main body 9401, a housing 9402, a display portion 9403, an audio input portion 9404, an audio output portion 9405, an operation key 9406, an external connection port 9407, an antenna 9408, and the like. In the mobile phone, a display portion 9403 has light emitting elements similar to those described in Embodiment Modes 2 to 4, which are arranged in matrix. Another feature of the light emitting element is that driving with a low voltage can be performed and the life is long. In addition, the heat resistance is high. The display portion 9403 which includes the light emitting elements has a similar feature. Therefore, in the mobile phone, image quality is hardly deteriorated and lower power consumption is achieved. With such a feature, a deterioration compensation function and the number of power source circuits can be significantly removed or reduced in the mobile phone; therefore, a small size and lightweight of the main body 9401 and the housing 9402 can be achieved. In the mobile phone according to the invention, low power consumption, high image quality, and a small size and lightweight are achieved; therefore, a production which is suitable for carrying can be provided.

Figure 5D:
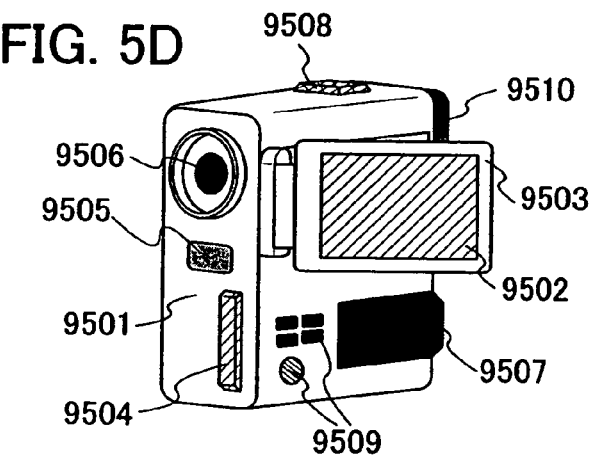

FIG. 5D shows a camera according to the invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the camera, the display portion 9502 has light emitting elements similar to those described in Embodiment Modes 2 to 4, which are arranged in matrix. One feature of the light emitting element is that driving with a low voltage can be performed and the life is long. In addition, the heat resistance is high. The display portion 9502 which includes the light emitting elements has a similar feature. Therefore, in the camera, image quality is hardly deteriorated and lower power consumption can be achieved. With such a feature, deterioration compensation functions and power source circuits can be significantly reduced or downsized in the camera; therefore, small size and lightweight main body 9501 can be achieved. In the camera according to the present invention, low power consumption, high image quality, and small size and lightweight are achieved; therefore, a product which is suitable for carrying can be provided.

As described above, the applicable range of the light emitting device of the invention is so wide that the light emitting device can be applied to electronic appliances in various fields. By using the quinoxaline derivative of the invention, electronic appliances which have display portions consuming low power and having a long life and high heat resistance can be provided.

The light emitting device of the invention can also be used as a lighting installation. One mode using the light emitting element of the invention as the lighting device is described with reference to FIG. 6.

Figure 6:
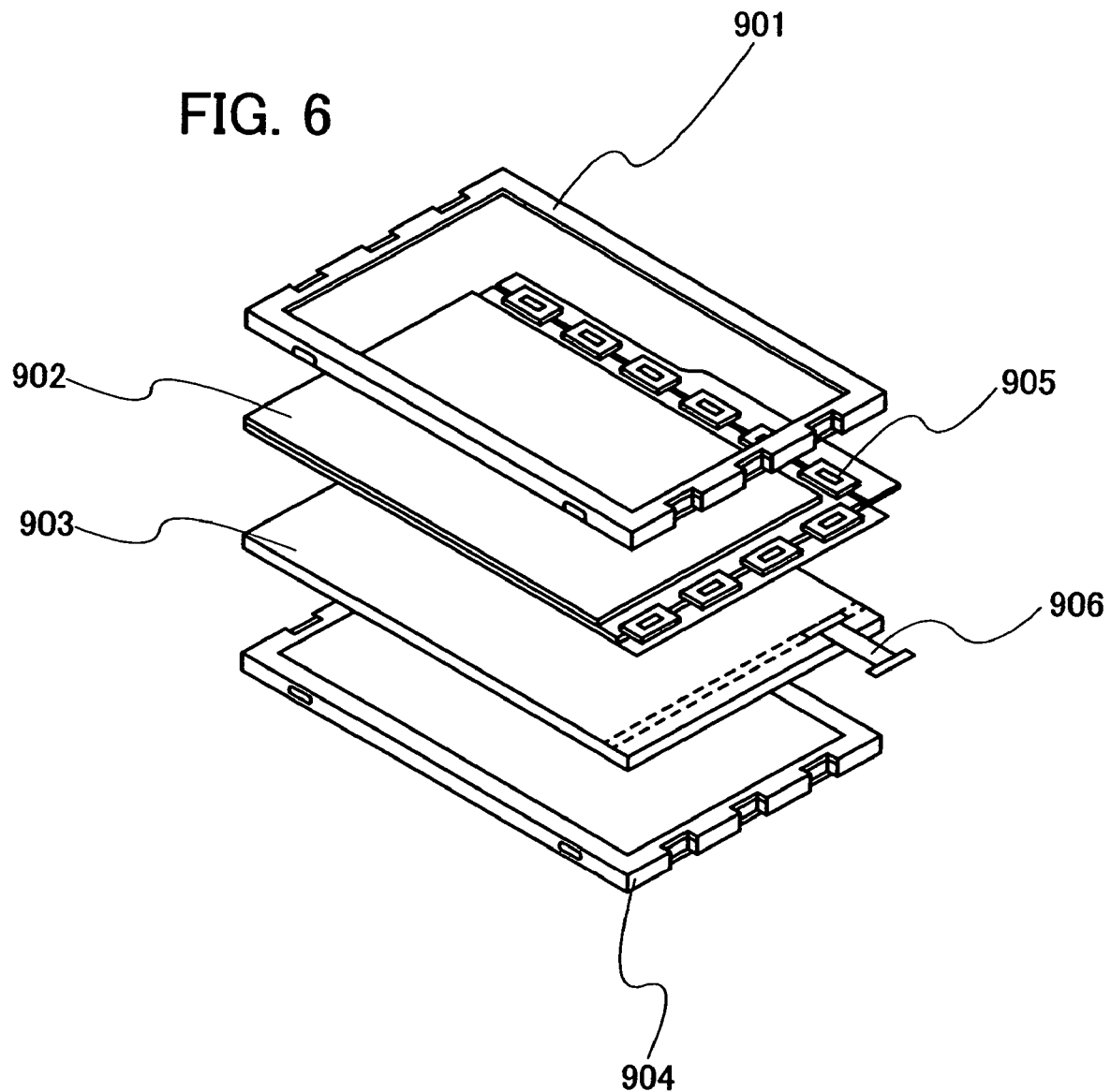
FIG. 6 is a view showing an electronic appliance of the invention.

FIG. 6 shows an example of a liquid crystal display device using the light emitting device of the invention as a backlight. The liquid crystal display device shown in FIG. 6 includes a housing 901, a liquid crystal layer 902, a backlight 903, and a housing 904, and the liquid crystal layer 902 is connected to a driver IC 905. The light emitting device of the invention is used for the backlight 903, and current is supplied through a terminal 906.

By using the light emitting device of the invention as the backlight of the liquid crystal display device, a backlight with reduced power consumption can be obtained. The light emitting device of the invention is a lighting device with plane light emission, and can have a large area. Therefore, the backlight can have a large area, and a liquid crystal display device having a large area can be obtained. Furthermore, the light emitting device of the invention has a thin shape and consumes low power; therefore, a thin shape and low power consumption of a display device can also be achieved. Since the light emitting device of the invention has a long life and an excellent heat resistance, a liquid crystal display device using the light emitting device also has a long life and an excellent heat resistance.

Embodiment 1

In this embodiment, a synthesis example of 2,3-bis{4-[N-(4-bipheniryl)-N-phenylamino]phenyl}quinoxaline (hereinafter referred to as BPAPQ), which is the quinoxaline derivative of the invention expressed by the following structure formula (14), is specifically shown.

(14)

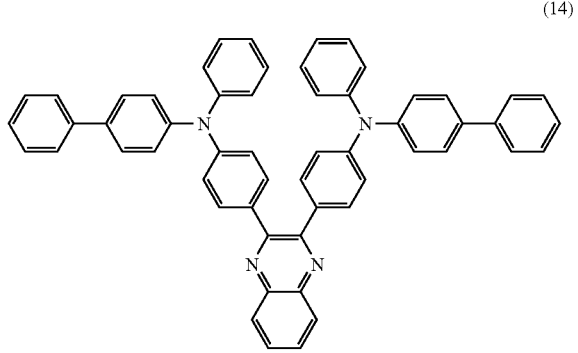

[Step 1]

A synthesis method of 2,3-bis(4-bromophenyl)quinoxaline is described. A synthesis scheme of 2,3-bis(4-bromophenyl)quinoxaline is shown in (B-1).

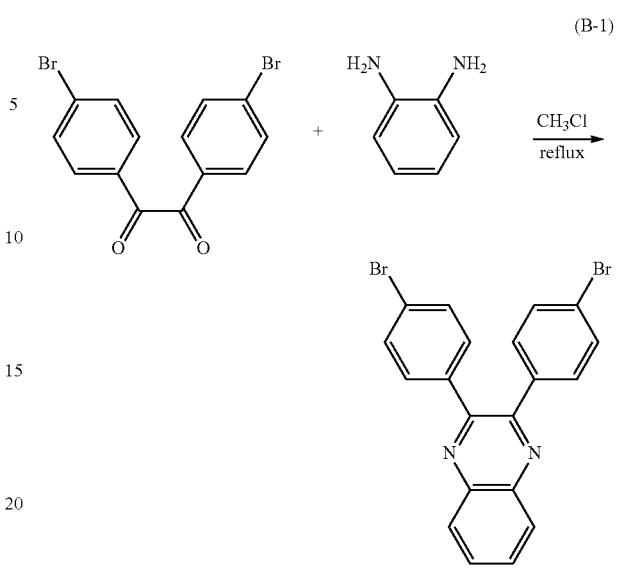

In a nitrogen atmosphere, a chloroform solution (200 mL) containing 30.0 g (81.5 mmol) of 4,4'-dibromobenzyl and 9.00 g (83.2 mmol) of o-phenylenediamine is refluxed at 80° C. for three hours. The reaction solution is washed with water after being cooled to a room temperature. The obtained aqueous phase is subjected to extraction with chloroform, and the solution obtained by extraction is washed with saturated saline together with the organic phase. After the organic phase is dried with magnesium sulfate, the mixture is subjected to suction filtration and the filtrate is condensed. Accordingly, 33 g (yield: 92%) of 2,3-bis(4-bromophenyl)quinoxaline which is an object is obtained as a white solid.

[Step 2]

A synthesis method of N-(4-biphenylyl)-N-phenylamine is described. A synthesis scheme of N-(4-biphenylyl)-N-phenylamine is shown in (B-2).

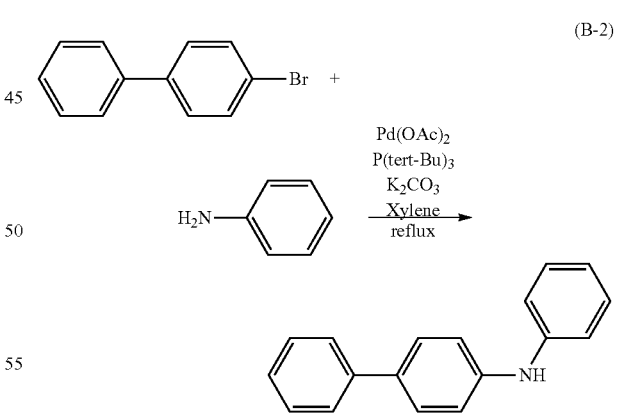

In a nitrogen atmosphere, a xylene suspension (150 mL) containing 20.0 g (85.8 mmol) of 4-bromobiphenyl, 16.0 g (172 mmol) of anyline, 0.19 g (0.86 mmol) of palladium acetate, and 23.7 g (172 mmol) of potassium carbonate, to which 5.2 g (2.5 mmol) of tri-tert-butylphosphine (10% hexane solution) is added, is refluxed at 120° C. for ten hours. After completion of reaction, the reaction mixture is washed with water and an aqueous phase is subjected to extraction with toluene. The toluene layer is washed with saturated saline together with an organic phase, and the organic layer is dried with magnesium sulfate. Then, the mixture is subjected to suction filtration and the filtrate is condensed. The obtained residue is purified by silica gel column chromatography (developing solution: toluene). The obtained solution is condensed to obtain 13.5 g (yield: 64%) of N-(4-biphenylyl)-N-phenylamine as a white solid.

[Step 3]

A synthesis method of 2,3-bis{4[N-(4-biphenylyl)-N-phenylamino]phenyl}quinoxaline (hereinafter referred to as BPAPQ) is described. A synthesis scheme of BPAPQ is shown in (B-3).

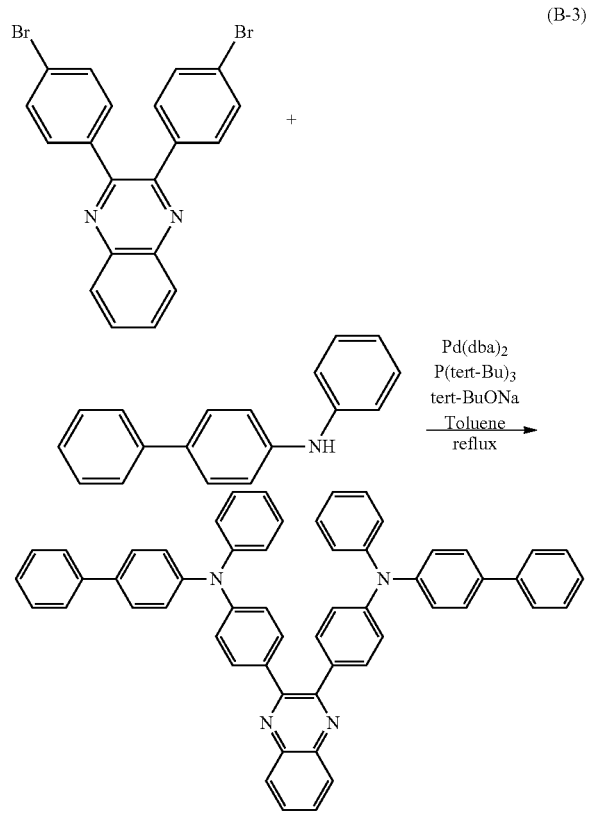

(B-3)

In a nitrogen atmosphere, a toluene suspension (80 mL) containing 5.0 g (11.4 mmol) of 2,3-bis(4-bromophenyl)quinoxaline, 6.1 g (25.0 mmol) of N-(4-biphenylyl)-N-phenylamine, 0.33 g (0.58 mmol) of bis(dibenzylidineacetone)palladium(0), and 5.5 g (56.8 mmol) of tert-butoxy sodium, to which 1.2 g (0.58 μmmol) of tri-tert-butylphosphine (10% hexane solution) is added, is heated at 80° C. for seven hours. After completion of reaction, the reaction mixture is cooled to a room temperature and the precipitate is collected by suction filtration. The obtained filtrate is dissolved in toluene, the solution is subjected to suction filtration through celite, Florisil, and alumina, and the filtrate is condensed. The obtained residue is recrystallized with chloroform and hexane to obtain 8.1 g (yield: 78%) of BPAPQ as a yellow powdered solid.

Figure 8A:
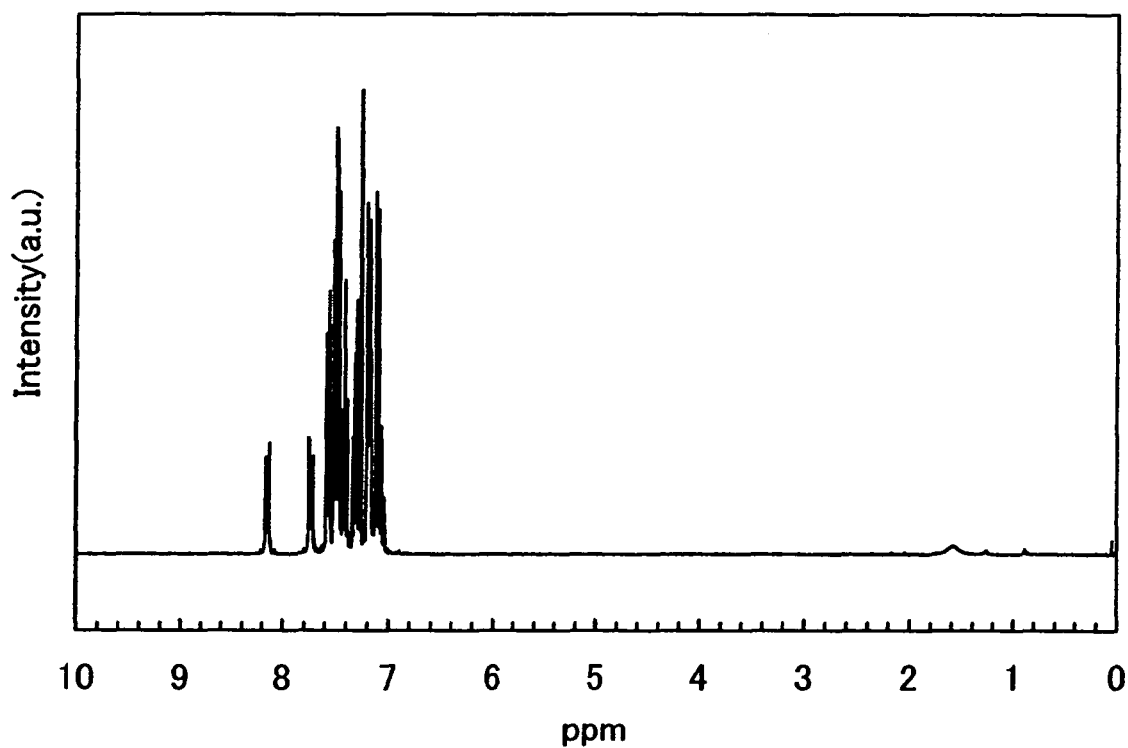
FIGS. 8A and 8B show $^1$H NMR charts of 2,3-bis{4-[N-(4-bipheniryl)-N-phenylamino]phenyl}quinoxaline, which is a quinoxaline derivative of the invention.
Figure 8B:
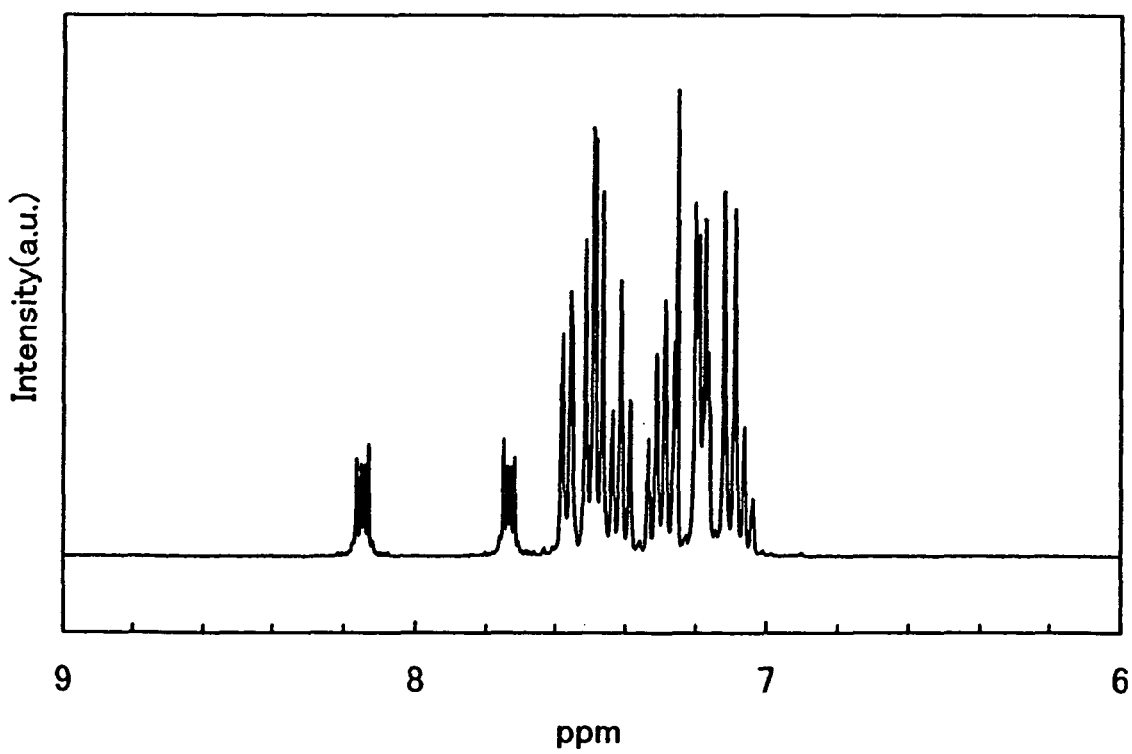

An analysis result of BPAPQ by a proton nuclear magnetic resonance spectroscopy ($^1$H NMR) is as follows. $^1$H NMR (300 MHz, CDCl$_3$); δ=8.16-8.13(m, 2H), 7.75-7.72 (m, 2H), and 7.58-7.04 (m, 36H). FIG. 8A shows an NMR chart of BPAPQ, and FIG. 8B shows an enlarged NMR chart of a part of 6 to 9 ppm.

Further, a decomposition temperature (Td) of BPAPQ is measured by a thermo-gravimetric/differential thermal analyzer (TG/DTA 320, manufactured by Seiko Instruments Inc.). Then, it is found that the Td is 436° C. and BPAPQ shows preferable heat resistance.

Figure 15:
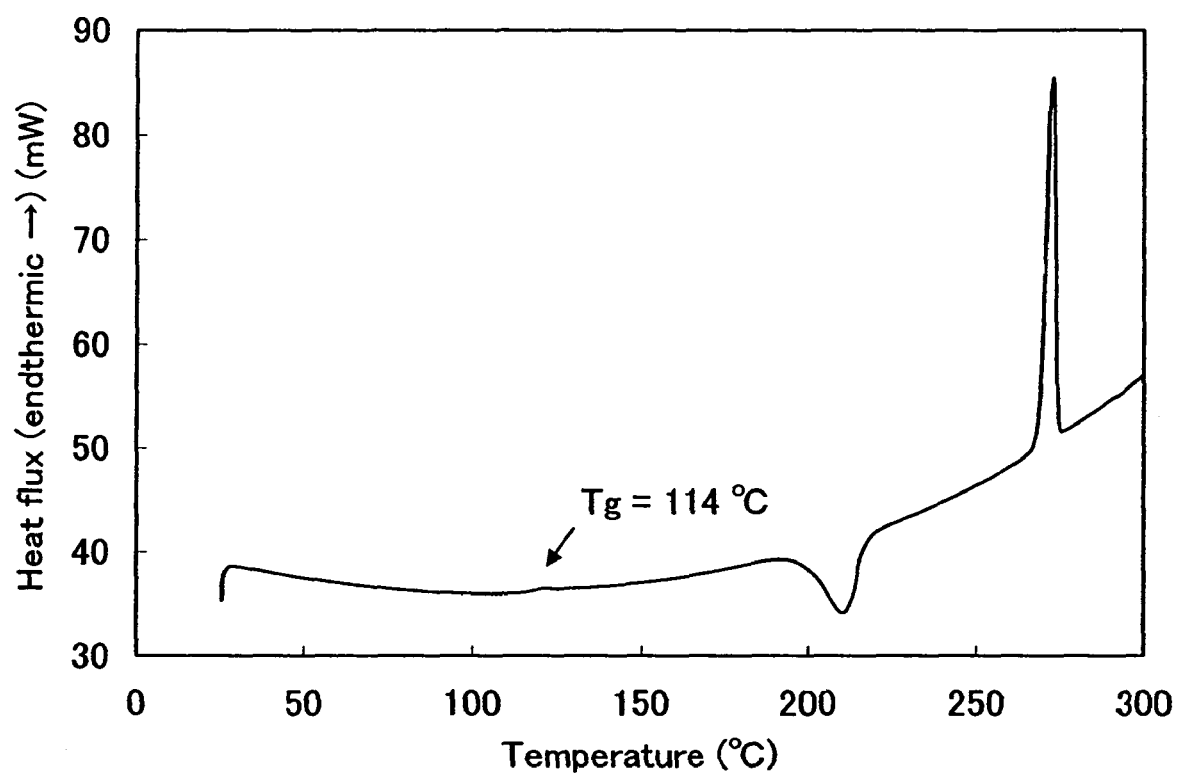
FIG. 15 shows a DSC chart of 2,3-bis{[4-N-(4-bipheniryl)-N-phenylamino]phenyl}quinoxaline, which is a quinoxaline derivative of the invention.

Further, the glass transition point is measured by a differential scanning calorimeter (DSC, Pyris 1, manufactured by Perkin Elmer Co., Ltd.). After the sample is heated to 300° C. at 40° C./min to be melted, it is cooled to a room temperature at 40° C./min. After that, the temperature is risen up to 300° C. at 10° C./min, and thus, a DSC chart shown in FIG. 15 is obtained. According to this chart, it is found that the glass transition point (Tg) of BPAPQ is 114° C. and the melting point is 268° C. Therefore, it is found that BPAPQ has a high glass transition point.

Figure 9:
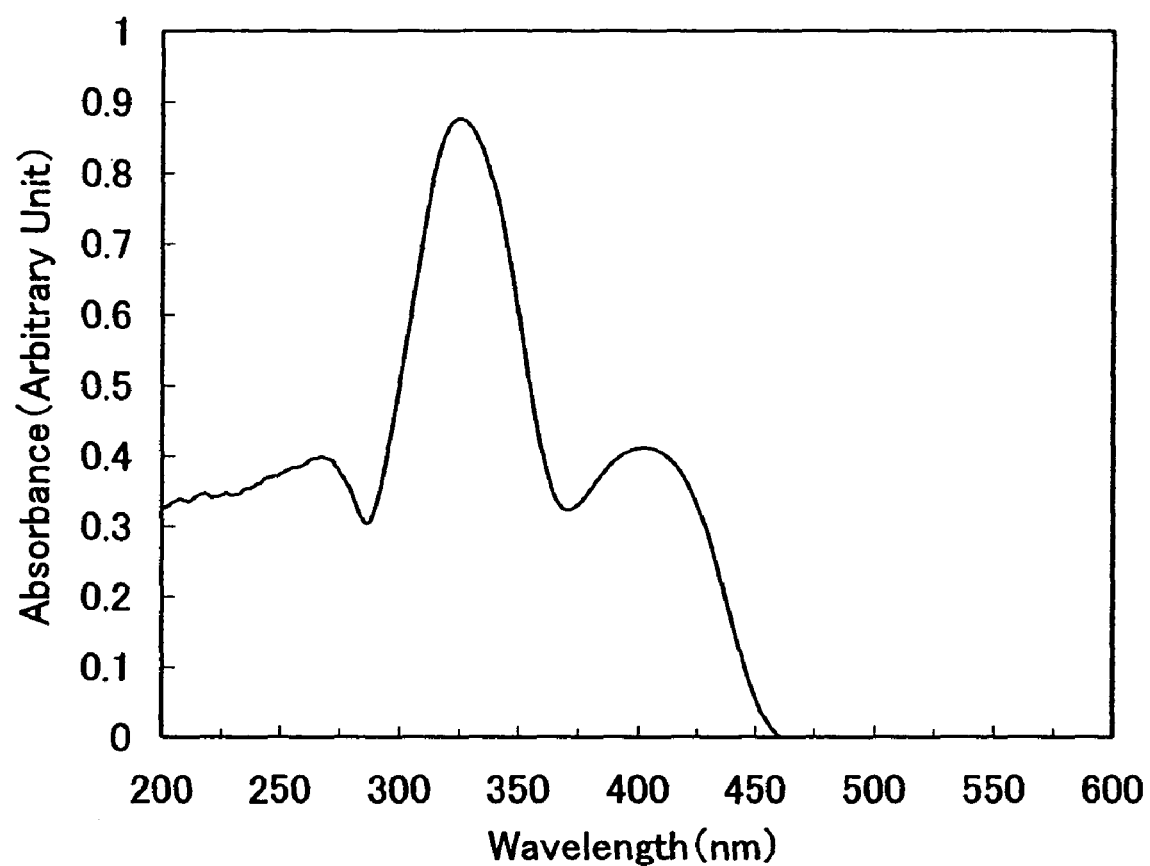
FIG. 9 is a graph showing an absorption spectrum of 2,3-bis{4-[N-(4-bipheniryl)-N-phenylamino]phenyl}quinoxaline in a toluene solution, which is a quinoxaline derivative of the invention.
Figure 10:
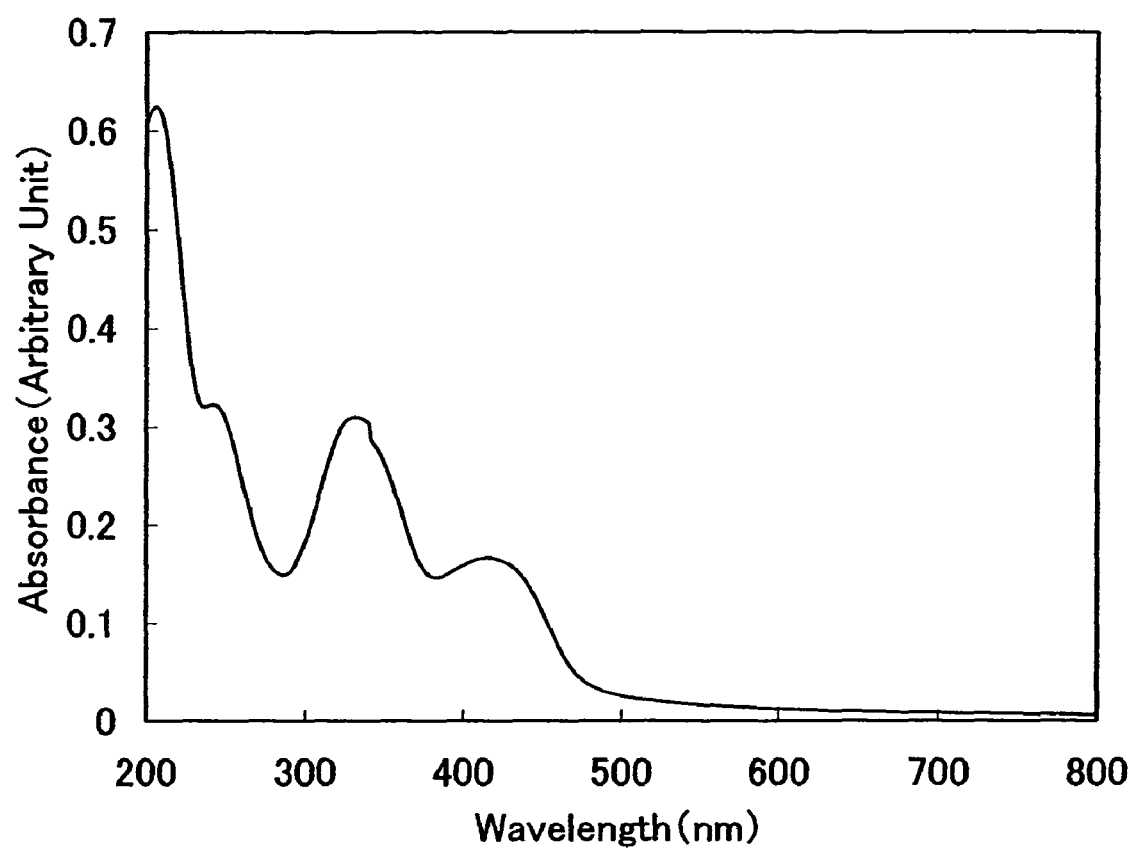
FIG. 10 is a graph showing an absorption spectrum of a thin film of 2,3-bis{4-[N-(4-bipheniryl)-N-phenylamino]phenyl}quinoxaline, which is a quinoxaline derivative of the invention.

FIG. 9 shows an absorption spectrum of the toluene solution of BPAPQ, and FIG. 10 shows an absorption spectrum of a thin film of BPAPQ. According to FIGS. 9 and 10, it is found that peaks are at 325 nm and 402 nm in the case of the toluene solution, and at 328 nm and 418 nm in the case of the thin film state.

Figure 11:
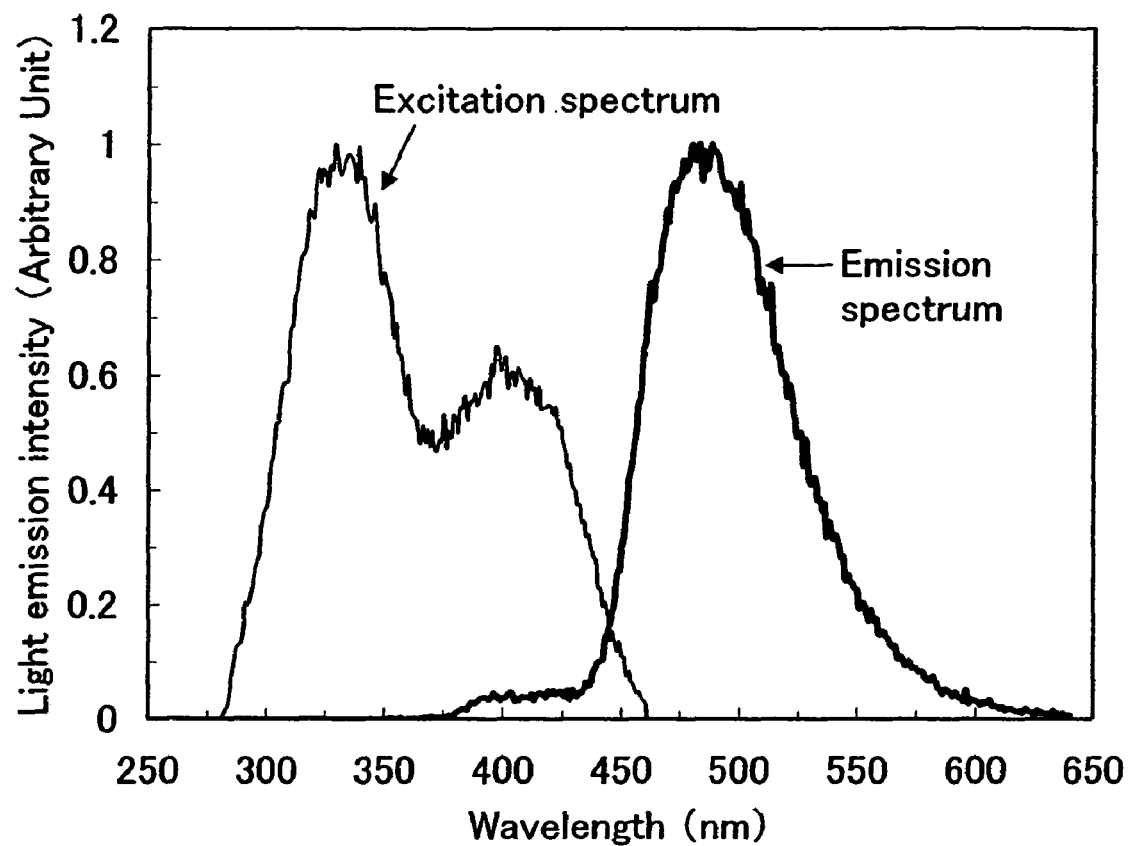
FIG. 11 is a graph showing an excitation spectrum and a light emission spectrum of 2,3-bis{4-[N-(4-bipheniryl)-N-phenylamino]phenyl}quinoxaline in a toluene solution, which is a quinoxaline derivative of the invention.
Figure 12:
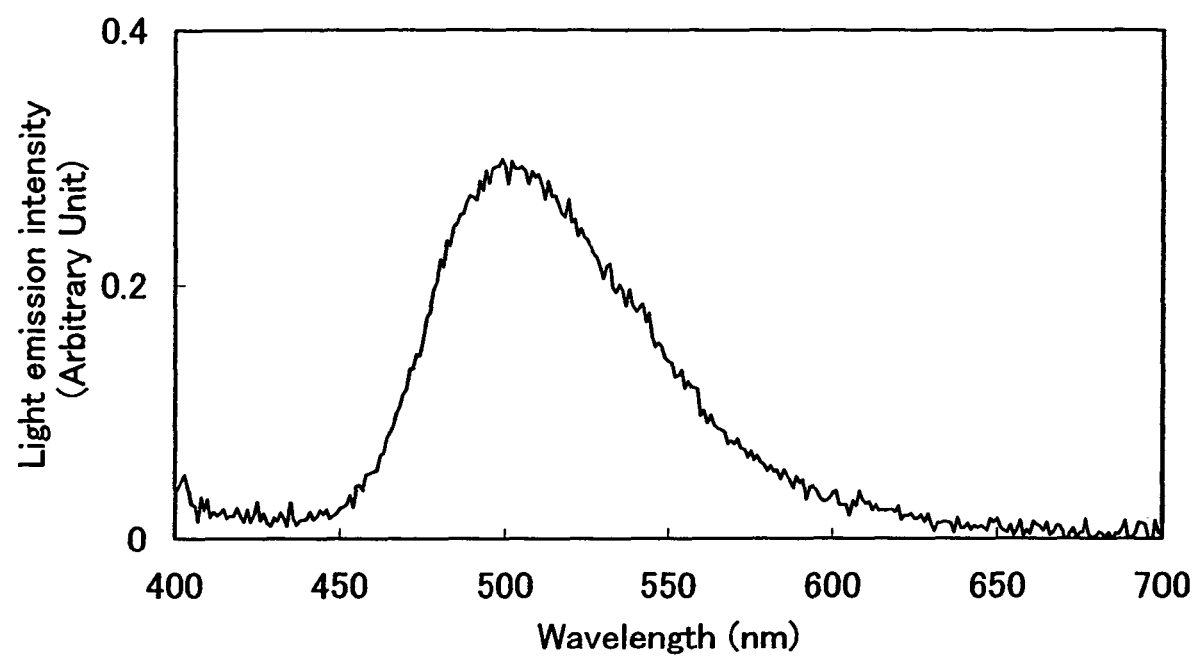
FIG. 12 is a graph showing a light emission spectrum of a thin film of 2,3-bis{4-[N-(4-bipheniryl)-N-phenylamino]phenyl}quinoxaline, which is a quinoxaline derivative of the invention.

FIG. 11 shows a light emission spectrum and an excitation spectrum of the toluene solution of BPAPQ. According to FIG. 11, it is found that the light emission maximum is at 483 nm in the toluene solution. FIG. 12 shows a light emission spectrum of a thin film (solid state) of BPAPQ excited by ultraviolet rays having a wavelength of 365 nm. According to FIG. 12, the light emission maximum is at 499 nm in the solid state. Therefore, it is found that there is no significant difference in light emission maximum between the toluene solution and the solid state. That is, BPAPQ hardly assembles in the solid state due to a twist form of a biphenyl skeleton, and even in the case of the solid state, a short wavelength light emission can be obtained similarly to a light emission color in the case of the solution state.

A HOMO level in the thin film state is measured by photoelectron spectroscopy (AC-2, manufactured by Riken Keiki Co., Ltd.) in atmospheric air. The measurement result is −5.31 eV. Further, an optical energy gap is obtained from a Tauc plot assuming direct transition by using the data of the absorption spectrum in FIG. 10. The energy gap is 2.66 eV Therefore, a LUMO level is −2.65 eV.

Further, electrochemical stability of BPAPQ is evaluated by a cyclic voltammetry (CV). An electrochemical analyzer (AILS model 600A, manufactured by BAS Inc.) is used as a measurement device. As for a solution used in the CV measurement, dehydrated dimethylformamide (DMF) is used as a solvent. Tetraperchlorate-n-butylammonium (n-Bu$_4$NClO$_4$), a supporting electrolyte, is dissolved in the solvent so as to have a concentration of 100 mM. Also, BPAPQ, an object to be measured, is dissolved therein such that the concentration thereof is set to be 1 mM. Further, a platinum electrode (PTE platinum electrode, manufactured by BAS Inc.) is used as a work electrode. A platinum electrode (VC-3 Pt counter electrode (5 cm), manufactured by BAS Inc.) is used as an auxiliary electrode. An Ag/Ag$^+$ electrode (RE 5 nonaqueous reference electrode, manufactured by BAS Inc.) is used as a reference electrode. The scanning speed is set to be 0.1 V/sec, and 100 cycle CV measurements are carried out for both an oxidation reaction and a reduction reaction.

Figure 13:
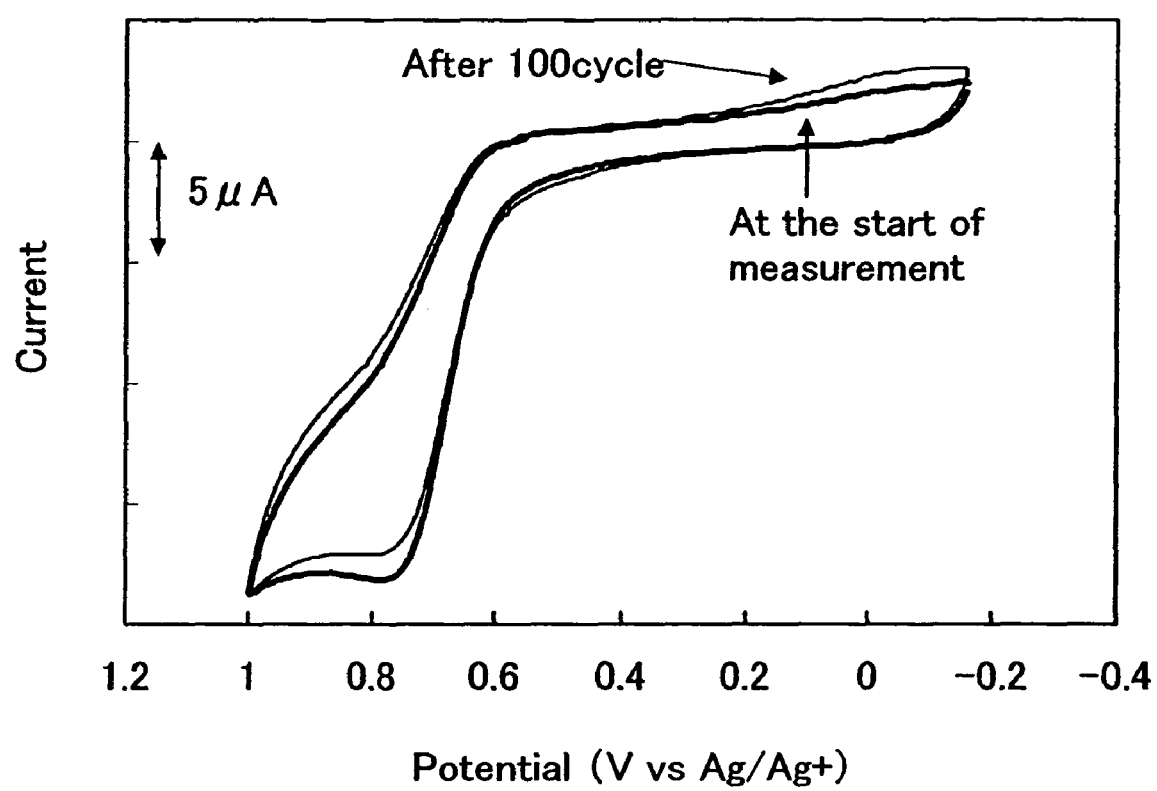
FIG. 13 is a graph showing an oxidation reaction characteristic of 2,3-bis{4-[N-(4-bipheniryl)-N-phenylamino]phenyl}quinoxaline, which is a quinoxaline derivative of the invention measured by CV measurement.
Figure 14:
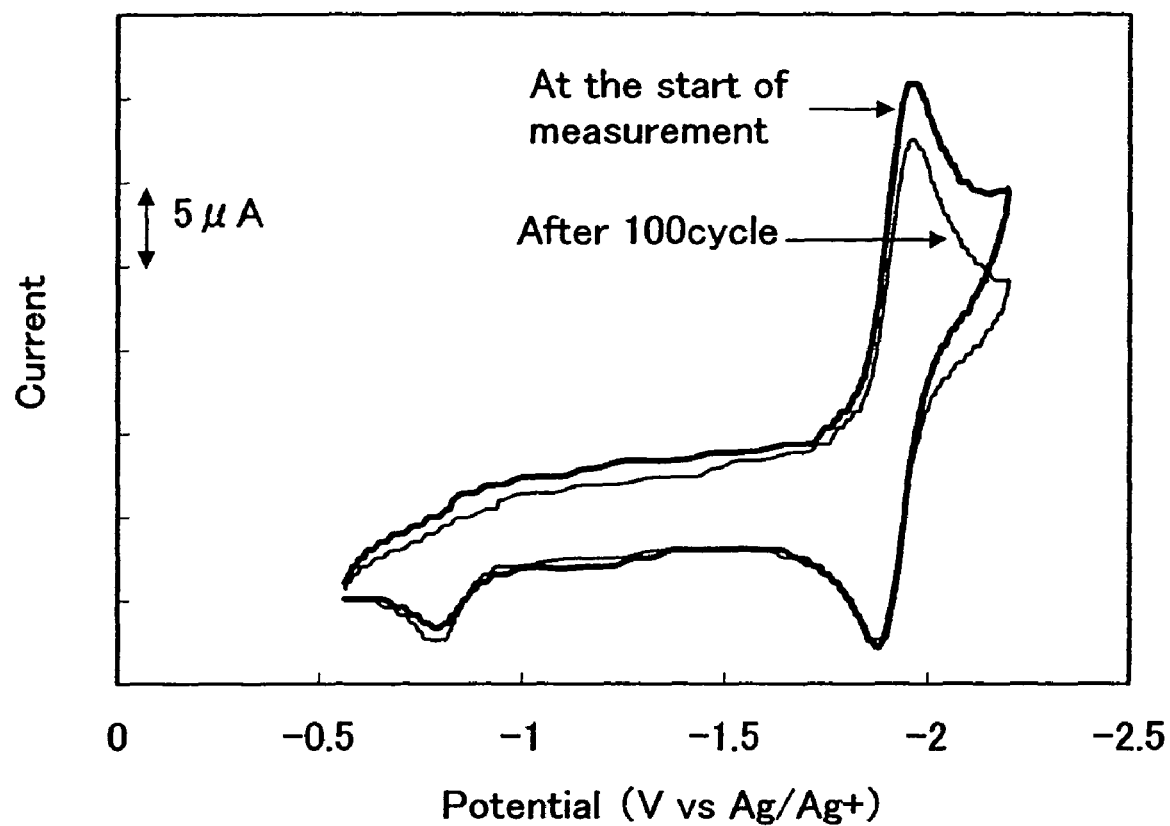
FIG. 14 is a graph showing a reduction reaction characteristic of 2,3-bis{4-[N-(4-bipheniryl)-N-phenylamino]phenyl}quinoxaline, which is a quinoxaline derivative of the invention measured by CV measurement.

FIG. 13 shows an oxidation reaction characteristic of BPAPQ measured by CV measurement, and FIG. 14 shows a reduction reaction characteristic of BPAPQ measured by CV measurement. It is found that a reversible peak is obtained in both the oxidation reaction and the reduction reaction. Further, even when oxidation or reduction is repeated 100 times, a cyclic voltamogram hardly changes. This means that BPAPQ is stable with respect to oxidation and reduction, that is, electrochemically stable.

Embodiment 2

In this embodiment, a synthesis example of 2,3-bis{4-[N,N-di(4-bipheniryl)amino]phenyl}quinoxaline (hereinafter referred to as BBAPQ), which is the quinoxaline derivative of the invention expressed by the following structure formula (39), is specifically shown.

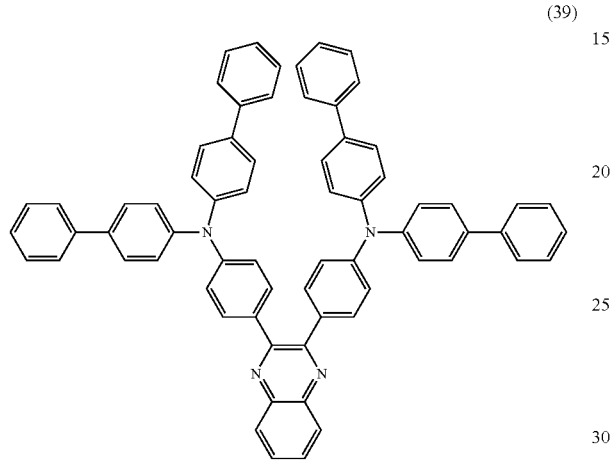

[Step 1]
A synthesis method of N,N-bis(4-bromophenyl)amine is described. A synthesis scheme of N,N-bis(4-bromophenyl) amine is shown in (C-1).

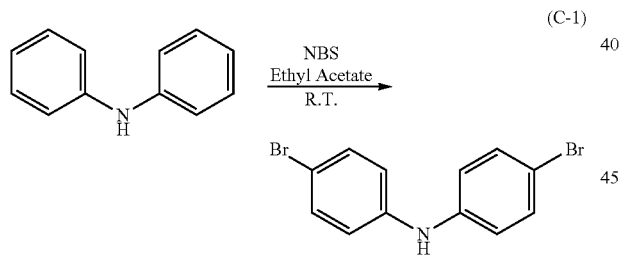

An ethyl acetate solution (400 mL) containing 10 g (59 mmol) of diphenylamine, to which 22.1 g (124 mmol) of N-bromo succinimide is added, is stirred for 16 hours at room temperature. After completion of reaction, the reaction mixture is washed with water and an aqueous phase is subjected to extraction with ethyl acetate. The extraction solution is mixed with an organic phase. After the obtained organic phase is washed with saturated saline, the organic phase is dried with magnesium sulfate. Then, the mixture is subjected to suction filtration and the filtrate is condensed. The obtained residue is washed with hexane, a hexane suspension is subjected to suction filtration to collect a solid. Accordingly, 9.5 g (yield: 49%) of N,N-bis(4-bromophenyl)amine is obtained as a white solid.

[Step 2]
A synthesis method of N,N-di(4-biphenylyl)amine is described. A synthesis scheme of N,N-di(4-biphenylyl) amine is shown in C-2.

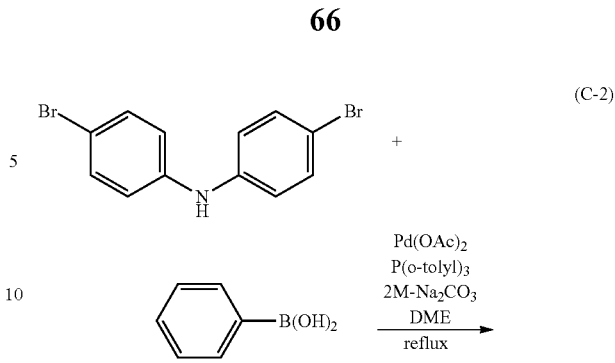

In a nitrogen atmosphere, an ethylene glycol dimethyl ether (20 mL) solution containing 9.5 g (29 mmol) of N,N-bis(4-bromophenyl)amine, 7.9 g (65 mmol) of phenyl boronic acid, 0.15 g (0.646 mmol) of palladium acetate, and 1.4 g (4.5 mmol) of tris(o-thryl)phosphine, to which 95 mL of a potassium carbonate solution (2.0 mol/L) is added, is rectified at 90° C. for seven hours. After completion of reaction, the reaction mixture is filtrated, and the obtained solid is recrystallized with chloroform and hexane to obtain 6.7 g (yield: 72%) of N,N-di(4-biphenylyl)amine which is an object as a white powdered solid.

[Step 3]
A synthesis method of 2,3-bis{4-[N,N-di(4-bipheniryl) amino]phenyl}quinoxaline (hereinafter referred to as BBAPQ) is described. A synthesis scheme of BBAPQ is shown in (C-3).

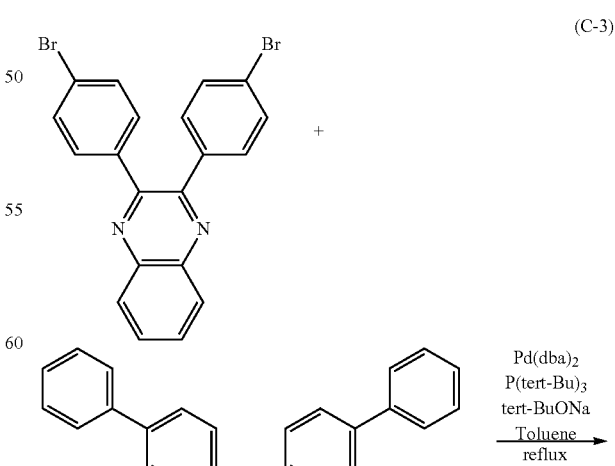

-continued

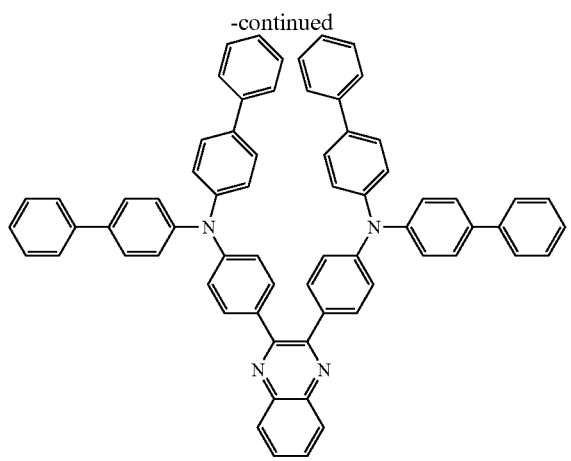

In a nitrogen atmosphere, a toluene suspension (80 mL) containing 3.0 g (8.1 mmol) of 2,3-bis(4-bromophenyl)quinoxaline which is synthesized in the step 1 of Embodiment 1, 5.7 g (18 mmol) of N,N-di(4-biphenylyl)amine, 0.23 g (0.41 mmol) of bis(dibenzylidineacetone)palladium(0), and 3.9 g (41 mmol) of tert-butoxy sodium, to which 0.082 g (0.41 mmol) of tri-tert-butylphosphine is added, is heated at 80° C. for eight hours. After completion of reaction, the reaction mixture is subjected to suction filtration, the obtained solid is dissolved in chloroform, the solution is subjected to suction filtration through celite, Florisil, and alumina. Then, the filtrate is condensed. The obtained residue is recrystallized with chloroform and hexane to obtain 5.7 g (yield: 76%) of BBAPQ which is an object, as an yellow solid.

Figure 16A:
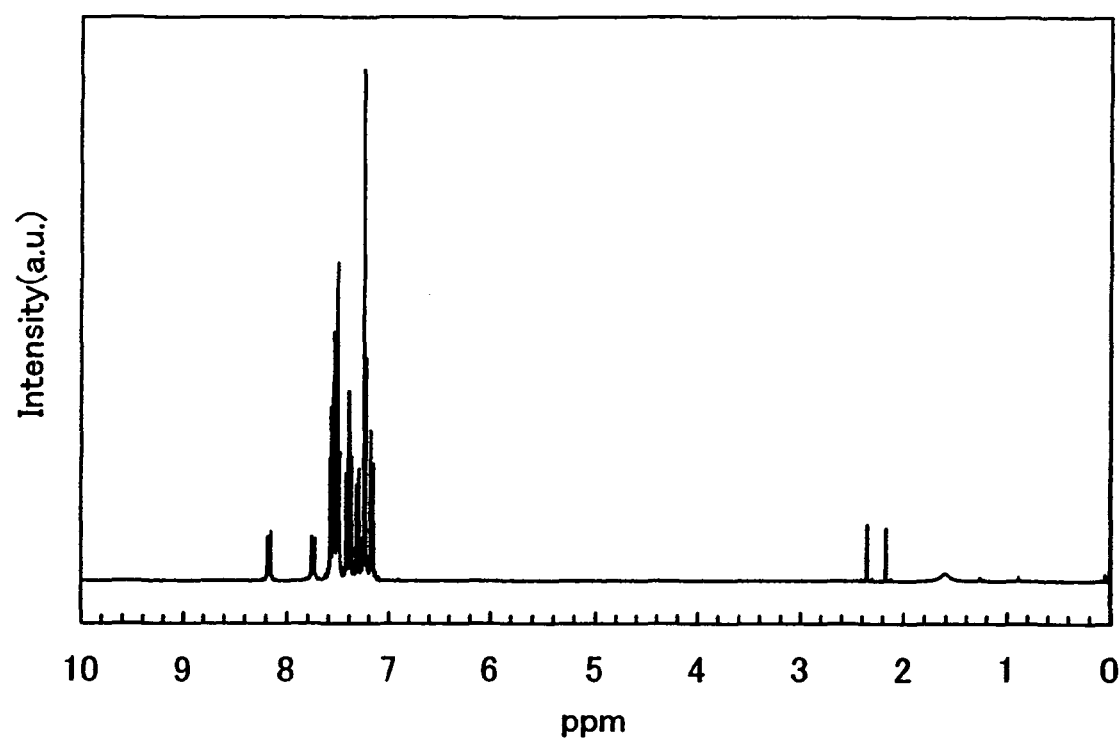
FIGS. 16A and 16B show $^1$H NMR charts of 2,3-bis{4-[N,N-di(4-bipheniryl)amino]phenyl}quinoxaline, which is a quinoxaline derivative of the invention.
Figure 16B:
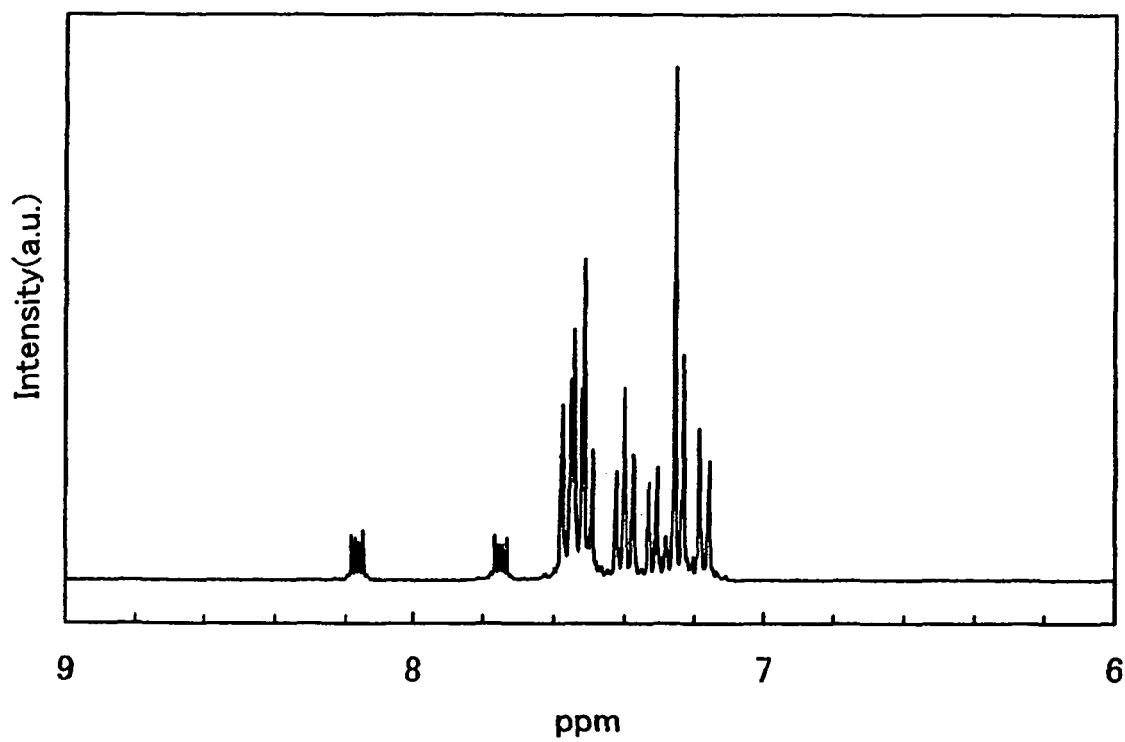

An analysis result of BBAPQ by a proton nuclear magnetic resonance spectroscopy ($^1$H NMR) is as follows. $^1$H NMR (300 MHz, CDCl$_3$); δ=8.18-8.15 (m, 2H), 7.76-7.73 (m, 2H), and 7.58-7.16 (m, 44H). FIG. 16A shows an NMR chart of BBAPQ, and FIG. 16B shows an enlarged NMR chart of a part of 6 to 9 ppm.

A decomposition temperature (Td) of BBAPQ is measured by a thermo-gravimetric/differential thermal analyzer (TG/DTA 320, manufactured by Seiko Instruments Inc.). Then, it is found that the Td is 486° C. and BBAPQ shows preferable heat resistance.

Figure 23:
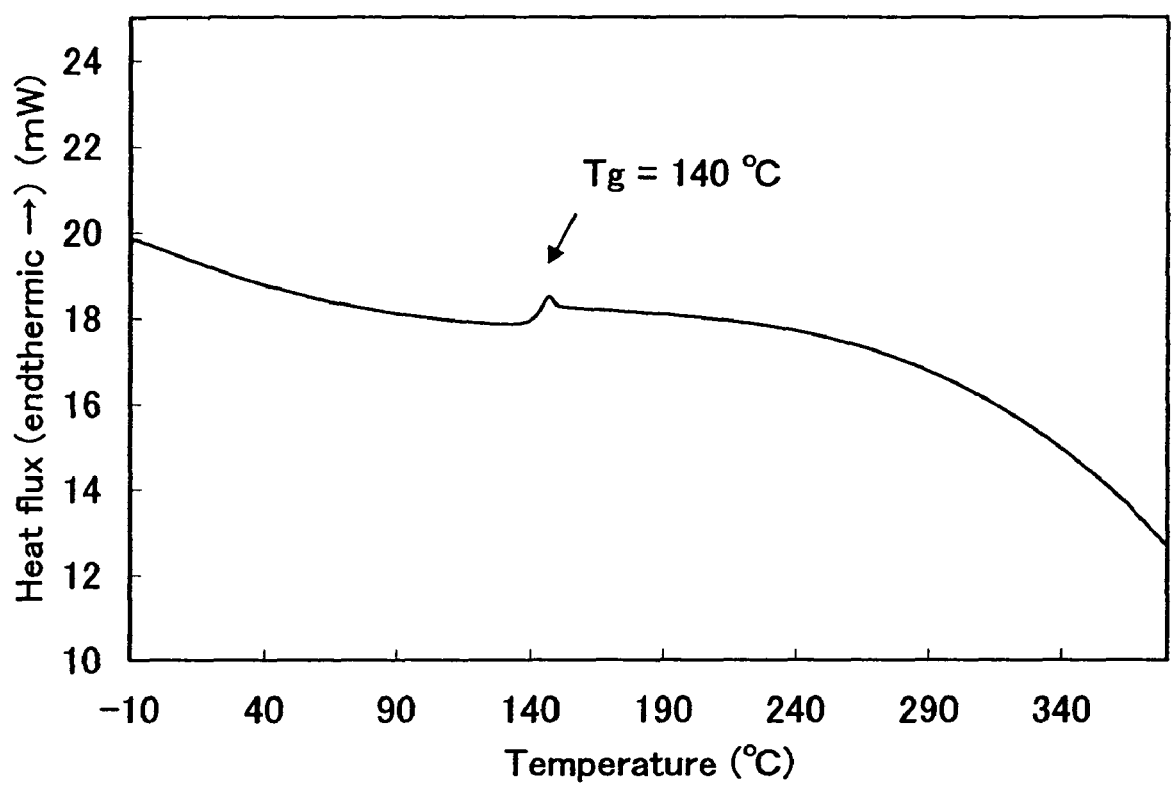
FIG. 23 shows a DSC chart of 2,3-bis{4-[N,N-di(4-bipheniryl)amino]phenyl}quinoxaline, which is a quinoxaline derivative of the invention.

Further, the glass transition point is measured by a differential scanning calorimeter (DSC, Pyris 1, manufactured by Perkin Elmer Co., Ltd.). After the sample is heated to 380° C. at 40° C./min to be melted, it is cooled to −10° C. at 40° C./min. After that, the temperature is risen up to 380° C. at 10° C./min, and thus, a DSC chart shown in FIG. 23 is obtained. According to this chart, it is found that the glass transition point (Tg) of BBAPQ is 140° C. Note that it is known that the melting point is 321° C. from the DSC chart of the case where the sample is melted first. Therefore, it is found that BBAPQ has a high glass transition point.

Figure 17:
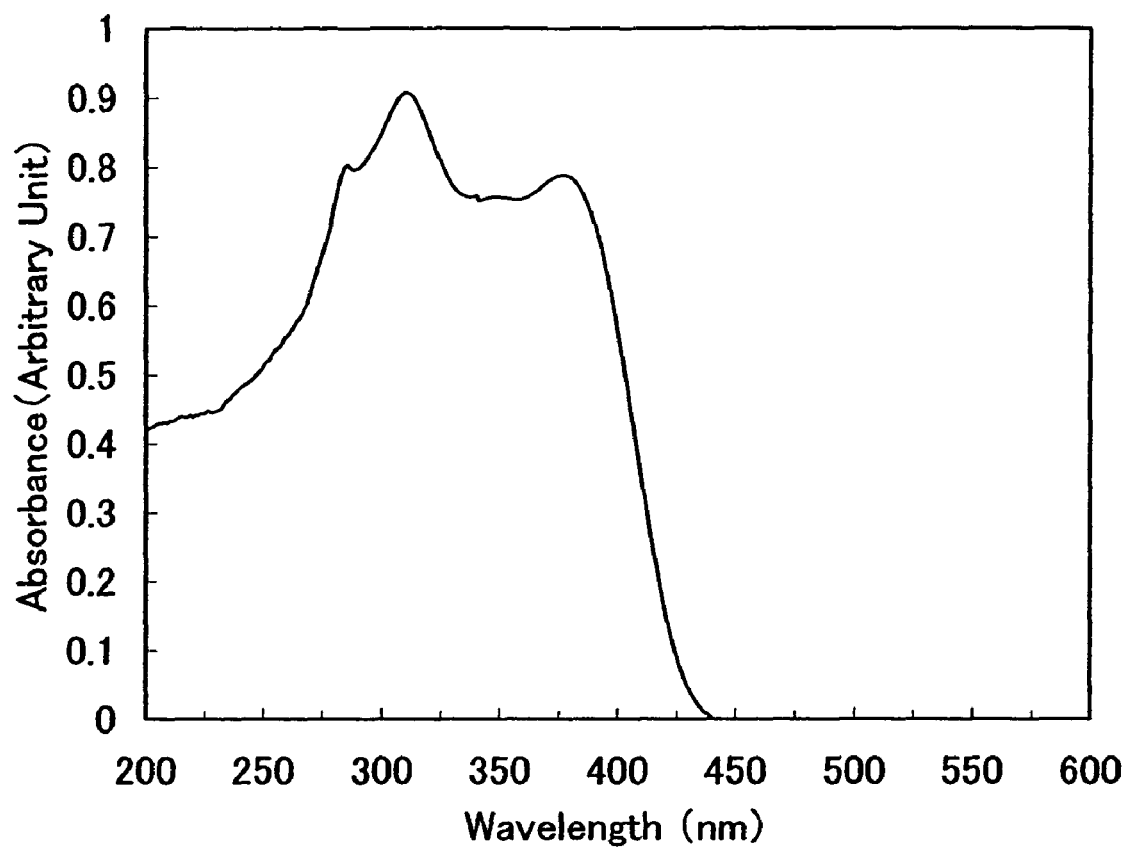
FIG. 17 is a graph showing an absorption spectrum of 2,3-bis{4-[N,N-di(4-bipheniryl)amino]phenyl}quinoxaline in a toluene solution, which is a quinoxaline derivative of the invention.

FIG. 17 shows an absorption spectrum of the toluene solution of BBAPQ. According to FIG. 17, it is found that peaks are at 305 nm and 375 nm in the case of the toluene solution.

Subsequently, electrochemical stability of BBAPQ is evaluated. The evaluation method is similar to that of electrochemical stability of BPAPQ, which is described in Embodiment 1.

Figure 21:
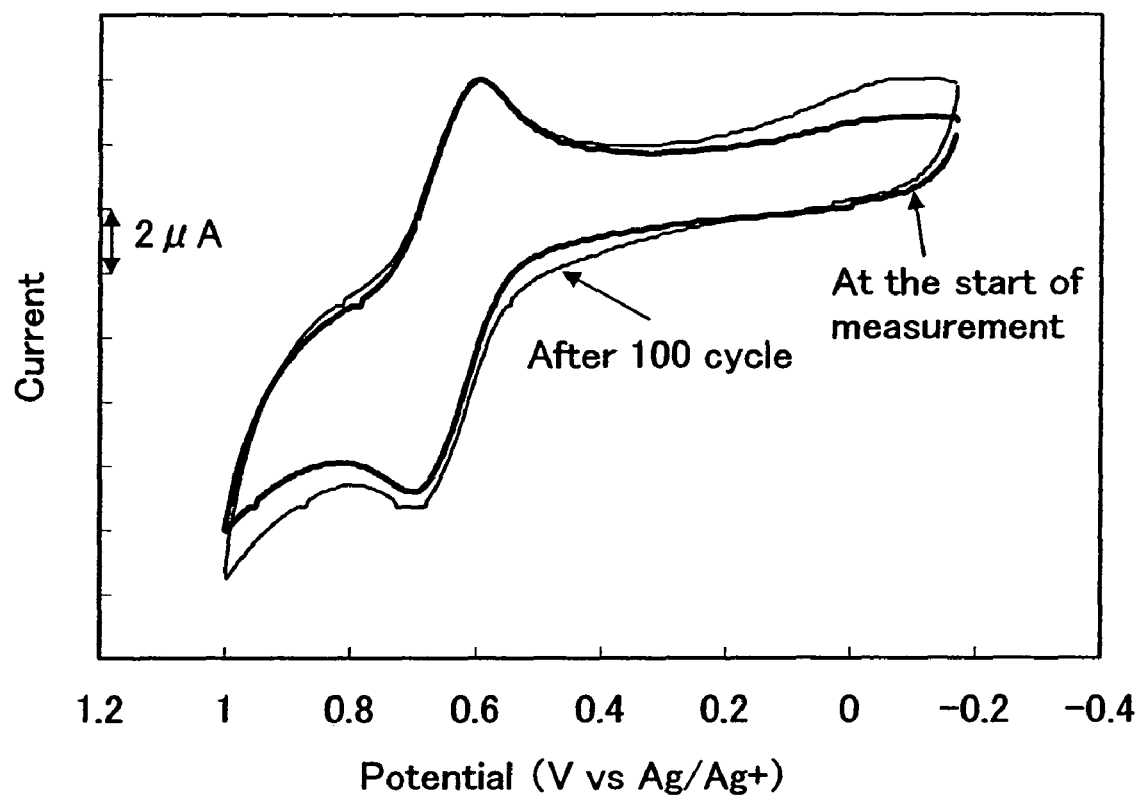
FIG. 21 is a graph showing an oxidation reaction characteristic of 2,3-bis{4-[N,N-di(4-bipheniryl)amino]phenyl}quinoxaline, which is a quinoxaline derivative of the invention measured by CV measurement.
Figure 22:
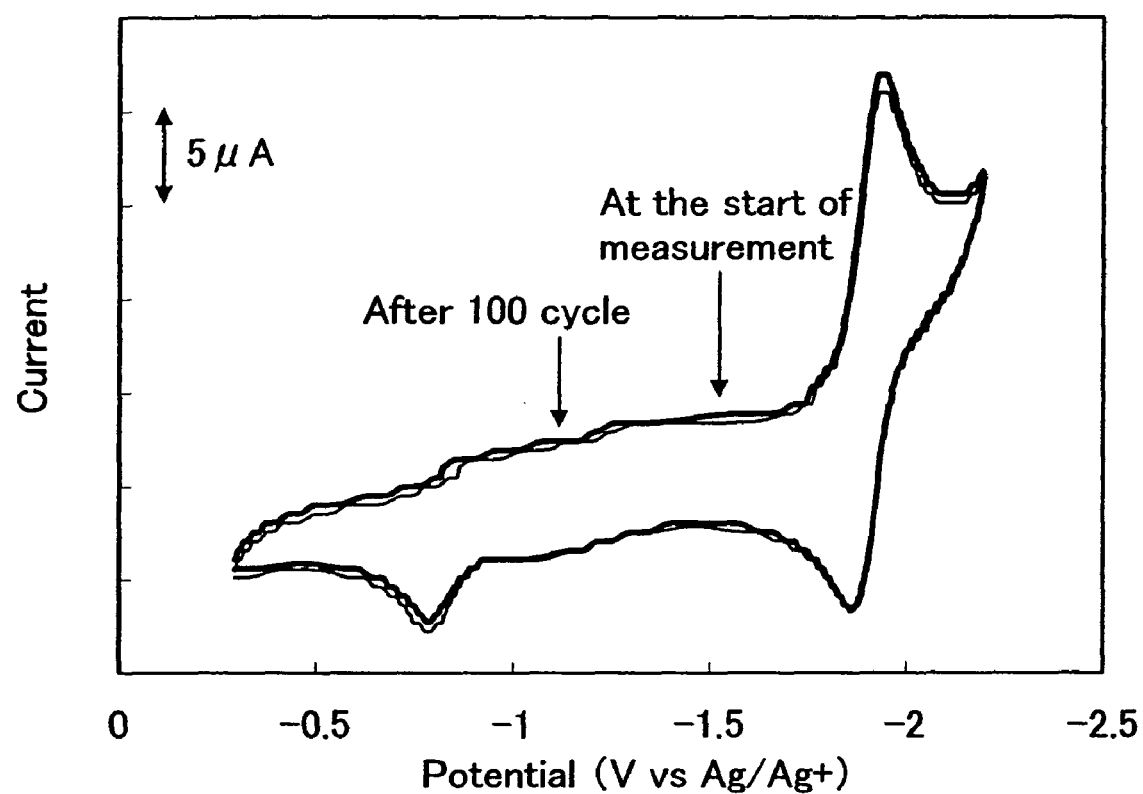
FIG. 22 is a graph a reduction reaction characteristic of 2,3-bis{4-[N,N-di(4-phenylphenyl)]amino}phenyl-1,4-quinoxaline, which is a quinoxaline derivative of the invention measured by CV measurement.

FIG. 21 shows an oxidation reaction characteristic of BBAPQ measured by CV measurement, and FIG. 22 shows a reduction reaction characteristic of BBAPQ measured by CV measurement. It is found that a reversible peak is obtained in both the oxidation reaction and the reduction reaction. Further, even when oxidation or reduction is repeated 100 times, a cyclic voltamogram hardly changes. This means that BBAPQ is stable with respect to oxidation and reduction, that is, electrochemically stable.

Embodiment 3

Figure 37:
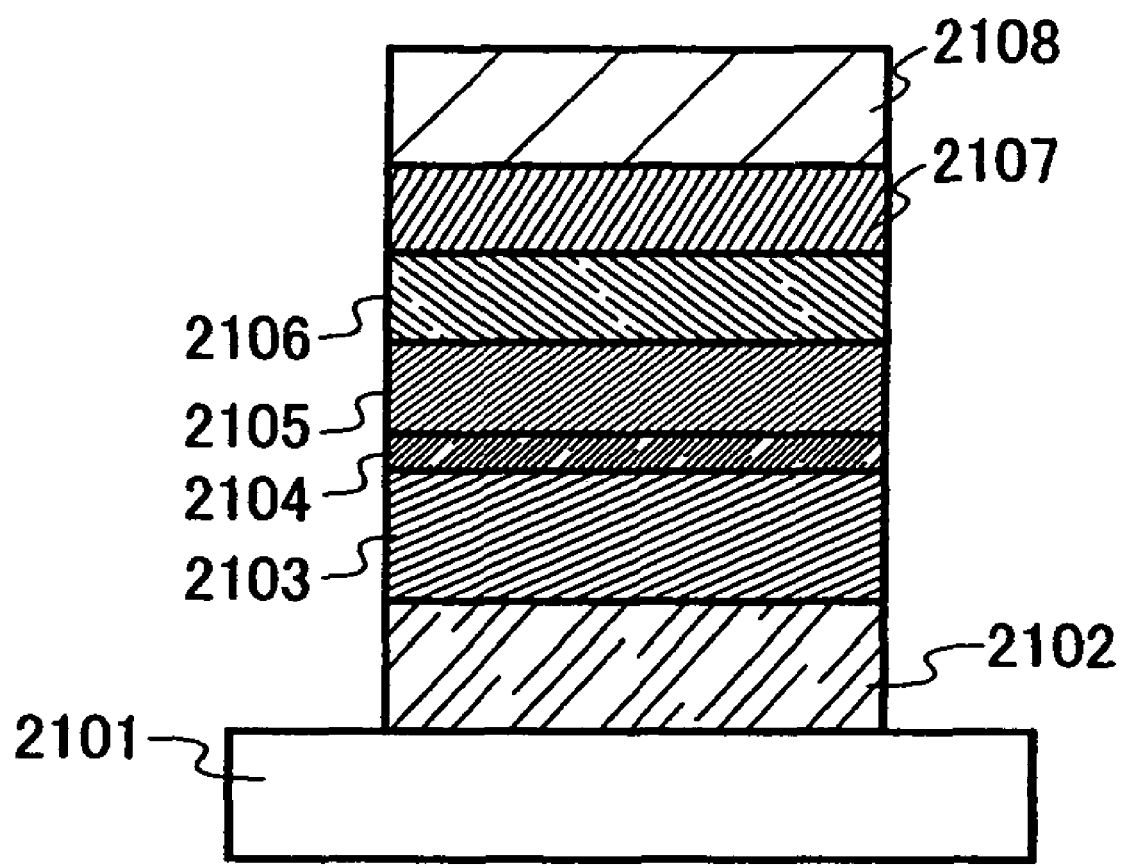
FIG. 37 is a view showing a light emitting element of the invention.

In this embodiment, the light emitting element of the invention is described with reference to FIG. 37.

Indium tin oxide containing silicon oxide is formed over a glass substrate 2101 by sputtering as a first electrode 2102. The film thickness of the first electrode is 110 nm and the area thereof is 2 mm×2 mm.

The substrate provided with the first electrode is fixed on a substrate holder which is provided in a vacuum evaporation apparatus, in such a way that a surface provided with the first electrode faces downward. After that, the air inside the vacuum evaporation apparatus is evacuated to approximately $10^{-4}$ Pa. Then, a layer including a composite material 2103 is formed over the first electrode 2102 by co-evaporation of NPB and molybdenum oxide (VI). The film thickness is 50 nm and the weight ratio between NPB and molybdenum oxide (VI) is adjusted to be 4:1 (=NPB:molybdenum oxide). It is to be noted that the co-evaporation is an evaporation method by which evaporation is carried out simultaneously from a plurality of evaporation sources each holding a different material in one process chamber.

Then, a hole transporting layer 2104 is formed over the layer including the composite material 2103 to have a thickness of 10 nm using NPB by evaporation with resistive heating.

Further, a light emitting layer 2105 is formed over the hole transporting layer 2104 to have a thickness of 30 nm by co-evaporation of 2,3-bis{4-[N-(4-bipheniryl)-N-phenylamino]phenyl}quinoxaline (hereinafter referred to as BPAPQ) which is the quinoxaline derivative of the invention expressed by the structure formula (14) and (acetylacetonate)bis[2,3-bis(4-fluorophenyl)quinoxalinato]iridium(III) (hereinafter referred to as Ir(Fdpq)$_2$(acac)) which is expressed by the structure formula (114). Here, the weight ratio between BPAPQ and Ir(Fdpq)$_2$(acac) is adjusted to be 1:0.1 (=BPAPQ:Ir(Fdpq)$_2$(acac)). Consequently, Ir(Fdpq)$_2$(acac) is dispersed in the layer containing BPAPQ.

After that, an electron transporting layer 2106 is formed over the light emitting layer 2105 by depositing Alq so as to have a thickness of 10 nm by evaporation with resistive heating.

Further, an electron injecting layer 2107 is formed over the electron transporting layer 2106 so as to have a thickness of 50 nm by co-evaporation of Alq and lithium. The weight ratio between Alq and lithium is adjusted to be 1:0.01 (=Alq:lithium). Consequently, lithium is dispersed in a layer containing Alq.

Finally, a second electrode 2108 is formed over the electron injecting layer 2107 by depositing aluminum so as to have a thickness of 200 nm by evaporation with resistive heating. Thus, the light emitting element of Embodiment 3 is formed.

Figure 18:
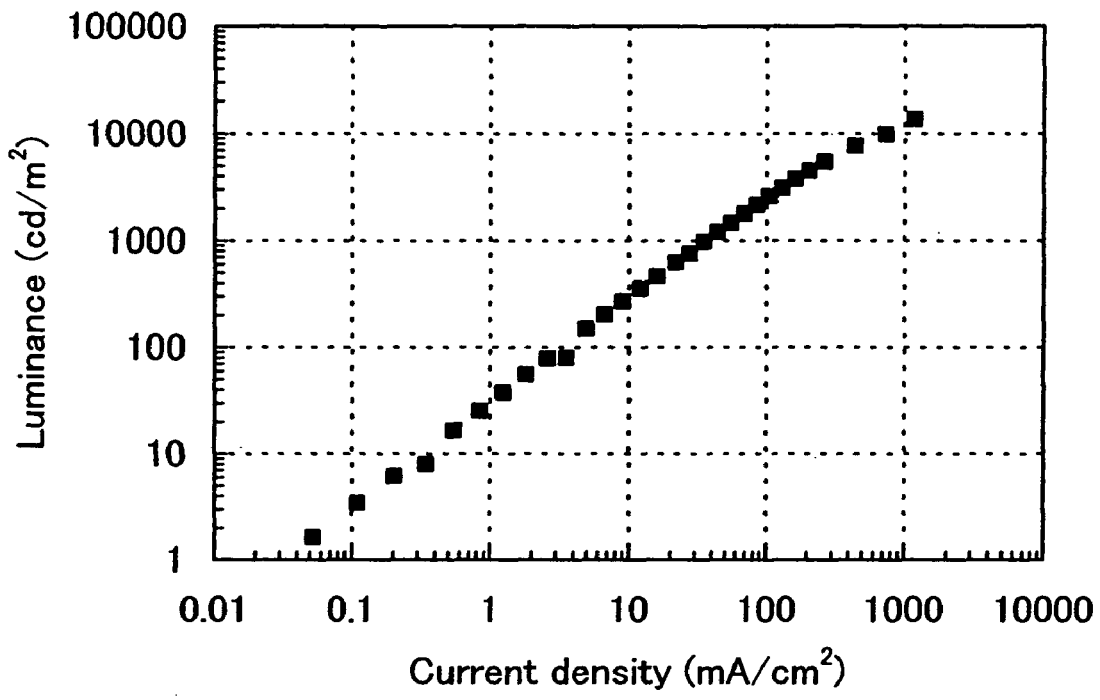
FIG. 18 is a graph showing current density-luminance characteristics of a light emitting element in Embodiment 3.
Figure 19:
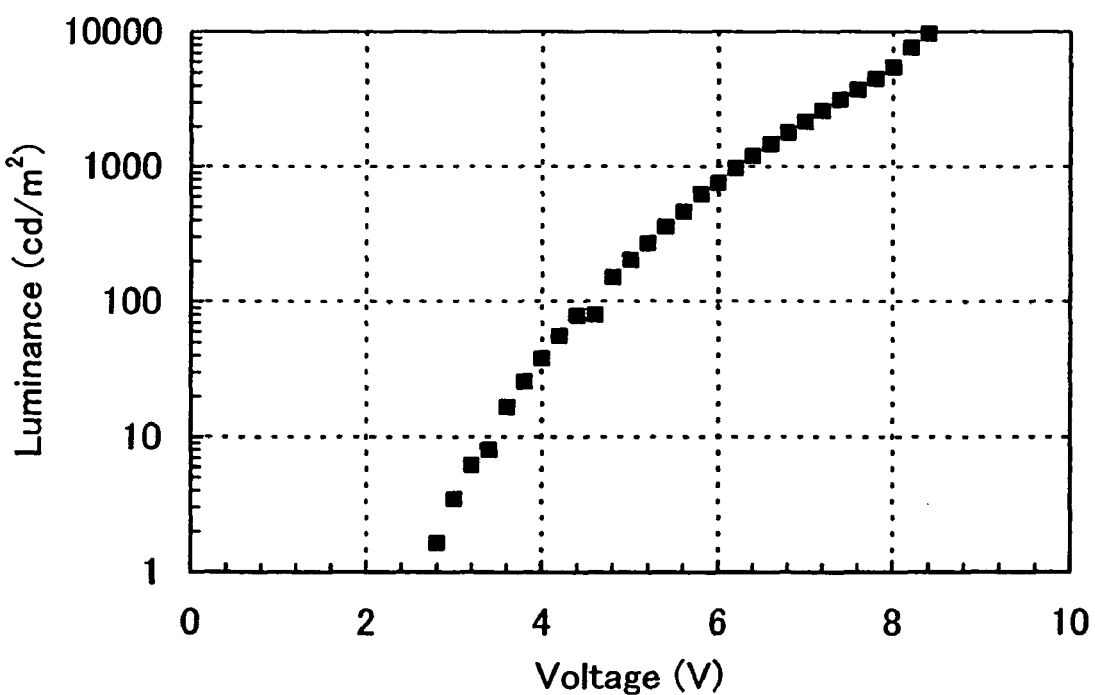
FIG. 19 is a graph showing voltage-luminance characteristics of the light emitting element in Embodiment 3.
Figure 20:
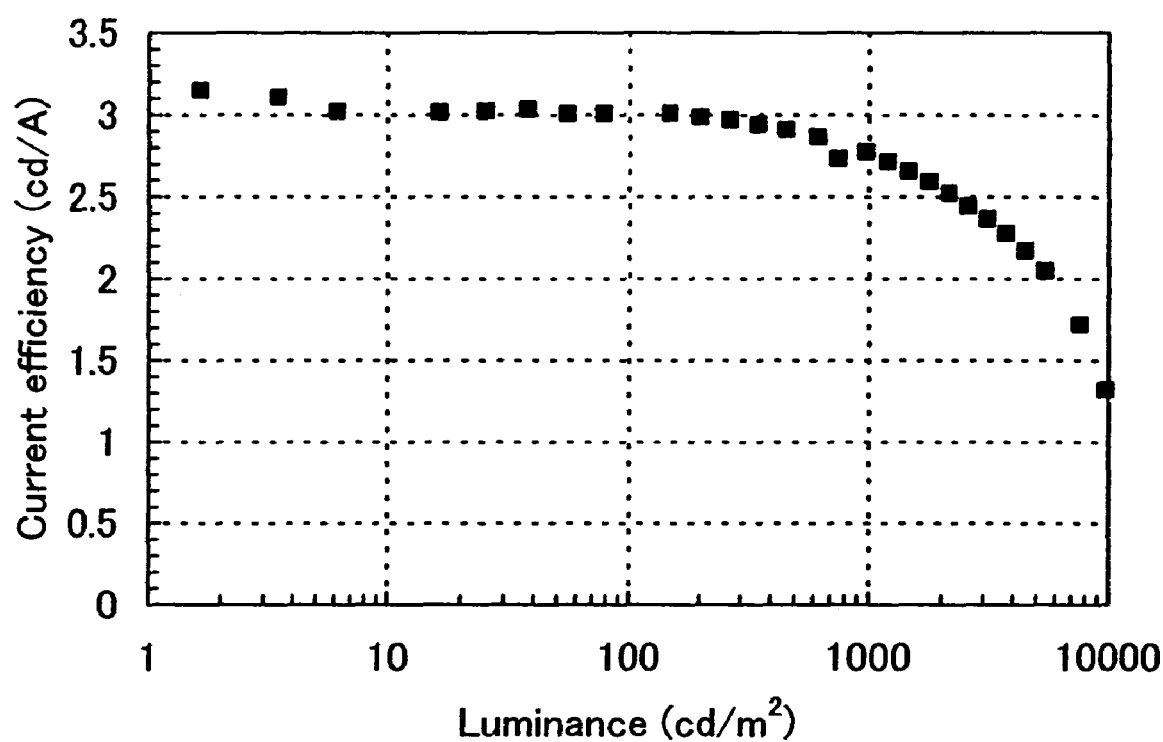
FIG. 20 is a graph showing luminance-current efficiency characteristics of the light emitting element in Embodiment 3.
Figure 33:
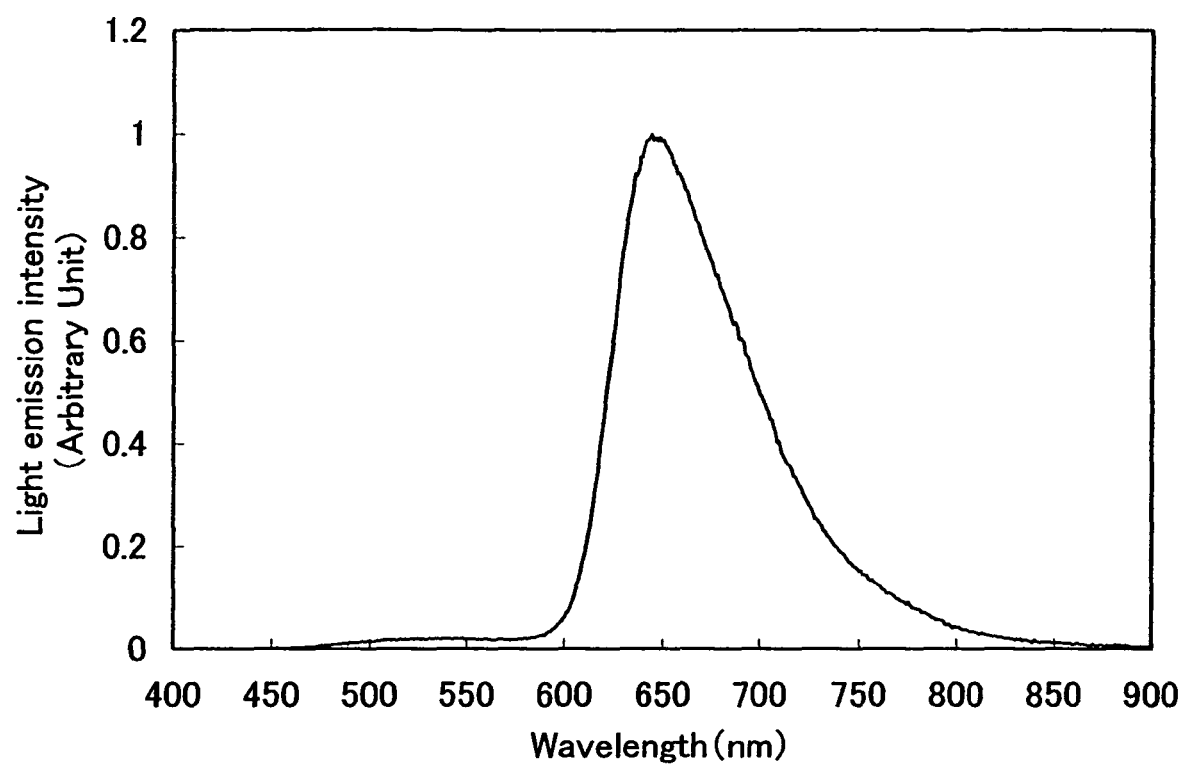
FIG. 33 is a graph showing a light emission spectrum of the light emitting element in Embodiment 3.

Current density-luminance characteristics of the light emitting element of Embodiment 3 are shown in FIG. 18. Luminance-voltage characteristics thereof are shown in FIG. 19. Current efficiency-luminance characteristics thereof are shown in FIG. 20. Also, a light emission spectrum upon applying a current of 1 mA through the light emitting element is shown in FIG. 33. In the light emitting element of Embodiment 3, the voltage required for obtaining a luminance of 970 cd/m$^2$ is 6.2 V. The current flowing through the light emitting element in this case is 1.40 mA (the current density is 34.9 mA/cm$^2$). The CIE chromaticity coordinates are (x=0.66, y=0.32). In addition, the current efficiency and the power efficiency in this case are 2.8 cd/A and 1.41 m/W respectively.

As described above, a red light emitting element consuming low power can be formed by combining the quinoxaline derivative of the invention and the organometallic complex.

Further, a light emitting element having the same structure as the above light emitting element is formed and initial luminance is set to be 1000 cd/m$^2$. Under such a condition, a continuous lighting test is carried out by constant current driving. Then, it is found that the light emitting element still holds 82% of the initial luminance even 860 hours later. Therefore, a long-life light emitting element can be obtained by using the quinoxaline derivative of the invention.

Embodiment 4

In this embodiment, the light emitting element of the invention is described with reference to FIG. 37.

Indium tin oxide containing silicon oxide is formed over a glass substrate 2101 by sputtering as a first electrode 2102. The film thickness of the first electrode is 110 nm and the area thereof is 2 mm×2 mm.

The substrate provided with the first electrode is fixed on a substrate holder which is provided in a vacuum evaporation apparatus, in such a way that a surface provided with the first electrode faces downward. After that, the air inside the vacuum evaporation apparatus is evacuated to approximately 10$^{-4}$ Pa. Then, a layer including a composite material 2103 is formed over the first electrode 2102 by co-evaporation of NPB and molybdenum oxide (VI). The film thickness is 50 nm and the weight ratio between NPB and molybdenum oxide (VI) is adjusted to be 4:1 (=NPB:molybdenum oxide).

Then, a hole transporting layer 2104 is formed over the layer including the composite material 2103 so as to have a thickness of 10 nm using NPB by evaporation with resistive heating.

Further, a light emitting layer 2105 is formed over the hole transporting layer 2104 to have a thickness of 30 nm by co-evaporation of 2,3-bis{4-[N,N-di(4-bipheniryl)amino]phenyl}quinoxaline (hereinafter referred to as BBAPQ) which is the quinoxaline derivative of the invention expressed by the structure formula (39) and (acetylacetonate)bis[2,3-bis(4-fluorophenyl)quinoxalinato]iridium(III) (hereinafter referred to as Ir(Fdpq)$_2$(acac)) which is expressed by the structure formula (114). Here, the weight ratio between BBAPQ and Ir(Fdpq)$_2$(acac) is adjusted to be 1:0.1 (=BBAPQ:Ir(Fdpq)$_2$(acac)). Consequently, Ir(Fdpq)$_2$(acac) is dispersed in the layer containing BBAPQ.

After that, an electron transporting layer 2106 is formed over the light emitting layer 2105 by depositing Alq so as to have a thickness of 10 nm by evaporation with resistive heating.

Further, an electron injecting layer 2107 is formed over the electron transporting layer 2106 so as to have a thickness of 50 nm by co-evaporation of Alq and lithium. The weight ratio between Alq and lithium is adjusted to be 1:0.01 (=Alq:lithium). Consequently, lithium is dispersed in a layer containing Alq.

Finally, a second electrode 2108 is formed over the electron injecting layer 2107 by depositing aluminum so as to have a thickness of 200 nm by evaporation with resistive heating. Thus, the light emitting element of Embodiment 4 is formed.

Figure 24:
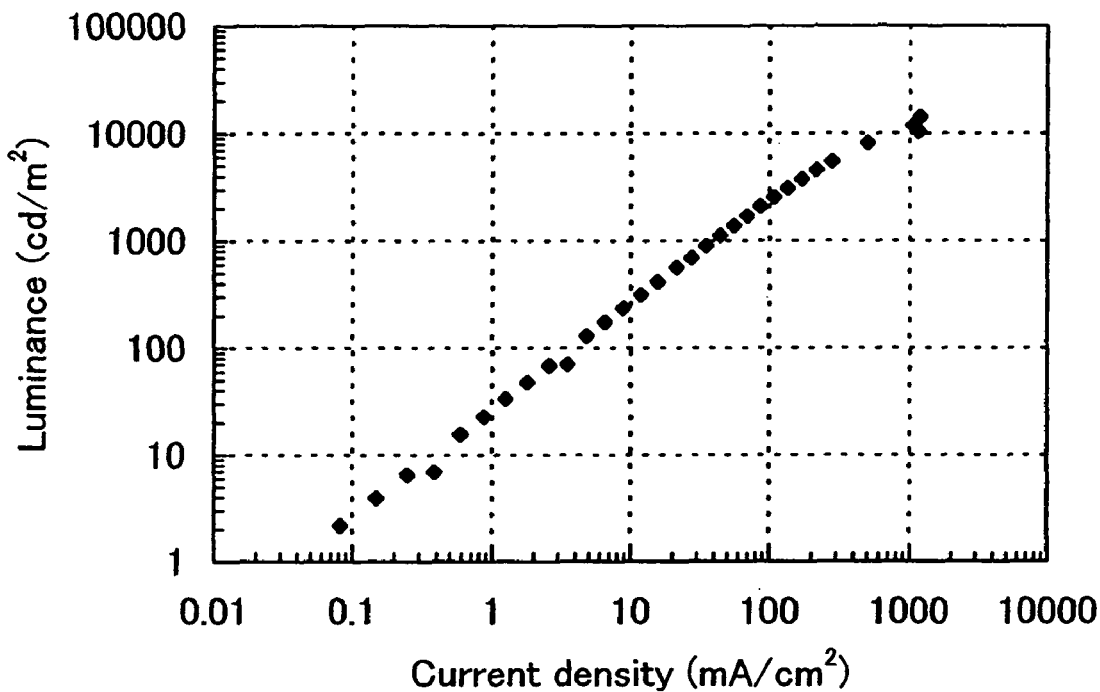
FIG. 24 is a graph showing current density-luminance characteristics of a light emitting element in Embodiment 4.
Figure 25:
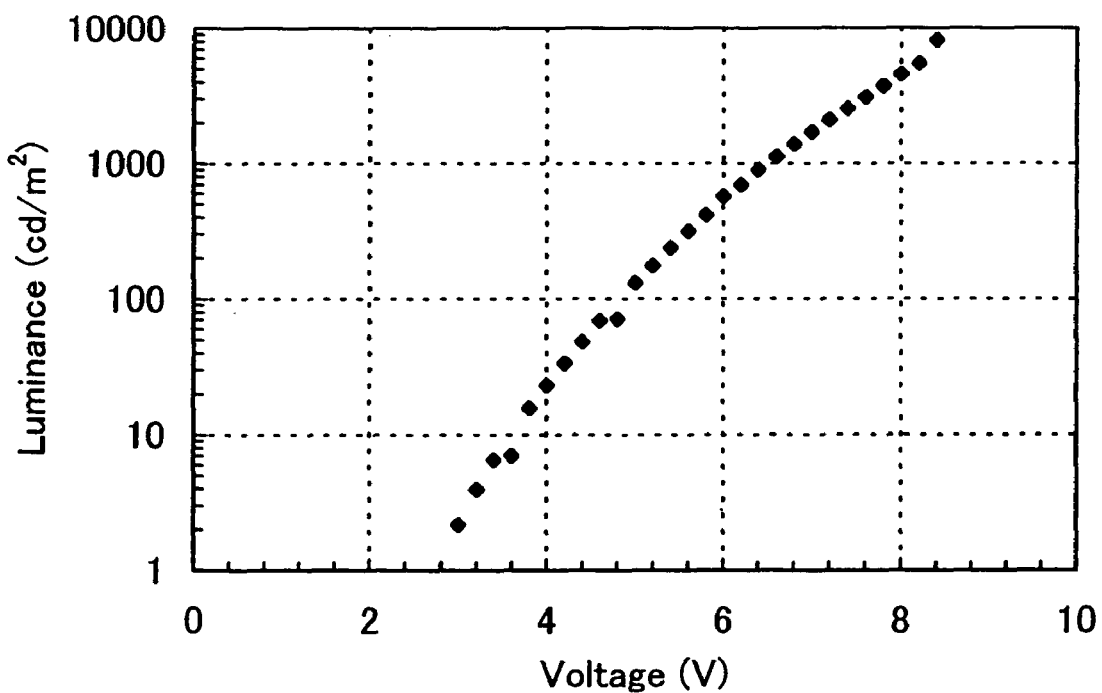
FIG. 25 is a graph showing voltage-luminance characteristics of the light emitting element in Embodiment 4.
Figure 26:
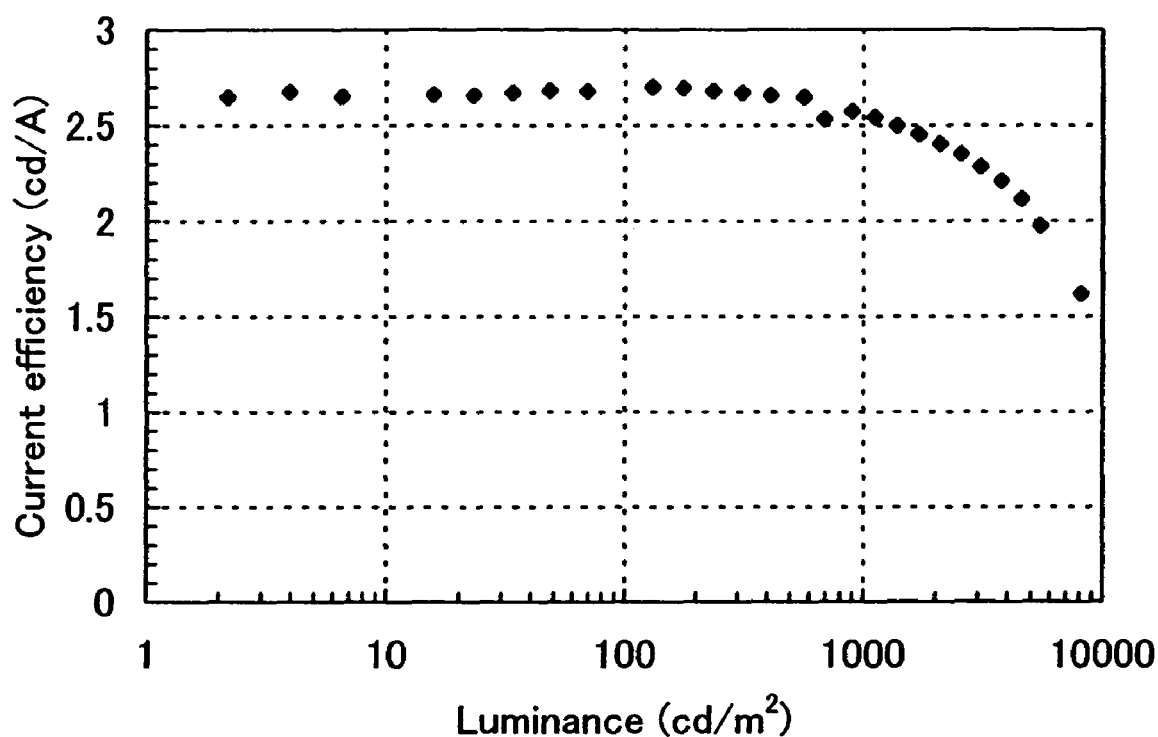
FIG. 26 is a graph showing luminance-current efficiency characteristics of the light emitting element in Embodiment 4.
Figure 34:
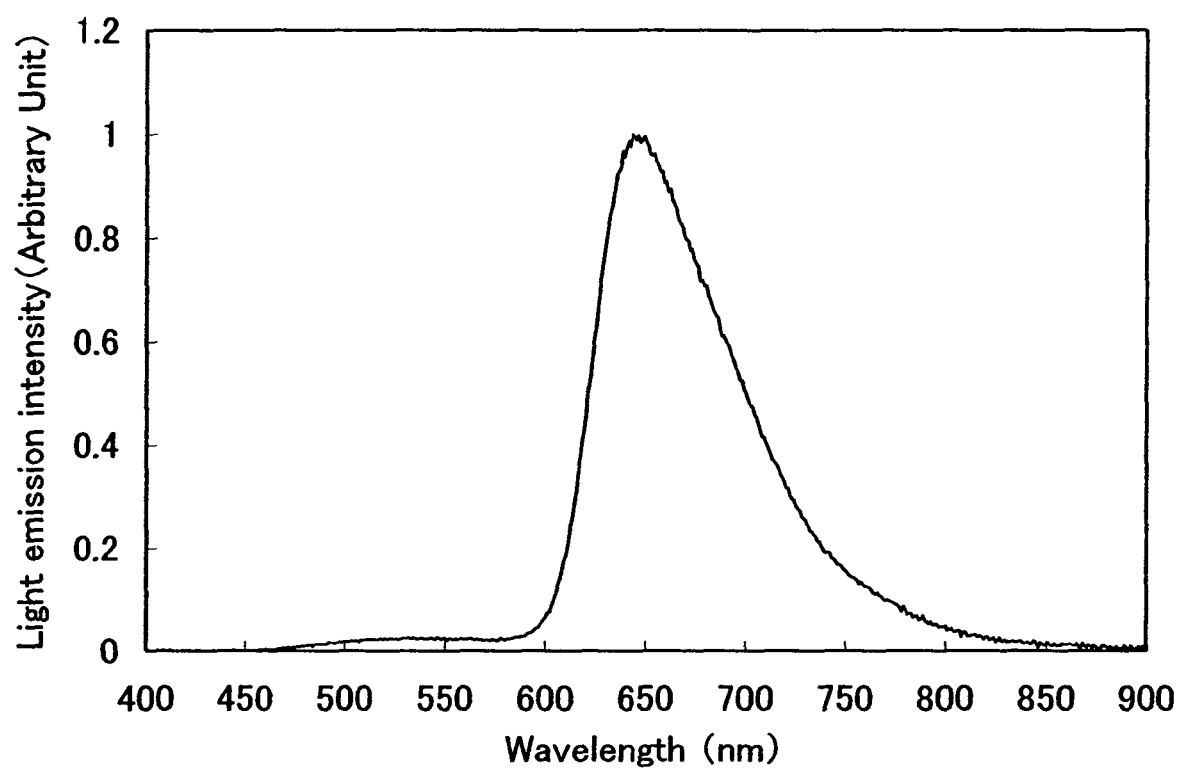
FIG. 34 is a graph showing a light emission spectrum of the light emitting element in Embodiment 4.

Current density-luminance characteristics of the light emitting element of Embodiment 4 are shown in FIG. 24. Luminance-voltage characteristics thereof are shown in FIG. 25. Current efficiency-luminance characteristics thereof are shown in FIG. 26. Also, a light emission spectrum upon applying a current of 1 mA through the light emitting element is shown in FIG. 34. In the light emitting element of Embodiment 4, the voltage required for obtaining a luminance of 900 cd/m$^2$ is 6.4 V. The current flowing through the light emitting element in this case is 1.39 mA (the current density is 34.8 mA/cm$^2$). The CIE chromaticity coordinates are (x=0.65, y=0.33). In addition, the current efficiency and the power efficiency in this case are 2.6 cd/A and 1.31 m/W respectively.

As described above, a red light emitting element consuming low power can be formed by combining the quinoxaline derivative of the invention and the organometallic complex.

Embodiment 5

In this embodiment, the light emitting element of the invention is described with reference to FIG. 37.

Indium tin oxide containing silicon oxide is formed over a glass substrate 2101 by sputtering as a first electrode 2102. The film thickness of the first electrode is 110 nm and the area thereof is 2 mm×2 mm.

The substrate provided with the first electrode is fixed on a substrate holder which is provided in a vacuum evaporation apparatus, in such a way that a surface provided with the first electrode faces downward. After that, the air inside the vacuum evaporation apparatus is evacuated to approximately 10$^{-4}$ Pa. Then, a layer including a composite material 2103 is formed over the first electrode 2102 by co-evaporation of DNTPD and molybdenum oxide (VI). The film thickness is 50 nm and the weight ratio between DNTPD and molybdenum oxide (VI) is adjusted to be 4:2 (=DNTD:molybdenum oxide).

Then, a hole transporting layer 2104 is formed over the layer including the composite material 2103 so as to have a thickness of 10 nm using NPB by evaporation with resistive heating.

Further, a light emitting layer 2105 is formed over the hole transporting layer 2104 to have a thickness of 30 nm by co-evaporation of 2,3-bis{4-[N-(4-bipheniryl)-N-phenylamino]phenyl}quinoxaline (hereinafter referred to as BPAPQ) which is the quinoxaline derivative of the invention expressed by the structure formula (14) and (acetylacetonate)bis[2,3-bis(4-fluorophenyl)quinoxalinato]iridium(III) (hereinafter referred to as Ir(Fdpq)$_2$(acac)) which is expressed by the structure formula (114). Here, the weight ratio between BPAPQ and Ir(Fdpq)$_2$(acac) is adjusted to be 1:0.1 (=BPAPQ Ir(Fdpq)$_2$(acac)). Consequently, Ir(Fdpq)$_2$(acac) is dispersed in the layer containing BPAPQ.

After that, an electron transporting layer 2106 is formed over the light emitting layer 2105 by depositing Alq and BPhen so as to have thicknesses of 10 nm and 50 nm respectively by evaporation with resistive heating.

Further, an electron injecting layer 2107 is formed over the electron transporting layer 2106 by depositing lithium fluoride so as to have a thickness of 1 nm.

Finally, a second electrode 2108 is formed over the electron injecting layer 2107 by depositing aluminum so as to have a thickness of 200 nm by evaporation with resistive heating. Thus, the light emitting element of Embodiment 5 is formed.

Figure 27:
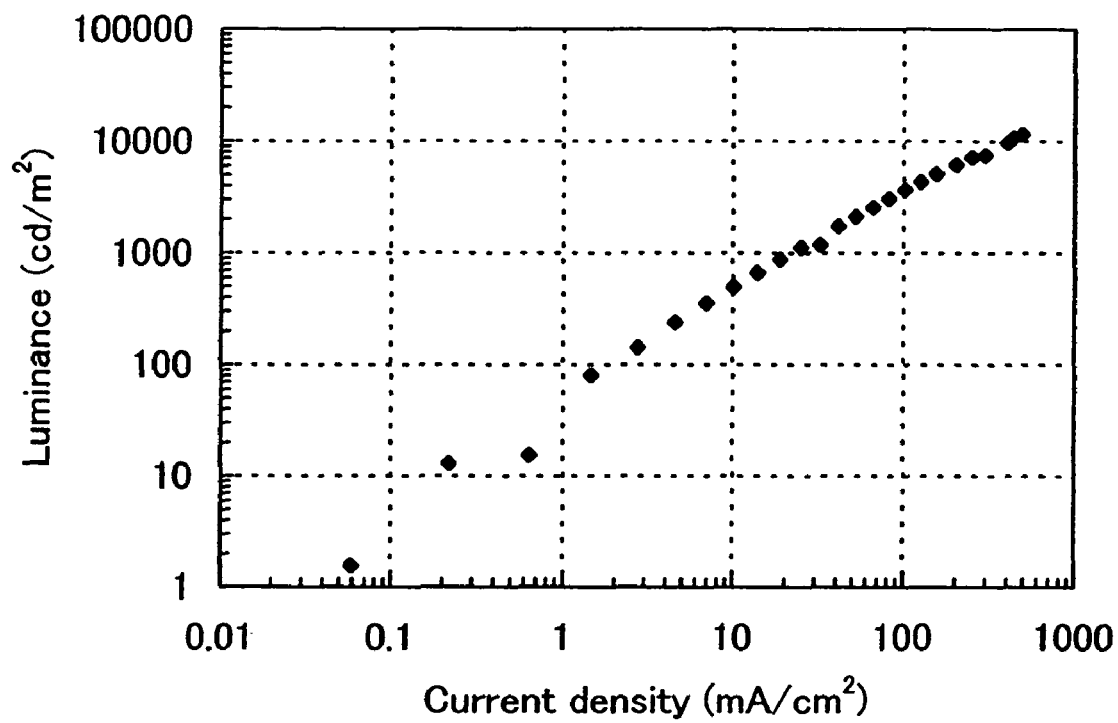
FIG. 27 is a graph showing current density-luminance characteristics of a light emitting element in Embodiment 5.
Figure 28:
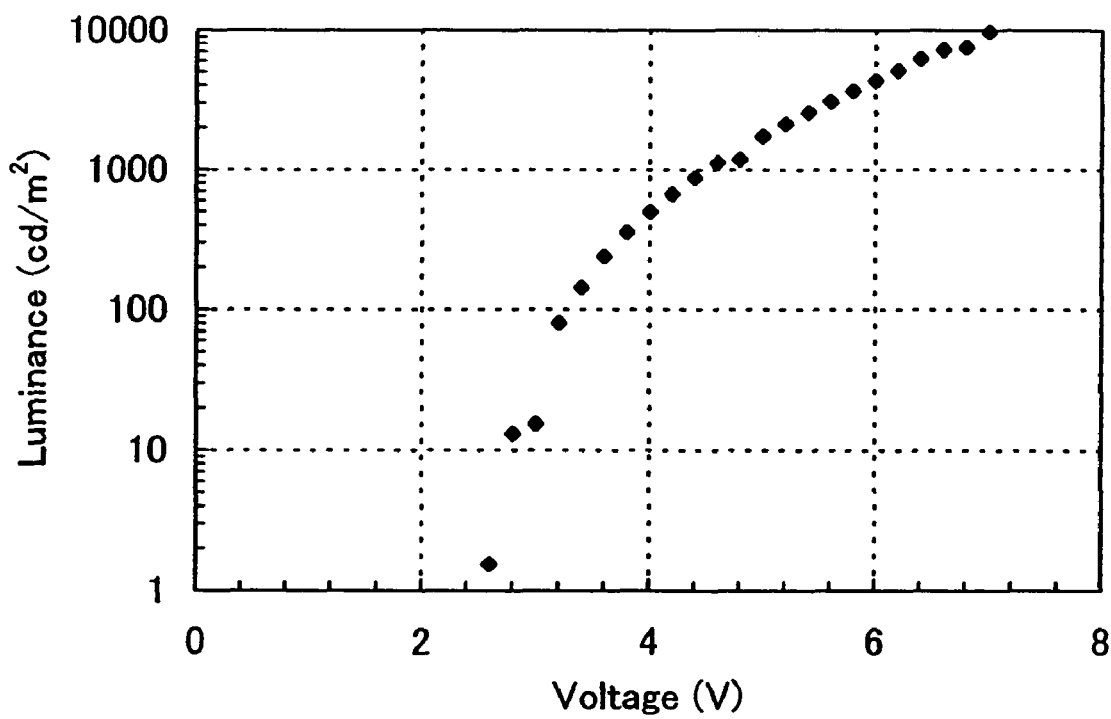
FIG. 28 is a graph showing voltage-luminance characteristics of the light emitting element in Embodiment 5.
Figure 29:
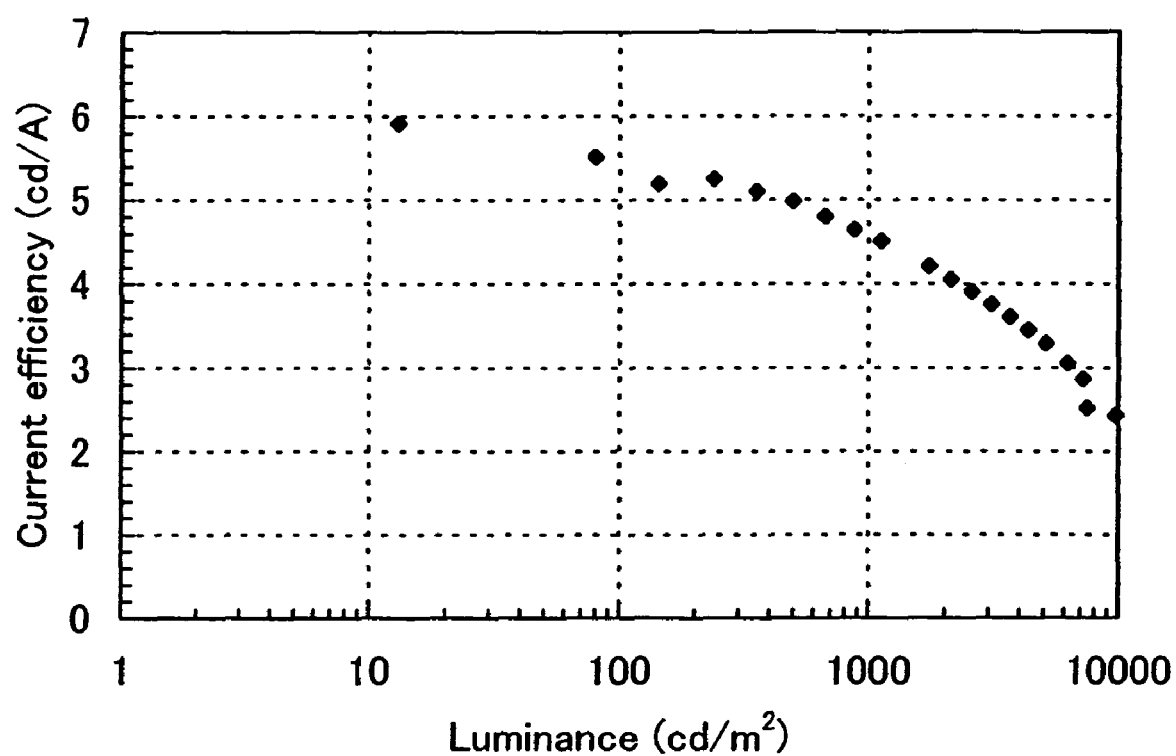
FIG. 29 is a graph showing luminance-current efficiency characteristics of the light emitting element in Embodiment 5.
Figure 35:
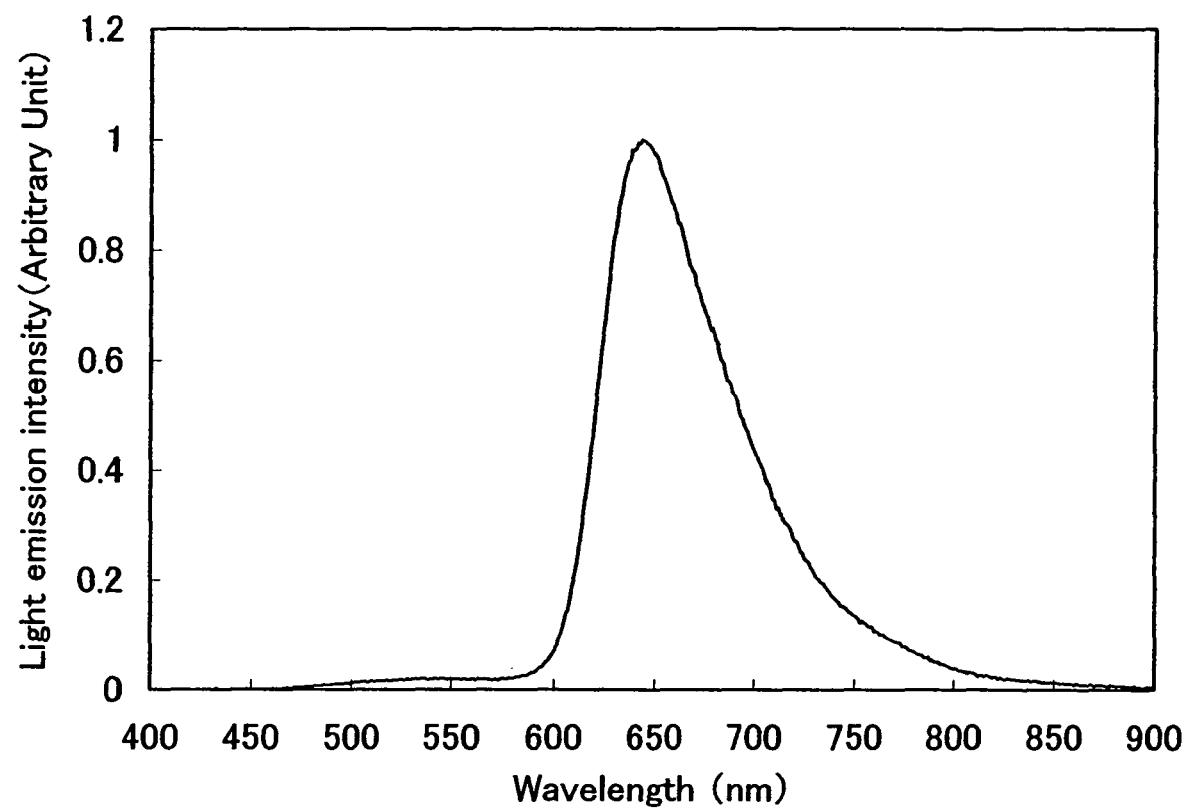
FIG. 35 is a graph showing a light emission spectrum of the light emitting element in Embodiment 5.

Current density-luminance characteristics of the light emitting element of Embodiment 5 are shown in FIG. 27. Luminance-voltage characteristics thereof are shown in FIG. 28. Current efficiency-luminance characteristics thereof are shown in FIG. 29. Also, a light emission spectrum upon applying a current of 1 mA through the light emitting element is shown in FIG. 35. In the light emitting element of Embodiment 5, the voltage required for obtaining a luminance of 1100 cd/m² is 6.8 V. The current flowing through the light emitting element in this case is 0.99 mA (the current density is 24.8 mA/cm²). The CIE chromaticity coordinates are (x=0.68, y=0.31). In addition, the current efficiency and the power efficiency in this case are 4.5 cd/A and 2.11 m/W respectively.

As described above, a red light emitting element consuming low power can be formed by combining the quinoxaline derivative of the invention and the organometallic complex.

Embodiment 6

In this embodiment, the light emitting element of the invention is described with reference to FIG. 37.

Indium tin oxide containing silicon oxide is formed over a glass substrate 2101 by sputtering as a first electrode 2102. The film thickness of the first electrode is 110 nm and the area thereof is 2 mm×2 mm.

The substrate provided with the first electrode is fixed on a substrate holder which is provided in a vacuum evaporation apparatus, in such a way that a surface provided with the first electrode faces downward. After that, the air inside the vacuum evaporation apparatus is evacuated to approximately $10^{-4}$ Pa. Then, a layer including a composite material 2103 is formed over the first electrode 2102 by co-evaporation of t-BuDNA and molybdenum oxide (VI). The film thickness is 50 nm and the weight ratio between the t-BuDNA and the molybdenum oxide (VI) is adjusted to be 4:1 (=t-BuDNA: molybdenum oxide).

Then, a hole transporting layer 2104 is formed over the layer including the composite material 2103 so as to have a thickness of 10 nm using NPB by evaporation with resistive heating.

Further, a light emitting layer 2105 is formed over the hole transporting layer 2104 to have a thickness of 30 nm by co-evaporation of 2,3-bis{4-[N-(4-bipheniryl)-N-phenylamino]phenyl}quinoxaline (hereinafter referred to as BPAPQ) which is the quinoxaline derivative of the invention expressed by the structure formula (14) and (acetylacetonate) bis[2,3-bis(4-fluorophenyl)quinoxalinato]iridium(III) (hereinafter referred to as Ir(Fdpq)$_2$(acac)) which is expressed by the structure formula (114). Here, the weight ratio between BPAPQ and Ir(Fdpq)$_2$(acac) is adjusted to be 1:0.1 (=BPAPQ:Ir(Fdpq)$_2$(acac)). Consequently, Ir(Fdpq)$_2$(acac) is dispersed in the layer containing BPAPQ.

After that, an electron transporting layer 2106 is formed over the light emitting layer 2105 by depositing Alq so as to have a thickness of 10 nm by evaporation with resistive heating.

Further, an electron injecting layer 2107 is formed over the electron transporting layer 2106 so as to have a thickness of 50 nm by co-evaporation of Alq and lithium. The weight ratio between Alq and lithium is adjusted to be 1:0.01 (=Alq: lithium). Consequently, lithium is dispersed in the layer containing Alq.

Finally, a second electrode 2108 is formed over the electron injecting layer 2107 by depositing aluminum so as to have a thickness of 200 nm by evaporation with resistive heating. Thus, the light emitting element of Embodiment 6 is formed.

Figure 30:
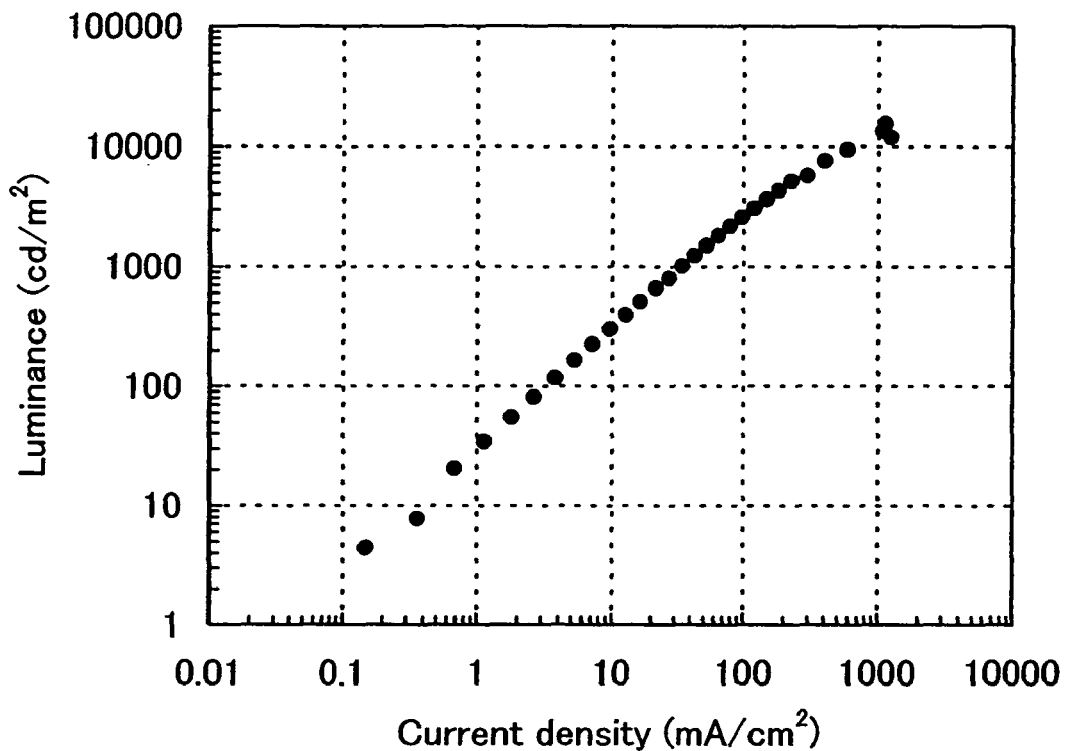
FIG. 30 is a graph showing current density-luminance characteristics of a light emitting element in Embodiment 6.
Figure 31:
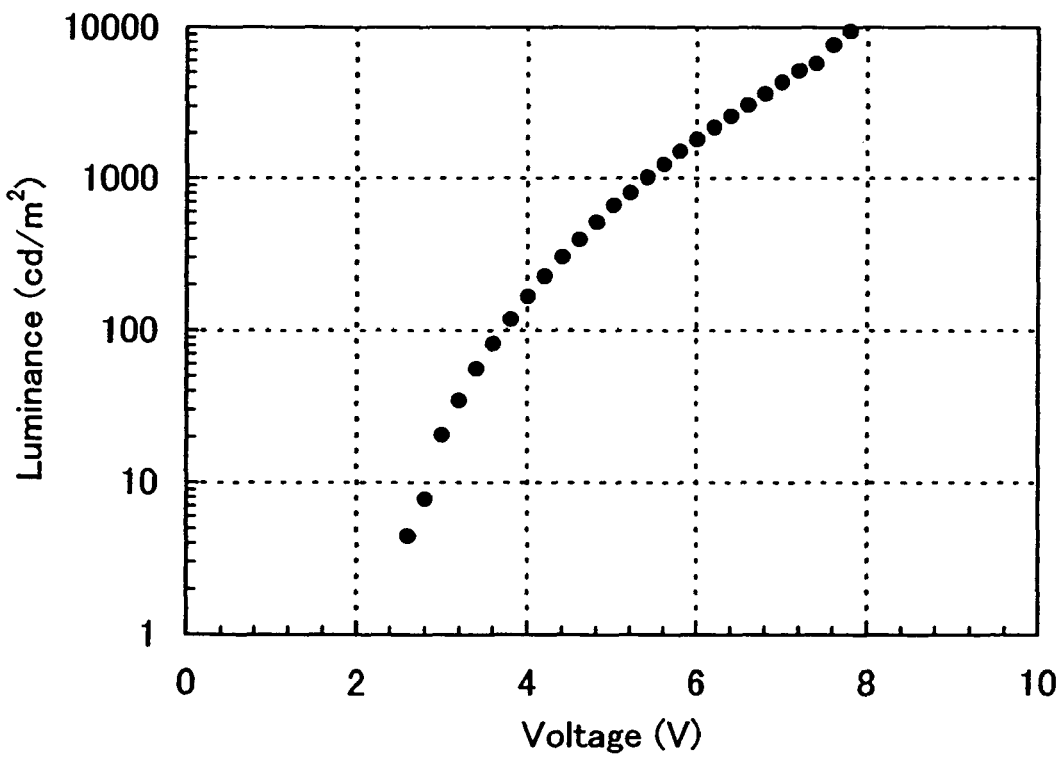
FIG. 31 is a graph showing voltage-luminance characteristics of the light emitting element in Embodiment 6.
Figure 32:
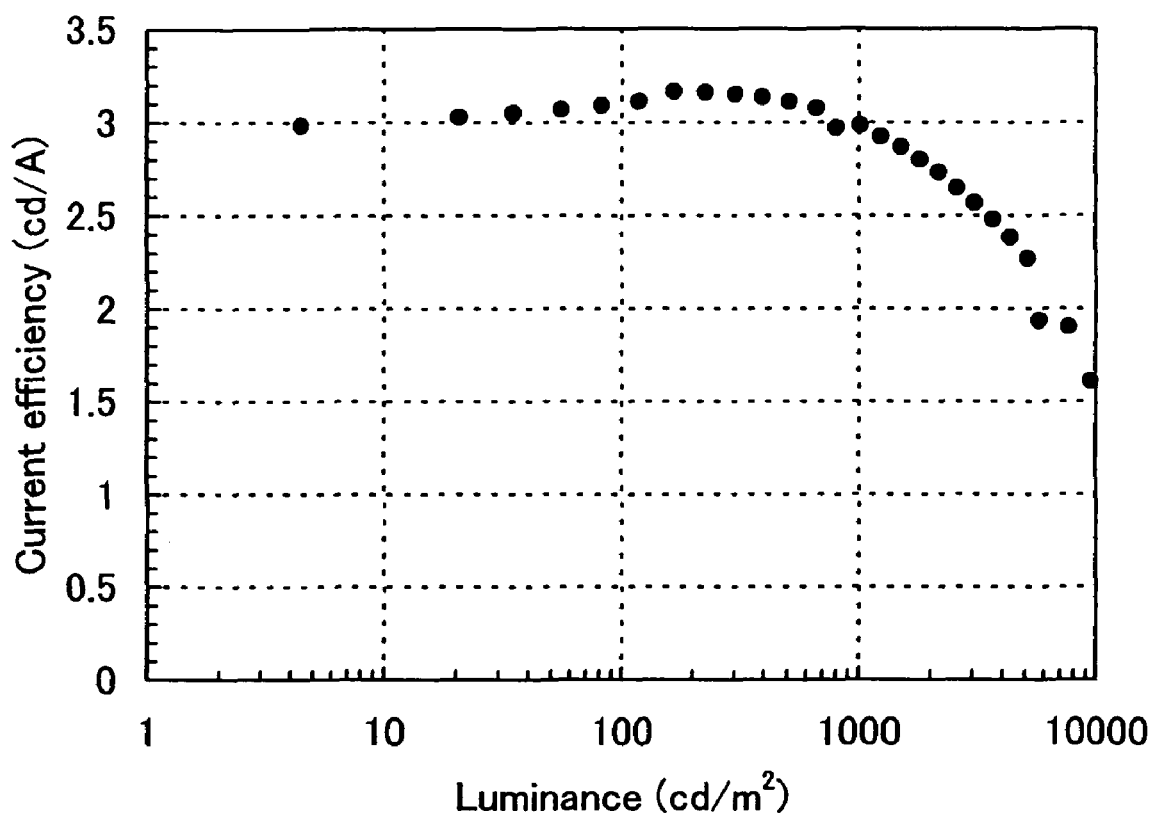
FIG. 32 is a graph showing luminance-current efficiency characteristics of the light emitting element in Embodiment 6.
Figure 36:
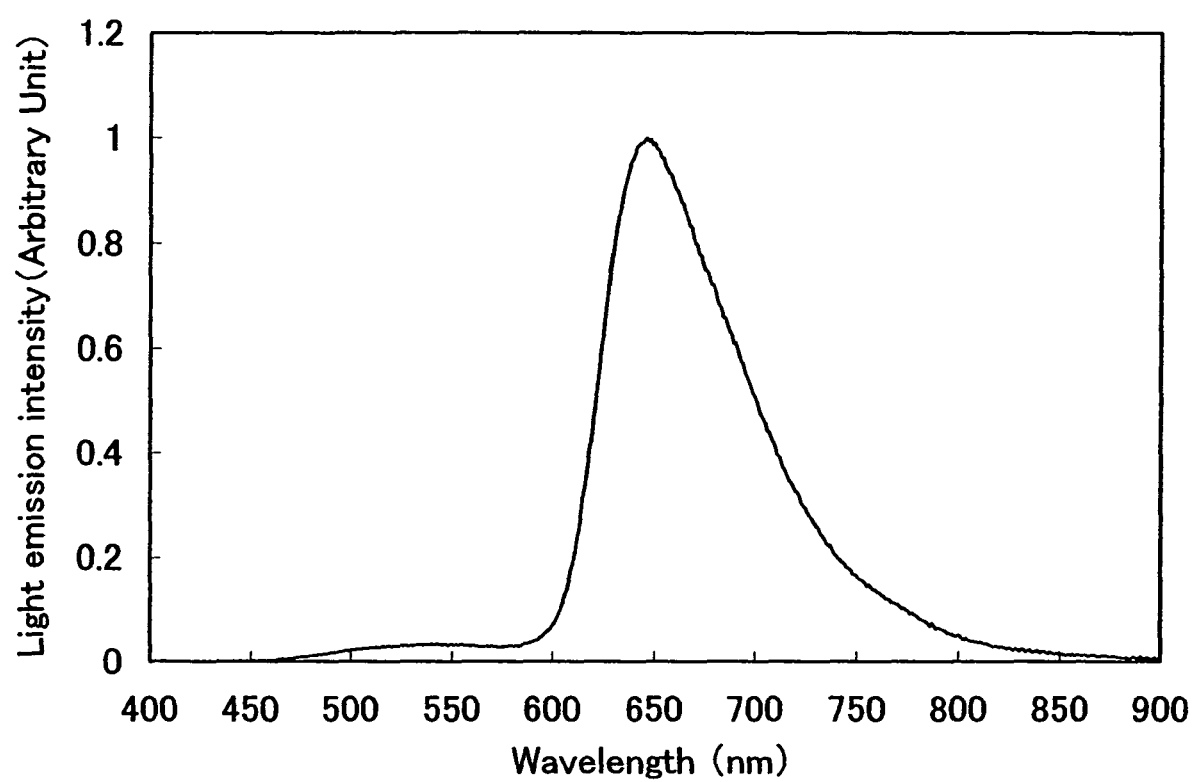
FIG. 36 is a graph showing a light emission spectrum of the light emitting element in Embodiment 6.

Current density-luminance characteristics of the light emitting element of Embodiment 6 are shown in FIG. 30. Luminance-voltage characteristics thereof are shown in FIG. 31. Current efficiency-luminance characteristics thereof are shown in FIG. 32. Also, a light emission spectrum upon applying a current of 1 mA through the light emitting element is shown in FIG. 36. In the light emitting element of Embodiment 6, the voltage required for obtaining a luminance of 1000 cd/m² is 5.4 V. The current flowing through the light emitting element in this case is 1.36 mA (the current density is 33.9 mA/cm²). The CIE chromaticity coordinates are (x=0.65, y=0.33). In addition, the current efficiency and the power efficiency in this case are 3.0 cd/A and 1.71 m/W respectively.

As described above, a red light emitting element consuming low power can be formed by combining the quinoxaline derivative of the invention and the organometallic complex.

Further, initial luminance of the light emitting element of Embodiment Mode 6 is set to be 1000 cd/m². Under such a condition, a continuous lighting test is carried out by constant current driving. Then, it is found that the light emitting element still holds 70% of the initial luminance even 2500 hours later. Therefore, a long-life light emitting element can be obtained by using the quinoxaline derivative of the invention.

Embodiment 7

In this embodiment, the light emitting element of the invention is described with reference to FIG. 37.

Indium tin oxide containing silicon oxide is formed over the glass substrate 2101 by sputtering as a first electrode 2102. The film thickness of the first electrode is 110 nm and the area thereof is 2 mm×2 mm.

The substrate provided with the first electrode is fixed on a substrate holder which is provided in a vacuum evaporation apparatus, in such a way that a surface provided with the first electrode faces downward. After that, the air inside the vacuum evaporation apparatus is evacuated to approximately $10^{-4}$ Pa. Then, a layer including a composite material 2103 is formed over the first electrode 2102 by co-evaporation of NPB and molybdenum oxide (VI). The film thickness is 50 nm and the weight ratio between NPB and molybdenum oxide (VI) is adjusted to be 4:1 (=NPB:molybdenum oxide).

Then, a hole transporting layer 2104 is formed over the layer including the composite material 2103 so as to have a thickness of 10 nm using NPB by evaporation with resistive heating.

Further, a light emitting layer 2105 is formed over the hole transporting layer 2104 to have a thickness of 30 nm by co-evaporation of 2,3-bis{4-[N-(4-bipheniryl)-N-phenylamino]phenyl}quinoxaline (hereinafter referred to as BPAPQ) which is the quinoxaline derivative of the invention expressed by the structure formula (14) and (acetylacetonate) bis[2-(4-fluorophenyl)-3-methylquinoxalinato]iridium(III) (hereinafter referred to as Ir(MFpq)$_2$(acac)) which is expressed by the structure formula (123). Here, the weight ratio between BPAPQ and Ir(MFpq)$_2$(acac) is adjusted to be 1:0.01 (=BPAPQ:Ir(MFpq)$_2$(acac)). Consequently, Ir (MFpq)$_2$(acac) is dispersed in the layer containing BPAPQ.

After that, an electron transporting layer 2106 is formed over the light emitting layer 2105 by depositing BAlq so as to have a thickness of 10 nm by evaporation with resistive heating.

Further, an electron injecting layer 2107 is formed over the electron transporting layer 2106 so as to have a thickness of 50 nm by co-evaporation of Alq and lithium. Here, the weight ratio between Alq and lithium is adjusted to be 1:0.01 (=Alq: lithium). Consequently, lithium is dispersed in the layer containing Alq.

Finally, a second electrode 2108 is formed over the electron injecting layer 2107 by depositing aluminum so as to have a thickness of 200 nm by evaporation with resistive heating. Thus, the light emitting element of Embodiment 7 is formed.

Figure 38:
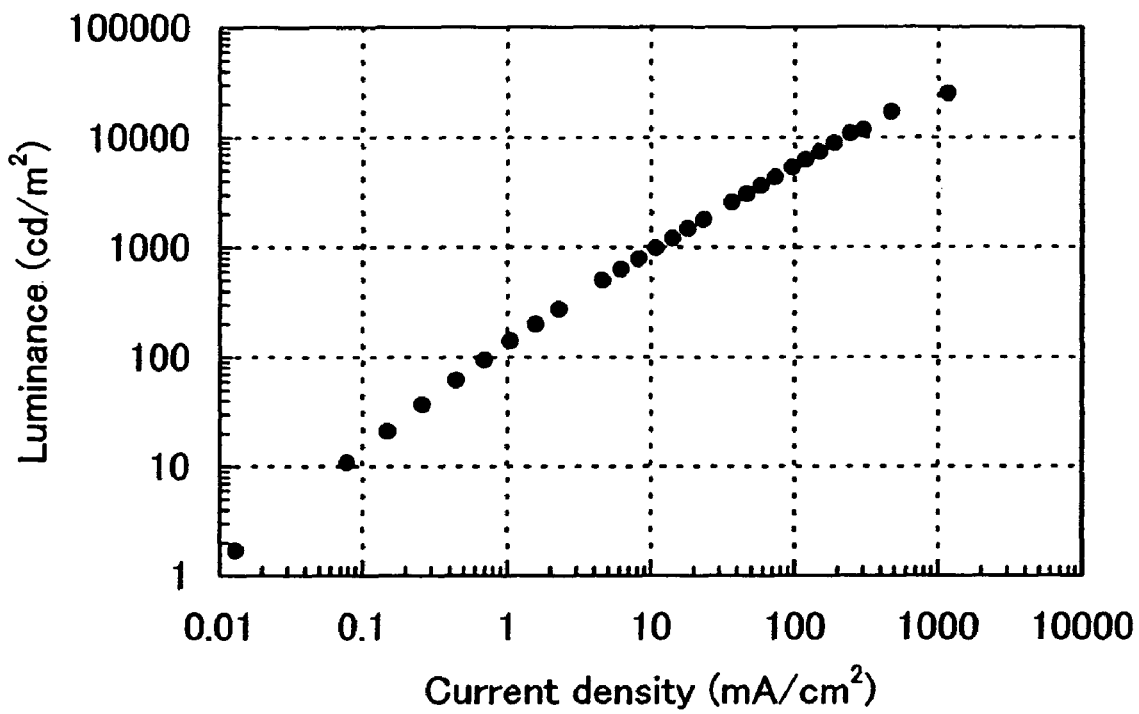
FIG. 38 is a graph showing current density-luminance characteristics of a light emitting element in Embodiment 7.

Current density-luminance characteristics of the light emitting element of Embodiment 7 are shown in FIG. 38.

Figure 39:
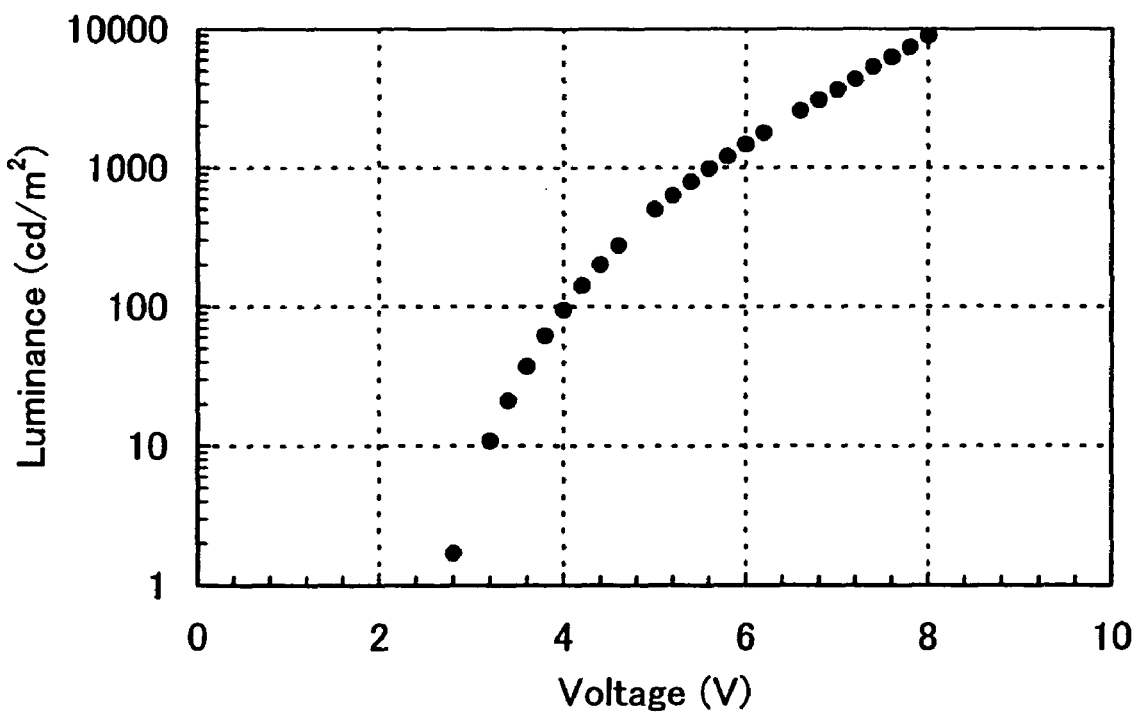
FIG. 39 is a graph showing voltage-luminance characteristics of the light emitting element in Embodiment 7.
Figure 40:
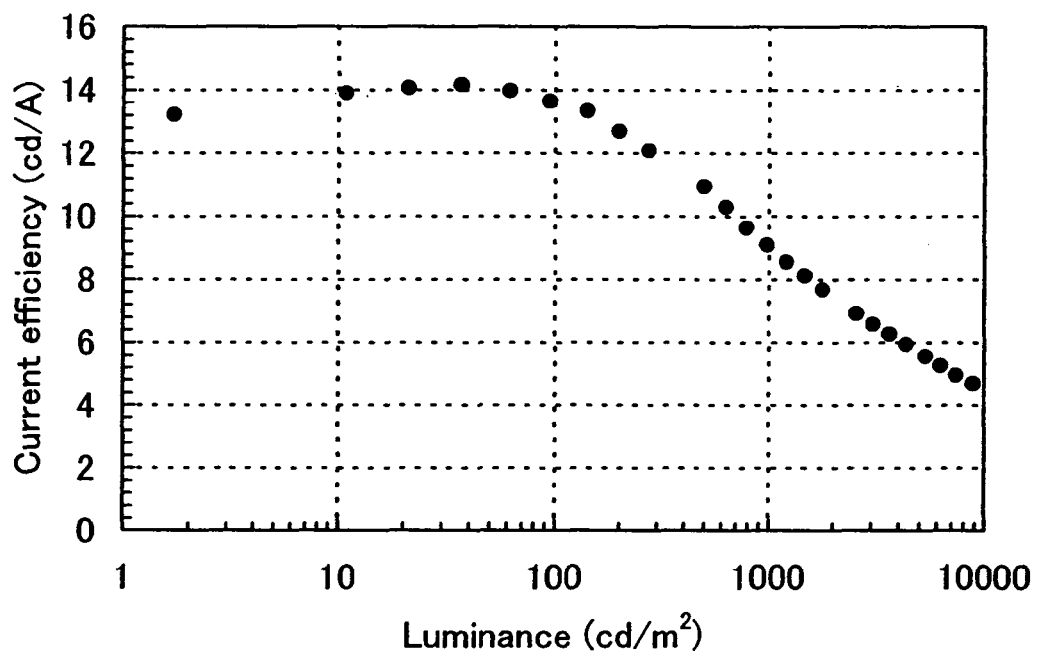
FIG. 40 is a graph showing luminance-current efficiency characteristics of the light emitting element in Embodiment 7.
Figure 41:
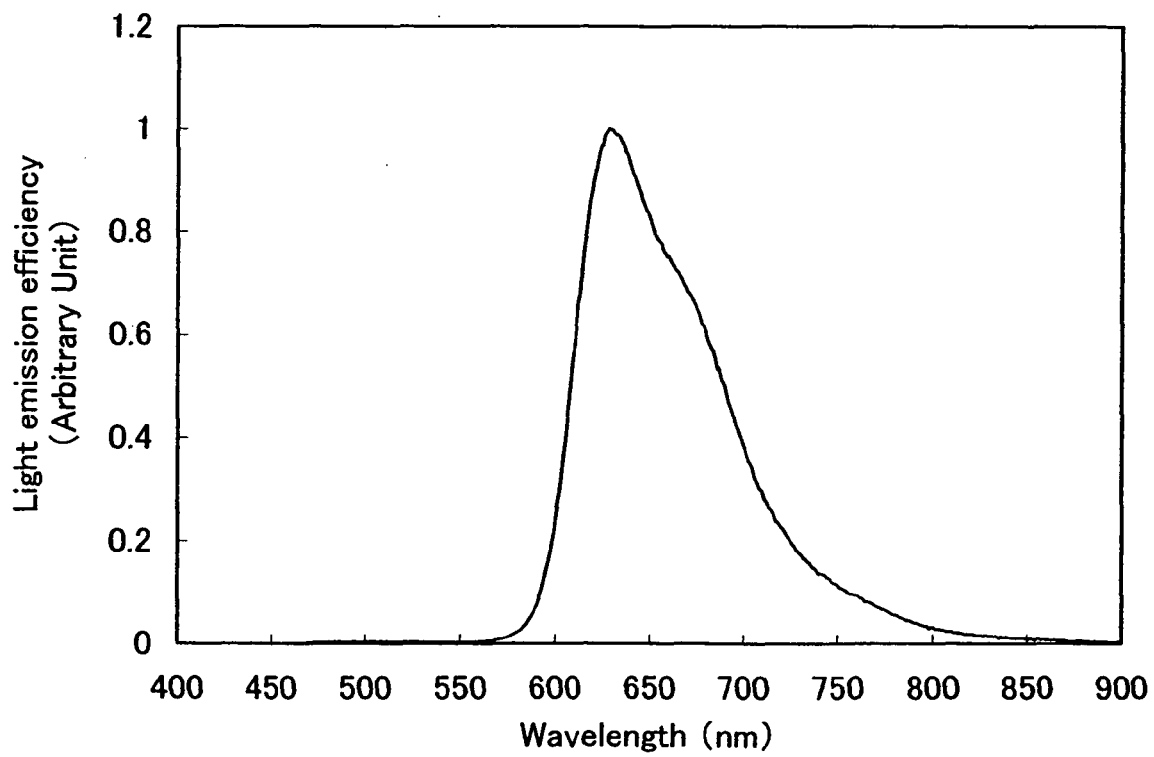
FIG. 41 is a graph showing a light emission spectrum of the light emitting element in Embodiment 7.

Luminance-voltage characteristics thereof are shown in FIG. 39. Current efficiency-luminance characteristics thereof are shown in FIG. 40. Also, a light emission spectrum upon applying a current of 1 mA through the light emitting element is shown in FIG. 41. In the light emitting element of Embodiment 7, the voltage required for obtaining a luminance of 1000 cd/m² is 5.6 V The current flowing through the light emitting element in this case is 0.43 mA (the current density is 10.8 mA/cm²). The CIE chromaticity coordinates are (x=0.69, y=0.31). In addition, the current efficiency and the power efficiency in this case are 9.1 cd/A and 5.11 m/W respectively.

Further, initial luminance of the light emitting element of Embodiment Mode 7 is set to be 1000 cd/m². Under such a condition, a continuous lighting test is carried out by constant current driving. Then, it is found that the light emitting element still holds 90% of the initial luminance even 310 hours later and has a long life. That is, a long-life light emitting element can be obtained by applying the invention.

Further, a red light emitting element consuming low power can be obtained by combining the quinoxaline derivative of the invention and the organometallic complex.

Further, the light emitting element of this embodiment has high light emission efficiency. Therefore, the light emitting element which consumes low power can be obtained.

This application is based on Japanese Patent Application serial no. 2005-264253 filed in Japan Patent Office on 12, Sep., 2005, the entire contents of which are hereby incorporated by reference.

EXPLANATION OF REFERENCE

101: substrate, 102: first electrode, 103: first layer, 104: second layer, 105: third layer, 106: fourth layer, 107: second electrode, 302: first electrode, 303: first layer, 304: second layer, 305: third layer, 306: fourth layer, 307: second electrode, 601: source side driver circuit, 602: pixel portion, 603: gate side driver circuit, 604: sealing substrate, 605: sealing material, 607: space, 608: wiring, 609: FPC (flexible printed circuit), 610: element substrate, 611: switching TFT, 612: current control TFT, 613: first electrode, 614: insulator, 616: layer including a light emitting substance, 617: second electrode, 618: light emitting element, 623: n-channel TFT, 624: p-channel TFT, 901: housing, 902: liquid crystal layer, 903: backlight, 904: housing, 905: driver IC, 906: terminal, 951: substrate, 952: electrode, 953: insulating layer, 954: partition layer, 955: layer including a light emitting substance, 956: electrode, 1201: source electrode, 1202: active layer, 1203: drain electrode, 1204: gate electrode, 2101: substrate, 2102: first electrode, 2103: layer including a composite material, 2104: hole transporting layer, 2105: light emitting layer, 2106: electron transporting layer, 2107: electron injecting layer, 2108: second electrode, 9101: housing, 9102: supporting base, 9103: display portion, 9104: speaker portion, 9105: video input terminal, 9201: main body, 9202: housing, 9203: display portion, 9204: keyboard, 9205: external connection port, 9206: pointing mouse, 9401: main body, 9402: housing, 9403: display portion, 9404: audio input portion, 9405: audio output portion, 9406: operation key, 9407: external connection port, 9408: antenna, 9501: main body, 9502: display portion, 9503: housing, 9504: external connection port, 9505: remote control receiving portion, 9506: image receiving portion, 9507: battery, 9508: audio input portion, 9509: operation keys, 9510: eyepiece portion

The invention claimed is:

1. A quinoxaline derivative expressed by a general formula (1):

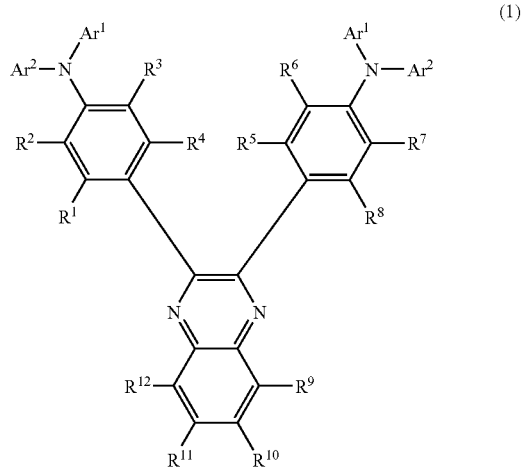

(1)

(wherein each of $R^1$ to $R^{12}$ represents one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group, and wherein $Ar^1$ represents one of a substituted or unsubstituted biphenyl group and a substituted or unsubstituted terphenyl group, and $Ar^2$ represents one of a substituted or unsubstituted phenyl group, a substituted or unsubstituted biphenyl group, a substituted or unsubstituted terphenyl group, and a substituted or unsubstituted monocyclic heterocycle group.)

2. A quinoxaline derivative expressed by a general formula (2):

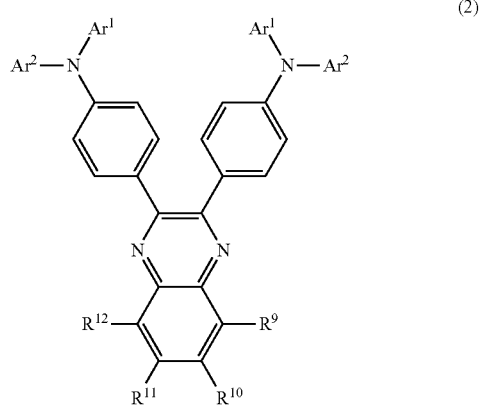

(2)

(wherein each of $R^9$ to $R^{12}$ represents one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group, and wherein $Ar^1$ represents one of a substituted or unsubstituted biphenyl group and a substituted or unsubstituted terphenyl group and $Ar^2$ represents one of a substituted or unsubstituted phenyl group, a substituted or unsubstituted biphenyl group, a substituted or unsubstituted terphenyl group, and a substituted or unsubstituted monocyclic heterocycle group.)

3. A quinoxaline derivative expressed by a general formula (3):

(3)

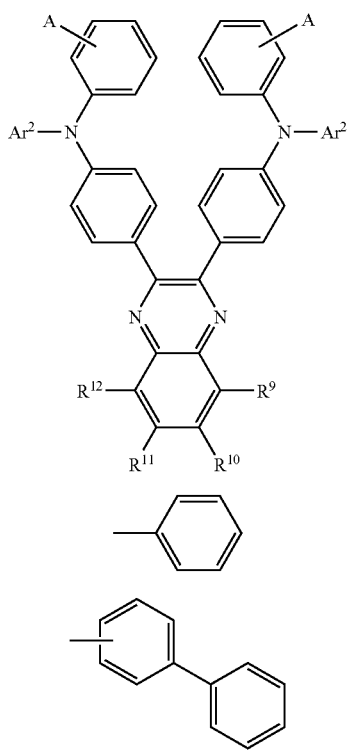

(4)

(5)

(wherein each of $R^9$ to $R^{12}$ represents one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group, and wherein A represents a substituent expressed by one of a structure formula (4) and a structure formula (5) and $Ar^2$ represents one of a substituted or unsubstituted phenyl group, a substituted or unsubstituted biphenyl group, a substituted or unsubstituted terphenyl group, and a substituted or unsubstituted monocyclic heterocycle group.)

4. A quinoxaline derivative expressed by a general formula (6):

(6)

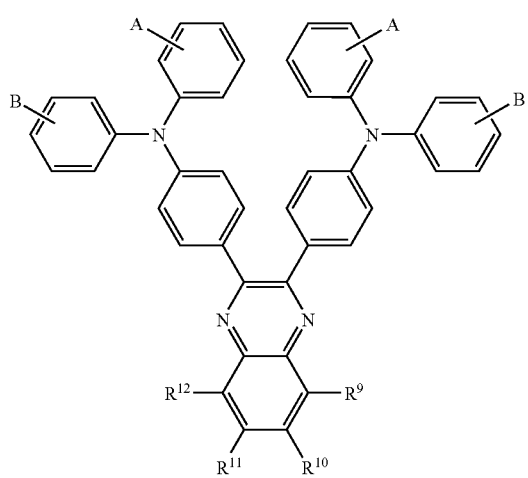

(7)

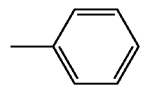

(8)

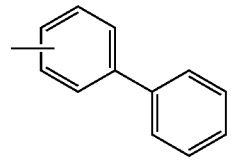

(wherein each of $R^9$ to $R^{12}$ represents one of a hydrogen atom, a halogen atom, an alkyl group, an alkoxyl group, an acyl group, a dialkyl amino group, a diarylamino group, a substituted or unsubstituted vinyl group, a substituted or unsubstituted aryl group, and a substituted or unsubstituted heterocycle group, and wherein A represents a substituent expressed by one of a structure formula (7) a structure formula (8) and B represents one of hydrogen atom, a substituent expressed by the structure formula (7), and a substituent expressed by the structure formula (8).)

5. A quinoxaline derivative expressed by a general formula (9):

(9)

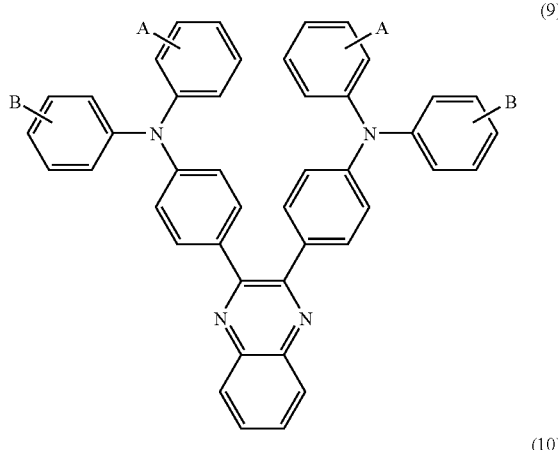

(10)

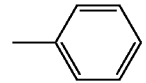

(11)

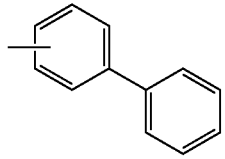

(wherein A represents a substituent expressed by one of a structure formula (10) and a structure formula (11) and B represents one of a hydrogen atom, a substituent expressed by the structure formula (10) and a substituent expressed by the structure formula (11).)

6. A quinoxaline derivative expressed by a structure formula (14):

(14)

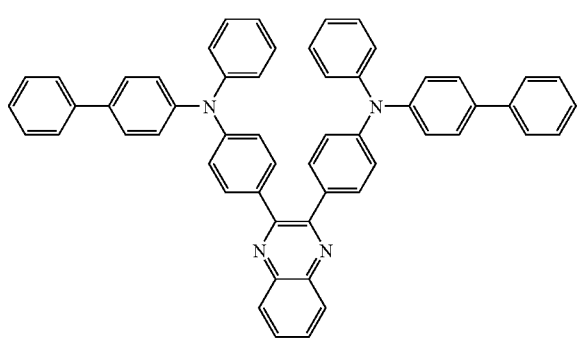

7. A quinoxaline derivative expressed by a structure formula (39):

(39)

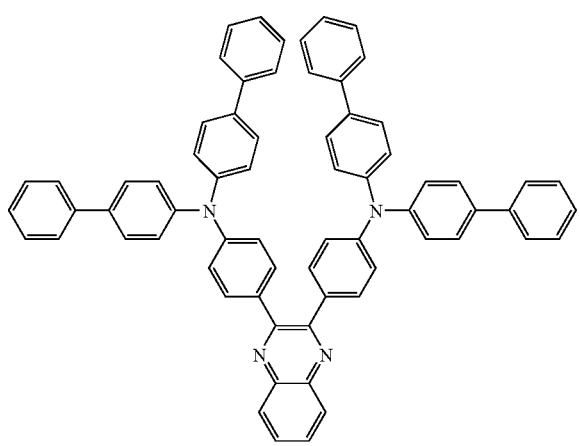

8. A light emitting element comprising the quinoxaline derivative according to any one of claims 1 to 7 between a pair of electrodes.

9. A light emitting element comprising a light emitting layer between a pair of electrodes, wherein the light emitting layer comprises the quinoxaline derivative according to any one of claims 1 to 7.

10. A light emitting element comprising a light emitting layer between a pair of electrodes, wherein the light emitting layer comprises the quinoxaline derivative according to any one of claims 1 to 7 and a fluorescent substance.

11. A light emitting element comprising a light emitting layer between a pair of electrodes, wherein the light emitting layer comprises the quinoxaline derivative according to any one of claims 1 to 7 and a phosphorescent substance.

12. The light emitting element according to claim 11, wherein the phosphorescent substance is an organometallic complex including a structure expressed by a general formula (101):

(101)

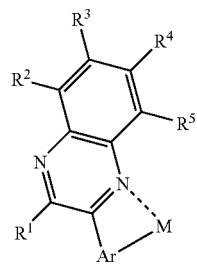

(wherein $R^1$ to $R^5$ each represent one of hydrogen, a halogen element, an acyl group, an alkyl group, an alkoxyl group, an aryl group, a cyano group, and a heterocycle group,
wherein Ar represents one of aryl group and a heterocycle group, and
wherein M represents an element which belongs to one of Group 9 and Group 10.)

13. The light emitting element according to claim 11, wherein the phosphorescent substance is an organometallic complex expressed by a general formula (104):

(104)

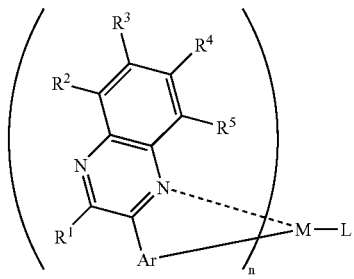

(wherein $R^1$ to $R^5$ each represent one of hydrogen, a halogen element, an acyl group, an alkyl group, an alkoxyl group, an aryl group, a cyano group, and a heterocycle group,
wherein Ar represents one of an aryl group and a heterocycle group,
wherein M represents an element which belongs to one of Group 9 and Group 10 and when M is a Group 9 element, n=2 is satisfied, whereas when M is a Group 10 element, n=1 is satisfied, and
wherein L represents one of a monoanionic ligand having a beta-diketone structure, a monoanionic bidentate chelate ligand having a carboxyl group, and a monoanionic bidentate chelate ligand having a phenol hydroxyl group.)

14. The light emitting element according to claim 11, wherein the phosphorescent substance is an organometallic complex expressed by a general formula (105):

(105)

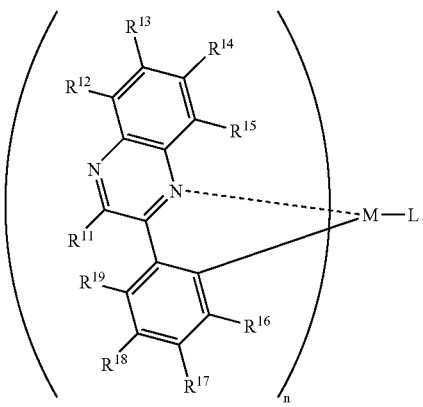

(wherein $R^{11}$ represents one of alkyl groups having 1 to 4 carbon atoms,
wherein $R^{12}$ to $R^{15}$ each represent one of hydrogen, a halogen element, an acyl group, an alkyl group, an alkoxyl group, an aryl group, a cyano group, and a heterocycle group, wherein $R^{16}$ to $R^{19}$ each represent one of hydrogen, an acyl group, an alkyl group, an alkoxyl group, an aryl group, a heterocycle group, and an electron-withdrawing substituent, wherein M represents an element which belongs to one of Group 9 and Group 10 and when M is a Group 9 element, n=2 is satisfied, whereas when M is a Group 10 element, n=1 is satisfied, and wherein L represents one of a monoanionic ligand having a beta-diketone structure, a monoanionic bidentate chelate ligand having a carboxyl group, and a monoanionic bidentate chelate ligand having a phenol hydroxyl group.)

15. The light emitting element according to claim 11, wherein the phosphorescent substance is an organometallic complex expressed by a general formula (106):

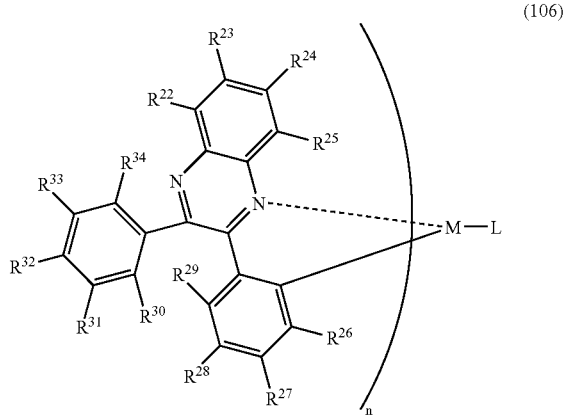

(106)

(wherein $R^{22}$ to $R^{34}$ each represent one of hydrogen, a halogen element, an acyl group, an alkyl group, an alkoxyl group, an aryl group, a cyano group, a heterocycle group, and an electron-withdrawing substituent, wherein M represents an element which belongs to one of Group 9 and Group 10 and when M is a Group 9 element, n=2 is satisfied, whereas when M is a Group 10 element, n=1 is satisfied, and wherein L represents one of a monoanionic ligand having a beta-diketone structure, a monoanionic bidentate chelate ligand having a carboxyl group, and a monoanionic bidentate chelate ligand having a phenol hydroxyl group.)

16. The light emitting element according to claim 11, wherein a light emission spectrum of the phosphorescent substance has a peak at 560 nm to 700 nm.

17. The light emitting element according to any one of claims 12 to 15, wherein a light emission spectrum of the phosphorescent substance has a peak at 560 nm to 700 nm.

18. A light emitting device comprising the light emitting element according to claim 8 and a control means for controlling light emission of the light emitting element.

19. A light emitting device comprising the light emitting element according to claim 9 and a control means for controlling light emission of the light emitting element.

20. A light emitting device comprising the light emitting element according to claim 10 and a control means for controlling light emission of the light emitting element.

21. A light emitting device comprising the light emitting element according to claim 11 and a control means for controlling light emission of the light emitting element.

22. A light emitting device comprising the light emitting element according to any one of claims 12 to 15 and a control means for controlling light emission of the light emitting element.

23. A light emitting device comprising the light emitting element according to claim 16 and a control means for controlling light emission of the light emitting element.

24. A light emitting device comprising the light emitting element according to claim 17 and a control means for controlling light emission of the light emitting element.

25. An electronic appliance comprising a display portion, wherein the display portion is provided with the light emitting element according to claim 8 and a control means for controlling light emission of the light emitting element.

26. An electronic appliance comprising a display portion, wherein the display portion is provided with the light emitting element according to claim 9 and a control means for controlling light emission of the light emitting element.

27. An electronic appliance comprising a display portion, wherein the display portion is provided with the light emitting element according to claim 10 and a control means for controlling light emission of the light emitting element.

28. An electronic appliance comprising a display portion, wherein the display portion is provided with the light emitting element according to claim 11 and a control means for controlling light emission of the light emitting element.

29. An electronic appliance comprising a display portion, wherein the display portion is provided with the light emitting element according to any one of claims 12 to 15 and a control means for controlling light emission of the light emitting element.

30. An electronic appliance comprising a display portion, wherein the display portion is provided with the light emitting element according to claim 16 and a control means for controlling light emission of the light emitting element.

31. An electronic appliance comprising a display portion, wherein the display portion is provided with the light emitting element according to claim 17 and a control means for controlling light emission of the light emitting element.

32. The quinoxaline derivative according to any one of claims 1 to 4, wherein $R^9$, $R^{10}$, and $R^{11}$ are combined with $R^{10}$, $R^{11}$, and $R^{12}$ respectively.

33. The quinoxaline derivative according to any one of claims 1 to 3, wherein a substituent of each of the substituted biphenyl group, the substituted terphenyl group, and the substituted monocyclic heterocycle group is selected from an alkyl group or a phenyl group.

* * * * *

UNITED STATES PATENT AND TRADEMARK OFFICE
CERTIFICATE OF CORRECTION

PATENT NO. : 7,901,792 B2  
APPLICATION NO. : 11/518484  
DATED : March 8, 2011  
INVENTOR(S) : Masakazu Egawa et al.

It is certified that error appears in the above-identified patent and that said Letters Patent is hereby corrected as shown below:

Column 43, Line 9, Change "ITQ" to --ITO--.

Column 44, Line 47, Change "(U)" to --(Li)--.

Column 64, Line 46, Change "AILS" to --ALS--.

Column 70, Line 31, Change "DNTD" to --DNTPD--.

Signed and Sealed this
Sixth Day of December, 2011

David J. Kappos
*Director of the United States Patent and Trademark Office*